United States Patent
Brun et al.

(10) Patent No.: US 7,799,093 B2
(45) Date of Patent: Sep. 21, 2010

(54) COLORING COMPOSITION OF KERATINOUS FIBERS COMPRISING AT LEAST ONE POLYSILOXANE/POLYUREA BLOCK COPOLYMER

(75) Inventors: Gaëlle Brun, Paris (FR); Sabine Vrignaud, La Plaine Saint-Denis (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 11/976,554

(22) Filed: Oct. 25, 2007

(65) Prior Publication Data

US 2008/0127429 A1 Jun. 5, 2008

Related U.S. Application Data

(60) Provisional application No. 60/861,040, filed on Nov. 27, 2006.

(30) Foreign Application Priority Data

Oct. 25, 2006 (FR) .................. 06 54535

(51) Int. Cl.
*A61Q 5/10* (2006.01)
*C08G 77/00* (2006.01)
(52) U.S. Cl. ............. 8/405; 8/406; 8/407; 8/455; 8/552; 8/581; 8/585; 8/637.1; 528/28; 528/44
(58) Field of Classification Search .............. 8/405, 8/406, 407, 455, 552, 581, 585, 637.1; 528/28, 528/44
See application file for complete search history.

(56) References Cited

U.S. PATENT DOCUMENTS

| | | |
|---|---|---|
| 2,047,398 A | 7/1936 | Voss et al. |
| 2,102,113 A | 12/1937 | Djordjevitch |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,723,248 A | 11/1955 | Wright |
| 2,961,347 A | 11/1960 | Floyd |
| 3,206,462 A | 9/1965 | McCarty |
| 3,227,615 A | 1/1966 | Korden |
| 3,589,578 A | 6/1971 | Kamphausen |
| 3,632,559 A | 1/1972 | Matter et al. |
| 3,734,874 A | 5/1973 | Kibler et al. |
| 3,779,993 A | 12/1973 | Kibler et al. |
| 3,835,081 A | 9/1974 | Remley |
| 3,836,537 A | 9/1974 | Boerwinkle et al. |
| 3,874,870 A | 4/1975 | Green et al. |
| 3,917,817 A | 11/1975 | Vanlerberghe et al. |
| 3,929,990 A | 12/1975 | Green et al. |
| 3,946,749 A | 3/1976 | Papantoniou et al. |
| 3,966,403 A | 6/1976 | Papantoniou et al. |
| 3,966,904 A | 6/1976 | Green et al. |
| 3,975,350 A | 8/1976 | Hudgin et al. |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,424 A | 5/1977 | Fiorentino |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,119,680 A | 10/1978 | Vachon |
| 4,119,682 A | 10/1978 | Kleiner |
| 4,128,631 A | 12/1978 | Lundmark et al. |
| 4,131,576 A | 12/1978 | Iovine et al. |
| 4,137,208 A | 1/1979 | Elliott |
| 4,282,203 A | 8/1981 | Jacquet et al. |
| 4,300,580 A | 11/1981 | O'Neill et al. |
| 4,307,219 A | 12/1981 | Larson |
| 4,349,532 A | 9/1982 | Vanlerberghe et al. |
| 4,381,919 A | 5/1983 | Jacquet et al. |
| 4,514,552 A | 4/1985 | Shay et al. |
| 4,578,266 A | 3/1986 | Tietjen et al. |
| 4,608,250 A | 8/1986 | Jacquet et al. |
| 4,693,935 A | 9/1987 | Mazurek |
| 4,728,571 A | 3/1988 | Clemens et al. |
| 4,742,142 A | 5/1988 | Shimizu et al. |
| 4,743,673 A | 5/1988 | Johnston et al. |
| 4,970,252 A | 11/1990 | Sakuta et al. |
| 4,972,037 A | 11/1990 | Garbe et al. |
| 4,973,656 A | 11/1990 | Blount |
| 4,987,169 A | 1/1991 | Kuwata et al. |
| 5,236,986 A | 8/1993 | Sakuta |
| 5,246,694 A | 9/1993 | Birthwistle |
| 5,266,321 A | 11/1993 | Shukuzaki et al. |
| 5,412,004 A | 5/1995 | Tachibana et al. |
| 5,472,689 A | 12/1995 | Ito |
| 5,538,717 A | 7/1996 | LaPoterie |
| 5,641,835 A | 6/1997 | Smith et al. |
| 5,654,362 A | 8/1997 | Schulz, Jr. et al. |
| 5,660,816 A | 8/1997 | Adams et al. |

(Continued)

FOREIGN PATENT DOCUMENTS

DE          2 330 956          1/1974

(Continued)

OTHER PUBLICATIONS

STIC Search Report dated Dec. 6, 2008.*

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

Disclosed herein is a composition comprising at least one nonionic polysiloxane/polyurea block copolymer, at least one colored or coloring entity, and at least one volatile nonsilicone organic solvent. Such a composition may make it possible to obtain a coloring which is resistant to external agents.

21 Claims, No Drawings

U.S. PATENT DOCUMENTS

| | | | |
|---|---|---|---|
| 5,662,893 | A | 9/1997 | George et al. |
| 5,674,479 | A | 10/1997 | George et al. |
| 5,756,080 | A | 5/1998 | Janchitraponvej et al. |
| 5,760,116 | A | 6/1998 | Kilgour et al. |
| 5,811,487 | A | 9/1998 | Schulz, Jr. et al. |
| 5,837,793 | A | 11/1998 | Harashima et al. |
| 5,849,318 | A | 12/1998 | Imai et al. |
| 5,948,393 | A | 9/1999 | Tomomasa et al. |
| 5,990,479 | A | 11/1999 | Weiss et al. |
| 6,106,577 | A | 8/2000 | Audousset et al. |
| 6,132,704 | A | 10/2000 | Bhatt et al. |
| 6,166,093 | A | 12/2000 | Mougin et al. |
| 6,225,198 | B1 | 5/2001 | Alivisatos et al. |
| 6,274,129 | B1 | 8/2001 | Bhatt et al. |
| 6,372,876 | B1 | 4/2002 | Kim et al. |
| 6,395,265 | B1 * | 5/2002 | Mougin et al. ........... 424/70.12 |
| 6,410,004 | B1 | 6/2002 | Kim et al. |
| 6,864,330 | B2 | 3/2005 | Schneider et al. |
| 7,026,424 | B2 | 4/2006 | Schäfer et al. |
| 7,141,077 | B2 | 11/2006 | Detering et al. |
| 7,217,296 | B2 | 5/2007 | Pastore et al. |
| 2002/0069790 | A1 | 6/2002 | Hayashi et al. |
| 2003/0180245 | A1 | 9/2003 | Gotsche et al. |
| 2003/0199642 | A1 | 10/2003 | Schneider et al. |
| 2003/0235548 | A1 * | 12/2003 | Lu ........................ 424/70.12 |
| 2004/0139559 | A1 | 7/2004 | Detering et al. |
| 2004/0210024 | A1 * | 10/2004 | Schafer et al. ................ 528/44 |
| 2004/0254325 | A1 | 12/2004 | Kuepfer et al. |
| 2005/0147576 | A1 | 7/2005 | Cotton |
| 2007/0141006 | A1 | 6/2007 | Livoreil et al. |

FOREIGN PATENT DOCUMENTS

| | | |
|---|---|---|
| DE | 3 814 536 A | 11/1988 |
| DE | 10 2005 017277 A1 | 4/2006 |
| EP | 0 039 162 A2 | 4/1981 |
| EP | 0 043 974 A2 | 1/1982 |
| EP | 0 080 976 A1 | 6/1983 |
| EP | 0 122 324 A1 | 10/1984 |
| EP | 0 173 109 A2 | 3/1986 |
| EP | 0 295 886 A2 | 12/1988 |
| EP | 0 412 704 A2 | 2/1991 |
| EP | 0 412 707 A1 | 2/1991 |
| EP | 0 524 612 A2 | 1/1993 |
| EP | 0 619 111 A1 | 10/1994 |
| EP | 0 637 600 A1 | 2/1995 |
| EP | 0 640 105 A1 | 3/1995 |
| EP | 0 648 485 A1 | 4/1995 |
| EP | 0 656 021 A1 | 6/1995 |
| EP | 0 751 162 A1 | 1/1997 |
| EP | 0 815 836 A2 | 1/1998 |
| EP | 1 035 144 A2 | 9/2000 |
| EP | 1 184 426 A2 | 3/2002 |
| EP | 1 266 647 A1 | 12/2002 |
| EP | 1 426 035 A1 | 6/2004 |
| EP | 1 649 898 A2 | 4/2006 |
| EP | 1 672 006 A1 | 6/2006 |
| FR | 1 222 944 A | 6/1960 |
| FR | 1 400 366 A | 5/1965 |
| FR | 1 564 110 A | 4/1969 |
| FR | 1 580 545 A | 9/1969 |
| FR | 1 583 363 A | 10/1969 |
| FR | 2 077 143 A | 10/1971 |
| FR | 2 080 759 A1 | 11/1971 |
| FR | 2 162 025 A1 | 7/1973 |
| FR | 2 190 406 A2 | 2/1974 |
| FR | 2 198 719 A1 | 4/1974 |
| FR | 2 252 840 A1 | 6/1975 |
| FR | 2 265 781 A1 | 10/1975 |
| FR | 2 265 782 A1 | 10/1975 |
| FR | 2 270 846 A1 | 12/1975 |
| FR | 2 280 361 A2 | 2/1976 |
| FR | 2 316 271 A1 | 1/1977 |
| FR | 2 320 330 A1 | 3/1977 |
| FR | 2 336 434 A1 | 7/1977 |
| FR | 2 350 384 A1 | 12/1977 |
| FR | 2 357 241 A2 | 2/1978 |
| FR | 2 368 508 A2 | 5/1978 |
| FR | 2 393 573 A1 | 1/1979 |
| FR | 2 413 907 A1 | 8/1979 |
| FR | 2 439 798 A1 | 5/1980 |
| FR | 2 741 530 A1 | 5/1997 |
| FR | 2 743 297 A1 | 7/1997 |
| FR | 2 830 189 A1 | 4/2003 |
| FR | 2 864 784 A1 | 7/2005 |
| FR | 2 872 427 A1 | 1/2006 |
| GB | 839 805 | 6/1960 |
| GB | 922 457 | 4/1963 |
| GB | 1169862 | 11/1969 |
| JP | 61-194009 A | 8/1986 |
| JP | 2003040724 A | 2/2003 |
| LU | 75370 A1 | 2/1978 |
| LU | 75371 A1 | 2/1978 |
| WO | WO 93/23446 A2 | 11/1993 |
| WO | WO 94/03510 A1 | 2/1994 |
| WO | WO 95/00578 A1 | 1/1995 |
| WO | WO 97/20879 A1 | 6/1997 |
| WO | WO 97/23456 A1 | 7/1997 |
| WO | WO 97/25021 A1 | 7/1997 |
| WO | WO 00/40628 A1 | 7/2000 |
| WO | WO 00/71601 A1 | 11/2000 |
| WO | WO 02/15854 A1 | 2/2002 |
| WO | WO 02/095123 A1 | 11/2002 |
| WO | WO 03/014194 A1 | 2/2003 |
| WO | WO 2005/060922 A1 | 7/2005 |
| WO | WO 2005/092274 A1 | 10/2005 |

OTHER PUBLICATIONS

STIC Search Report dated Aug. 13, 2008.*
Dabbousi B.O. et al., "(CdSe)ZnS core-shell quantum dots: synthesis and characterisation of a size series of highly luminescent nanocristallites," J. of Physical Chem. B, vol. 101, pp. 9463-9475 (Nov. 1997).
Feigenbaum, H.N., "Polyethyleneimine Prospective Application," Cosmetics & Toiletries, vol. 108, p. 73 (1993).
English language abstract of DE 10 2005 017277, publ. Apr. 20, 2006.
English language abstract of DE 3 814 536, publ. Nov. 10, 1998.
English language abstract of EP 0 043 974, publ. Jan. 20, 1982.
English language abstract of EP 0 080 976, publ. Jun. 8, 1983.
English language abstract of EP 0 637 600, publ. Feb. 8, 1995.
English language abstract of EP 1 184 426, publ. Mar. 6, 2002.
English language abstract of EP 1 266 647, publ. Dec. 18, 2002.
English language abstract of EP 1 426 035, publ. Jun. 9, 2004.
English language abstract of EP 1 649 898, publ. Apr. 26, 2006.
English language abstract of EP 1 672 006, publ. Jun. 21, 2006.
English language Derwent abstract of FR 1 580 545, publ. Sep. 5, 1969.
English language Derwent abstract of FR 2 077 143, publ. Oct. 15, 1971.
English language Derwent abstract of FR 2 080 759, publ. Nov. 19, 1971.
English language Derwent abstract of FR 2 190 406, publ. Feb. 1, 1974.
English language Derwent abstract of FR 2 198 719, publ. Apr. 5, 1974.
English language Derwent abstract of FR 2 252 840, publ. Jun. 27, 1975.
English language Derwent abstract of FR 2 270 846, publ. Dec. 12, 1975.
English language Derwent abstract of FR 2 336 434, publ. Jul. 22, 1977.
English language abstract of FR 2 368 508, publ. May 19, 1978.

English language abstract of FR 2 393 573, publ. Jan. 5, 1979.
English language abstract of FR 2 872 427, publ. Jan. 6, 2006.
English language abstract of JP 2003 040724, publ. Feb. 13, 2003.
English language abstract of JP 61-194009, publ. Aug. 28, 1986.
English language abstract of WO 00/071601. publ. Nov. 30, 2000.
English language abstract of WO 05/060922, publ. Jul. 7, 2005.
English language abstract of WO 97/20879, publ. Jun. 12, 1997.
English language abstract of WO 97/23456, publ. Jul. 3, 1997.
English language abstract of WO 00/40628, publ. Jul. 13, 2000.
Fonnum, G. et al., "Associative Thickeners. Part I: Synthesis, Rheology, And Aggregation Behavior", Colloid & Polymer Science, vol. 271, No. 4, pp. 380-389 (Apr. 1993).
International Search Report, Rapport De Recherche Preliminaire, FA 685802, FR 0654535 (May 11, 2007).
Shirai, K., "Tautomerism and Fluorescent Properties of Aminovinylpyrazine Dyes," J. of the Soc'Y. of Dyers & Colorists, vol. 114, No. 12, pp. 368-374 (Dec. 1998).
Kenausis, G.L. et al., "Poly(L-lysine)-g-Poly(ethylene glycol) Layers on Metal Oxide Surfaces: Attachment Mehcanism and Effects of Polymer Architecture on Resistance to Protein Adsorption," J. of Physical Chem. B, 104, p. 3298 (2000).
Kim, J. H., "Selective topochemical photoreaction of crystallized 2,3-(phenylethenyl)-4,5-dicyanopyrazine," Chem. Lett., (2), pp. 143-144 (1999).

"Water-soluble Resins," Kirk-Othmer Encyclopedia of Chem. Tech., vol. 20, pp. 214-216 (3d ed. 1982).
Meylan et al., "Atom/Fragment Contribution Method for Estimating Octanol-Water Partition Coefficientm," J. Pharm. Sci., vol. 84, No. 1, pp. 83-92 (1995).
Patel, N. R., "The Synthesis of Pyrazino[2,3-d]pyridazine and Some of its Derivatives," J. of Heterocyclic Chem., vol. 3, No. 4, pp. 512-517 (1966).
Peng et al., "Epitaxial Growth of Highly Luminescent Cdse/Cds Core/Shell Nanocrystals With Photostability and Electronic Accessibility", J. of the Am. Chem. Soc'y, vol. 119, No. 30, pp. 7019-7029 (Jul. 1997).
Petersen, H. et al., "Synthesis, Characterization, and Biocompatibility of Polyethylenimine-graftpoly(ethylene glycol) Block Copolymers," Macromolecules, vol. 35, No. 18, p. 6867 (Aug. 2002).
Schlosser et al.., "Thermoplastic Silicone Elastomers Improve Nail Polish Performance", Cosmetics & Toiletries, vol. 120, No. 7, pp. 59-62 (Jul. 2005).
Schlossman, M. L. "Treated Pigments, New Ways to Impart Color on the Skin," Cosmetics & Toiletries, vol. 105, pp. 53-64 (Feb. 1990).

* cited by examiner ial Appli-
COLORING COMPOSITION OF KERATINOUS FIBERS COMPRISING AT LEAST ONE POLYSILOXANE/POLYUREA BLOCK COPOLYMER This application claims benefit of U.S. Provisional Application No. 60/861,040, filed Nov. 27, 2006, the contents of which are incorporated herein by reference. This application also claims benefit of priority under 35 U.S.C. §119 to French Patent Application No. FR 0654535, filed Oct. 25, 2006, the contents of which are also incorporated herein by reference.

Disclosed herein is a cosmetic composition for the coloring of keratinous fibers comprising at least one polysiloxane/polyurea block copolymer.

It is already known, in the field of the coloring of keratinous fibers, to color keratinous fibers by different techniques using direct dyes and/or pigments for nonpermanent colorings and dye precursors for permanent colorings.

Nonpermanent coloring or direct coloring comprises dyeing keratinous fibers with dyeing compositions comprising direct dyes. These dyes are colored or coloring molecules having an affinity for keratinous fibers. They are applied to keratinous fibers for a time necessary for the desired coloring to be obtained and are then rinsed out.

The direct dyes which are conventionally used include nitrobenzene, anthraquinone, nitropyridine, azo, xanthene, acridine, azine, triarylmethane, and natural dyes.

Some of these dyes can be used under lightening conditions, which makes it possible to obtain visible colorings on dark hair.

It is also known to dye keratinous fibers permanently by oxidation dyeing. This coloring technique comprises applying, to keratinous fibers, a composition comprising dye precursors, such as oxidation bases and couplers. These precursors, under the action of an oxidizing agent, will form at least one color entity in the individual hair.

The variety of the molecules employed as oxidation bases and couplers makes it possible to obtain a rich palette of colors and the colorings which result therefrom are generally permanent, powerful, and/or resistant to external agents, for example, light, bad weather, washing operations, perspiration, and/or rubbing.

In order to be visible on dark hair, these two coloring techniques generally require preliminary or simultaneous bleaching of the keratinous fibers. This bleaching stage, carried out with an oxidizing agent, such as hydrogen peroxide or persalts, often results in not insignificant damage to the keratinous fibers, which in turn detrimentally affects their cosmetic properties. The hair then has a tendency to become rough, more difficult to disentangle, and more brittle.

Another coloring method comprises using pigments. The use of pigments at the surface of keratinous fibers generally makes it possible to obtain visible colorings on dark hair since the surface pigment masks the natural color of the fiber. The use of pigments for coloring keratinous fibers is described, for example, French Patent Application No. 2 741 530, which recommends the use, for the coloring of keratinous fibers, of a composition comprising at least one dispersion of particles of film-forming polymer comprising at least one acid functional group and at least one pigment dispersed in the continuous phase of the dispersion. However, the sheathing obtained is not resistant to shampooing operations.

It is furthermore known to carry out coloring of the hair using a composition comprising a cyanoacrylate and pigments, as described, for example, in European Patent Application No. 1 649 898. However, the sheathing obtained is not entirely satisfactory in the face of external agents, such as a shampoo and perspiration. Furthermore, the sheathing obtained is sensitive to fatty substances, such as sebum.

Moreover, European Patent Application No. 1 266 647 and International Patent Application Publication No. WO 2005/060922 describe compositions intended for making up the lips, eyelashes, or complexion which comprise a polysiloxane copolymer comprising at least one unit capable of forming hydrogen bonds. Mention is made, as an example of units capable of forming hydrogen bonds, inter alia, of polyureas. However, these documents do not envisage the use in the hair field of such a composition for the sheathing of individual hairs.

Thus, it would be desirable to develop a coloring composition for keratinous fibers which makes it possible to obtain a coloring which is resistant to (in other words, remains on the hair despite) one or more of the various attacks to which the hair may be subjected, for example, a coloring which is resistant to shampooing operations and/or perspiration, while retaining the integrity of the keratinous fibers.

Thus, disclosed herein is a coloring composition which comprises at least one nonionic polysiloxane/polyurea block copolymer, at least one colored or coloring entity, and at least one volatile nonsilicone organic solvent.

Further disclosed herein is a method for coloring keratinous fibers, such as the hair, which comprises applying, to the fibers, the composition disclosed herein.

By the use of such a composition, a coloring in varied hues may be obtained on keratinous fibers which is resistant to shampooing operations while retaining the physical qualities of the keratinous fibers. Such a coloring may be resistant to one or more of the external attacks to which the hair may be subjected, such as shampooing operations and/or perspiration.

Furthermore, the colored sheathing thus formed may exist in the form of a homogeneous and smooth deposited layer which has excellent adhesion to hair. The present inventors have found that the hairs colored with the compositions disclosed herein remained completely separate and could be styled without a problem and that the coloring properties introduced into the fiber were resistant to shampooing operations.

The cosmetic composition in accordance with the present disclosure may make it possible to obtain, for example, with colored pigments, colorings which are visible even on dark hair without it being necessary to bleach the keratinous fibers since the colored or coloring entity remaining at the surface makes it possible to mask the natural color of the fiber.

Nonionic Polysiloxane/Polyurea Block Copolymers

In the context of the present disclosure, the copolymer is a nonionic polysiloxane/polyurea copolymer, that is to say that it does not comprise an ionized or ionizable group.

As used herein, the term "block copolymer" is understood to mean a copolymer comprising at least two separate sequences of each of the polymers constituting the copolymer in the backbone of the copolymer. For example, the copolymer of the present disclosure comprises at least one sequence (or block) of polysiloxane and at least one sequence (or block) of polyurea in the backbone of the copolymer.

The copolymer of the present disclosure may, in addition to the polysiloxane/polyurea, comprise other blocks of different polymers. For example, the copolymer may be chosen from polysiloxane/polyurea/polyurethane block copolymers.

According to one embodiment, the copolymer comprises polysiloxane in an amount by weight of greater than 5%, with respect to the total weight of the copolymer. According to another embodiment, the polysiloxane is predominant in the copolymer, for example, present in an amount of greater than 90% by weight, with respect to the total weight of the copolymer.

According to yet another embodiment, the copolymer comprises solely at least one siloxane block and at least one polyurea block.

According to one embodiment, the copolymer may be chosen from compounds of formula (I):

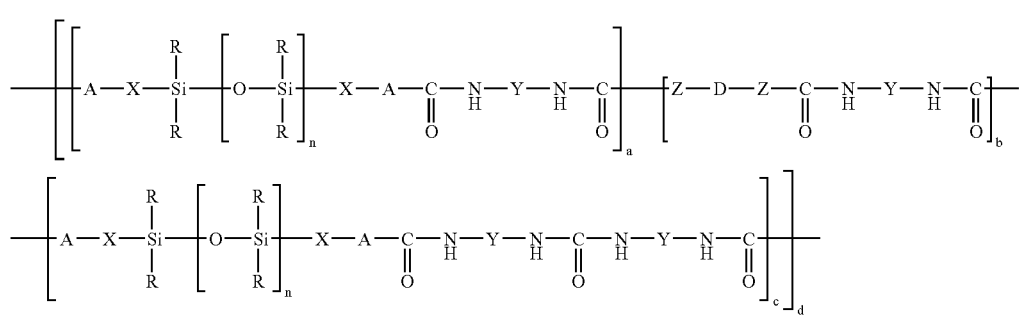

wherein:
R is chosen from monovalent hydrocarbon radicals, optionally substituted by at least one radical chosen from fluorine and chlorine, and comprising from 1 to 20 carbon atoms,
X is chosen from alkylene radicals comprising from 1 to 20 carbon atoms, wherein nonneighboring methylene units may be optionally replaced by —O— radicals,
A is chosen from oxygen and amino radicals —NR'—,
Z is chosen from oxygen and amino radicals —NR'—,
R' is chosen from hydrogen and alkyl radicals comprising from 1 to 10 carbon atoms,
Y is chosen from divalent hydrocarbon radicals, optionally substituted by at least one radical chosen from fluorine and chlorine, and comprising from 1 to 20 carbon atoms,
D is chosen from alkylene radicals, optionally substituted by at least one radical chosen from fluorine, chlorine, $C_1$-$C_6$ alkyl, and $C_1$-$C_6$ alkyl ester radicals, and comprising from 1 to 700 carbon atoms, wherein nonneighboring methylene units maybe optionally replaced by at least one radical chosen from —O—, —COO—, —OCO—, and —OCOO— radicals,
n is a number ranging from 1 to 4000,
a is a number greater than or equal to 1,
b is a number ranging from 0 to 40,
c is a number ranging from 0 to 30, and
d is a number greater than 0, provided that, in at least one of the units (a), A is an NH radical.

According to at least one embodiment, R is chosen from monovalent hydrocarbon radicals comprising from 1 to 6 carbon atoms, for example, methyl, ethyl, vinyl, and phenyl. According to another embodiment, R is an unsubstituted alkyl radical.

In at least one embodiment, X is chosen from alkylene radicals comprising from 2 to 10 carbon atoms. In a further embodiment, the alkylene radical X is not interrupted.

According to at least one embodiment, the A group in all the units (b) and (c), when they are present, is NH. According to another embodiment, all the A groups are NH radicals.

In at least one embodiment, Z is chosen from oxygen and NH radicals.

According to at least one embodiment, Y is chosen from hydrocarbon radicals comprising from 3 to 13 carbon atoms which, in at least one embodiment, are unsubstituted. In a further embodiment, Y is chosen from aralkylene radicals and alkylene radical which may be linear or cyclic.

According to one embodiment, D is chosen from alkylene radicals comprising at least 2, for example, at least 4, carbon atoms, and no more than 12 carbon atoms.

In another embodiment, D is chosen from polyoxyalkylene radicals, such as polyoxyethylene and polyoxypropylene radicals, with at least 20, for example, at least 100, carbon atoms and no more than 800, for instance, no more than 200, carbon atoms.

According to yet another embodiment, the radical D is unsubstituted.

In at least one embodiment, n is a number greater than or equal to 3, for example, greater than or equal to 25, and, in at least one embodiment, no more than 800, for instance, no more than 400, or no more than 250.

In at least one embodiment, a is a number greater than 50.

When b is other than 0, in at least one embodiment, b may be a number less than or equal to 500, for example, less than or equal to 25.

According to another embodiment, c is a number less than or equal to 10, for example, less than or equal to 5.

The copolymers of the present disclosure may be obtained according to the polymerization processes described, for example, in U.S. Patent Application Publication No. 2004/0254325 and International Patent Application Publication No. WO 03/014194.

The copolymer can thus be obtained by a two-stage process, such that:
in a first stage, a silazane chosen from compounds of formulas (2) and (2'):

wherein m is a number ranging from 1 to 4000, and W is chosen from hydrogen, substituted and unsubstituted hydrocarbon radicals comprising, for example, from 1 to 20 carbon atoms, and $R_2Si$—X—$NH_2$ radicals;

is reacted with an organic silicon compound of formula (3):

$$(HO)(R_2SiO)_{n-1}[H] \tag{3}$$

in order to obtain an aminoalkylpolydiorganosiloxane of formula (4):

$$H_2N\text{—}X\text{—}[SiR_2O]_nSiR_2\text{—}X\text{—}NH_2 \tag{4}$$

in a second stage, the aminoalkylpolydiorganosiloxane of formula (4) is polymerized with a diisocyanate of formula (5):

$$OCN\text{—}Y\text{—}NCO \tag{5}$$

Generally, in a first stage, the silazane chosen from compounds of formulas (2) and (2') and the reactants comprising silanol groups may be employed in equimolar ratios.

For the preparation of the very pure silicones comprising a bisaminoalkyl ending of the formula (4), use may be made of a small excess of the silazane compound chosen from compounds of formulas (2) and (2'), which can subsequently be removed in a simple additional process stage, such as, for example, the addition of small amounts of water.

If b is at least 1, use may be made, during the second stage, of up to 95% by weight, on the basis of all the components employed, of at least one chain-extending agent, chosen, for example, from diamines, hydroxyl compounds masked by an isocyanate, dihydroxyl compounds, and mixtures thereof.

In one embodiment, the at least one chain-extending agent may be chosen from compounds of formula (6):

$$HZ\text{-}D\text{-}ZH \tag{6}$$

wherein D and Z are defined above. If Z is O, the at least one chain-extending agent of formula (6) can also be reacted, before the reaction in the second stage, with a diisocyanate of formula (5). If appropriate, water can be employed as a chain-extending agent.

Examples of diisocyanates of formula (5) include, but are not limited to aliphatic compounds, such as isophorone diisocyanate, 1,6-hexamethylene diisocyanate, 1,4-tetramethylene diisocyanate, and 4,4'-methylenedicyclohexyl diisocyanate, and aromatic compounds, such as 4,4'-methylenediphenyl diisocyanate, 2,4-toluene diisocyanate, 2,5-toluene diisocyanate, 2,6-toluene diisocyanate, m-phenylene diisocyanate, p-phenylene diisocyanate, m-xylene diisocyanate, tetramethyl-m-xylene diisocyanate, and mixtures of these isocyanates. A non-limiting example of a commercially available compound is a diisocyanate of the Desmodur® series (H, I, M, T, W) from Bayer AG, Germany. In at least one embodiment, the diisocyanate is chosen from aliphatic diisocyanates in which Y is an alkylene radical because these diisocyanates may result in materials which exhibit improved stabilities towards UV radiation.

The alkylenes comprising an α,ω-OH ending of formula (6) may be chosen, for example, from polyalkylenes and polyoxyalkylenes. In at least one embodiment, these alkylenes are essentially devoid of contamination by monofunctional polyoxyalkylenes, trifunctional polyoxyalkylenes, and polyoxyalkylenes of higher functionality. Use may also be made of polyether polyols, polytetramethylene diols, polyester polyols, and polycaprolactone diols and also polyalkylenes comprising an α,ω-OH ending based on poly(vinyl acetate), poly(vinyl acetate)/ethylene copolymers, poly(vinyl chloride) copolymers, and polyisobutylene diols. According to one embodiment, the alkylenes are chosen from polyoxyalkylenes, such as polypropylene glycol. Such compounds are available commercially as base materials, inter alia, for polyurethane foams and for uses as coatings with molecular weights Mn of up to 10 000. Non-limiting examples include the Baycoll® polyether polyols and polyester polyols from Bayer AG, Germany, and the Acclaim® polyether polyols from Lyondell Inc., USA. Use may also be made of α,ω-alkylene diol monomers, such as ethylene glycol, propanediol, butanediol, and hexanediol. As used herein, the term "dihydroxylated compounds" is understood to mean bishydroxyalkylsilicones, such as those supplied, for example, by Goldschmidt under the names Tegomer H-Si 2111, 2311, and 2711.

The preparation of the copolymers described above in formula (I) can be carried out in solution but also in a solid form, continuously or batchwise.

If the amount of urethane or urea segments is large, a solvent having high solubility parameter, such as, for example, dimethylacetamide, may be chosen. Use may also be made of THF. According to one embodiment, the synthesis of the copolymer may be carried out without solvent.

In another embodiment, the synthesis is carried out in the absence of moisture and under a protective gas, such as nitrogen and argon.

According to a further embodiment, the reaction is carried out in the presence of a catalyst. The catalysts appropriate for the preparation include, by way of non-limiting example, dialkyltin compounds, such as dibutyltin dilaurate and dibutyltin diacetate, and tertiary amines, such as N,N-dimethylcyclohexaneamine, 2-dimethylaminoethanol, and 4-dimethylaminopyridine.

According to another embodiment, the copolymer of the present disclosure does not comprise polyurethane.

A non-limiting example of a suitable copolymer is dimethylpolysiloxane/urea, with the INCI name polyureadimethicone.

Such a polymer can be obtained, for example, by copolymerization of an α,ω-aminosilicone with a diisocyanate. Polymers corresponding to these characteristics include, for example, the products sold under the references Wacker-Belsil® UD 60, Wacker-Belsil® UD 80, Wacker-Belsil® UD 140, and Wacker-Belsil® UD 200 by Wacker.

Volatile Nonsilicone Organic Solvents

According to the present disclosure, the composition applied to the hair comprises at least one volatile nonsilicone organic solvent. As used herein, the term "volatile solvent" is understood to mean an organic compound which is liquid at ambient temperature (20° C.) and at atmospheric pressure and which exhibits a vapor pressure at 20° C. of greater than 0.1 mmHg, for example, ranging from 0.1 to 300 mmHg, or from 0.5 to 200 mmHg.

Non-limiting examples of volatile nonsilicone organic solvents include:
  volatile $C_1$-$C_4$ alkanols, such as ethanol and isopropanol;
  volatile $C_5$-$C_7$ alkanes, such as n-pentane, hexane, cyclopentane, 2,3-dimethylbutane, 2,2-dimethyl-butane, 2-methylpentane, and 3-methylpentane;
  esters of liquid $C_1$-$C_{20}$ acids and of volatile $C_1$-$C_8$ alcohols, such as methyl acetate, n-butyl acetate, ethyl acetate, propyl acetate, isopentyl acetate, and ethyl 3-ethoxypropionate;
  ketones which are liquid at ambient temperature and volatile, such as methyl ethyl ketone, methyl isobutyl ketone, diisobutyl ketone, isophorone, cyclohexanone, and acetone;
  volatile polyols, such as propylene glycol;

volatile ethers, such as dimethoxymethane, diethoxyethane, and diethyl ether;

volatile glycol ethers, such as 2-butoxyethanol, butyl diglycol, diethylene glycol monomethyl ether, propylene glycol n-butyl ether, and propylene glycol monomethyl ether acetate;

volatile hydrocarbon oils, such as volatile hydrocarbon oils comprising from 8 to 16 carbon atoms and mixtures thereof, for example, branched $C_8$-$C_{16}$ alkanes, such as $C_8$-$C_{16}$ isoalkanes (also known as isoparaffins), isododecane, isodecane, and, for example, the oils sold under the Isopar and Permethyl trade names, and mixtures thereof. Isohexyl neopentanoates and isodecyl neopentanoate may also be used.

volatile $C_4$-$C_{10}$ perfluoroalkanes, such as dodecafluoropentane, tetradecafluorohexane, and decafluoropentane;

volatile perfluorocycloalkanes, such as perfluoro-methylcyclopentane, 1,3-perfluorodimethylcyclo-hexane and perfluorodecalin, sold respectively under the names of "Flutec PC1®", "Flutec PC3®", and "Flutec PC6®" by F2 Chemicals, and also perfluorodimethylcyclobutane and perfluoromorpholine; and volatile fluoroalkyl and heterofluoroalkyl compounds chosen from compounds of the following formula:

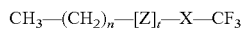

wherein t is equal to 0 or 1; n is an integer ranging from 0 to 3; X is a linear or branched divalent perfluoroalkyl radical comprising from 2 to 5 carbon atoms, and Z is chosen from O, S, and NR, R being chosen from hydrogen and —$(CH_2)_n$—$CH_3$ or —$(CF_2)_m$—$CF_3$ radicals, and m being an integer ranging from 2 to 5.

Examples of such volatile fluoroalkyl and heterofluoroalkyl compounds include, but are not limited to, the methoxynonafluorobutane sold under the name of "MSX 4518®" and "HFE-7100" by 3M and the ethoxynona-fluorobutane sold under the name of "HFE-7200®" by 3M.

According to one embodiment, the solvent is chosen so that its boiling point is less than 200° C.

In another embodiment, the at least one volatile nonsilicone organic solvent is chosen from ethanol, isopropanol, acetone, and isododecane.

The at least one volatile nonsilicone organic solvent may be present in the composition according to the present disclosure in an amount ranging from 0.1% to 90% by weight, relative to the total weight of the composition, for example, from 1% to 80% by weight, or from 5% to 70% by weight.

Colored and Coloring Entities

The composition of the present disclosure comprises at least one colored or coloring entity, such as colored pigments, hydrophilic and hydrophobic direct dyes, and dye precursors. The colored pigments and the direct dyes may or may not be fluorescent.

As used herein, the term "colored entity" is understood to mean a compound which is colored in the dry state or in solution, that is to say, which absorbs at a wavelength ranging from 250 to 750 nm and/or which re-emits, by excitation, visible light. As used herein, the term "coloring entity" is understood to mean an uncolored entity which generates at least one colored compound by interaction with a reactive agent, such as an oxidizing agent.

Colored Entities

Examples of suitable hydrophilic dyes include, but are not limited to, dyes exhibiting a hydrophilicity defined by the logP value of less than or equal to 2. As used herein, the logP value conventionally represents the partition coefficient of the dye between octanol and water. The logP value can be calculated, for example, according to the method described in the paper by Meylan and Howard, "Atom/fragment contribution method for estimating octanol-water partition coefficient", J. Pharm. Sci., 1995, 84, pp. 83-92. This value can also be calculated from numerous commercially available softwares which determine the logP value as a function of the structure of a molecule, for example, the Epiwin software of the US EPA.

According to one embodiment, the logP of the hydrophilic dyes of the composition of the present disclosure is less than 2.

Non-limiting examples of such hydrophilic dyes include neutral, acidic, and cationic nitrobenzene direct dyes; neutral, acidic, and cationic azo direct dyes; neutral, acidic, and cationic quinone, for example, anthraquinone direct dyes; azine direct dyes; triaryl-methane direct dyes; indoamine direct dyes, and natural direct dyes.

Thus, the direct dyes can be chosen as a function of the logP value, for example, from the following direct dyes:

| STRUCTURE | NAME | log P |
|---|---|---|
| ![4-nitro-o-phenylenediamine structure] | 4-nitro-o-phenylenediamine | 0.88 |
| ![2-nitro-p-phenylenediamine structure] | 2-nitro-p-phenylenediamine | 0.53 |

| STRUCTURE | NAME | log P |
|---|---|---|
| picramic acid structure | picramic acid | 0.93 |
| HC Red 13 structure | HC Red 13 | 0.66 |
| N,N'-bis-(2-hydroxyethyl)-2-nitro-p-phenylenediamine structure | N,N'-bis-(2-hydroxyethyl)-2-nitro-p-phenylenediamine | −0.44 |
| HC Red 7 structure | HC Red 7 | 0.13 |
| HC Blue 2 structure | HC Blue 2 | −0.32 |
| HC Yellow 4 structure | HC Yellow 4 | 0.56 |
| HC Yellow 2 structure | HC Yellow 2 | 1.05 |

-continued

| STRUCTURE | NAME | log P |
|---|---|---|
| 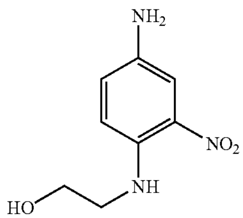 | HC Red 3 | −0.42 |
| 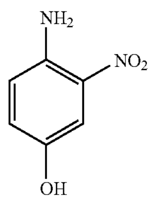 | 4-amino-3-nitrophenol | 1.19 |
| 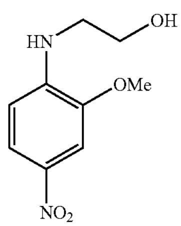 | 1-hydroxyethylamino-5-nitroanisole | 1.13 |
| 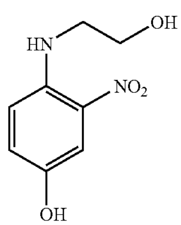 | 3-nitro-p-(hydroxyethylamino)phenol | 0.21 |
| 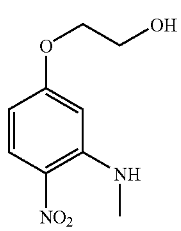 | 3-methylamino-4-nitrophenoxyethanol | 1.13 |
| 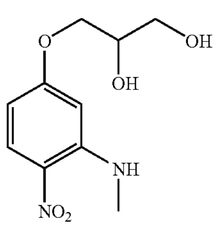 | 2-nitro-5-(glyceryl)methylaniline | 0.89 |
| 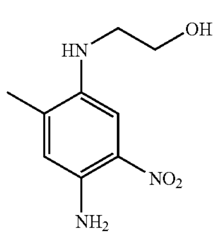 | HC Violet 1 | 0.67 |

-continued

| STRUCTURE | NAME | log P |
|---|---|---|
| 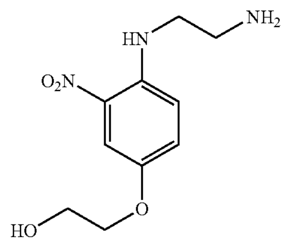 | HC Orange 2 | 0.15 |
| 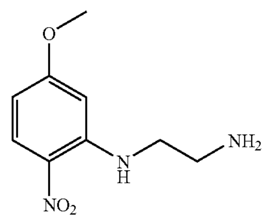 | HC Yellow 9 | 1.12 |
| 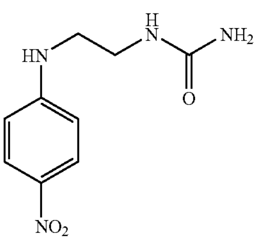 | 4-nitrophenylaminoethylurea | 0.59 |
| | HC Red 10 and HC Red 11 | 0.13 |
| 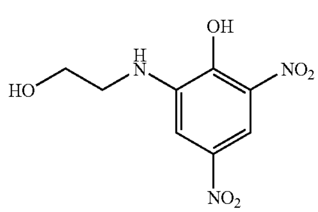 | 2-hydroxyethylpicramic acid | 0.38 |
| 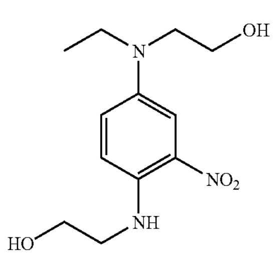 | HC Blue 12 | 1.15 |

| STRUCTURE | NAME | log P |
|---|---|---|
| (structure) | 3-nitro-4-(N-(β-hydroxyethyl)amino) toluene | 1.59 |
| (structure) | 2-(N-(β-methoxyethyl)amino)-5-(N,N-bis(hydroxyethyl)amino)nitrobenzene | 0.38 |
| (structure) | HC Yellow 10 | 0.20 |
| (structure) | HC Violet 2 | 0.17 |
| (structure) | 2-amino-6-chloro-4-nitrophenol | 1.53 |
| (structure) | 4-hydroxypropylamino-3-nitrophenol | 0.70 |
| (structure) | 2,6-diamino-3-((pyridine-3-yl)-azo)pyridine | 1.58 |

-continued
| STRUCTURE | NAME | log P |
|---|---|---|
| 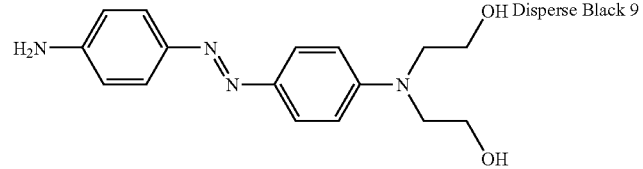 | Disperse Black 9 | 1.83 |
| 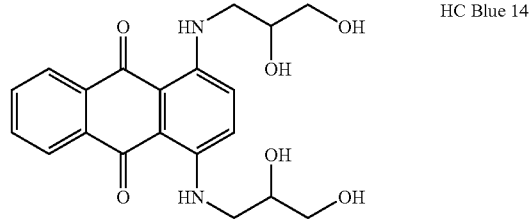 | HC Blue 14 | 0.62 |
The composition of the present disclosure may also comprise hydrophobic dyes. As used herein, hydrophobicity is defined by the logP value, which is greater than 2.
Examples of suitable hydrophobic dyes include, but are not limited to:
| Dye | Chemical structure | log P |
|---|---|---|
| Solvent Black 3 | 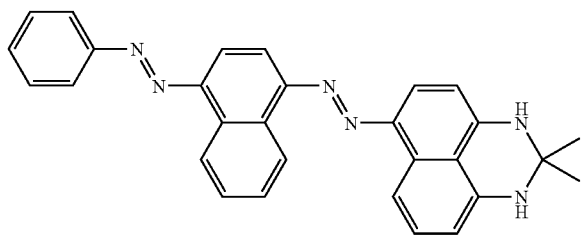 | 8.81 |
| Solvent Blue 104 | 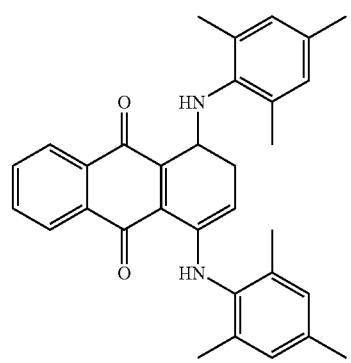 | 8.26 |
| Disperse Blue 134 | 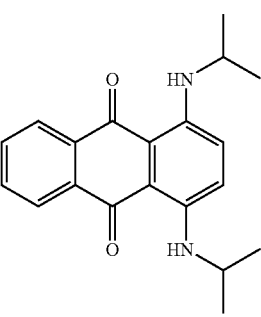 | 6.07 |

-continued
| Dye | Chemical structure | log P |
|---|---|---|
| Solvent Blue 14 | 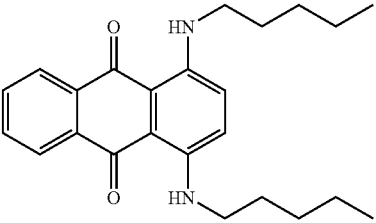 | 8.18 |
| Disperse Blue 14 | 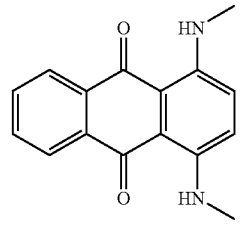 | 4.25 |
| Solvent Red 2 | 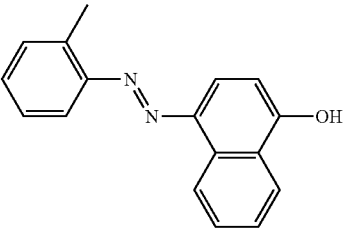 | 5.35 |
| Solvent Brown 5 | 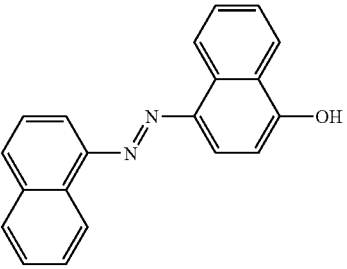 | 5.98 |
| Solvent Green 5 | 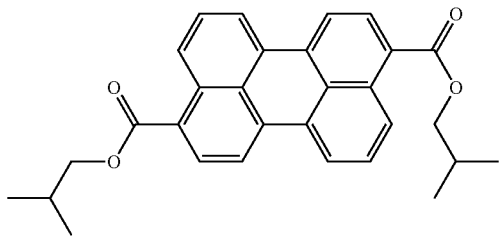 | 8.55 |
| Solvent Orange 2 | 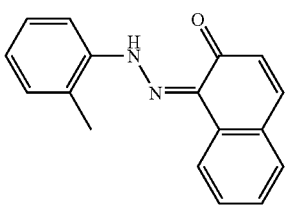 | 3.86 |
| Solvent Orange 1 | 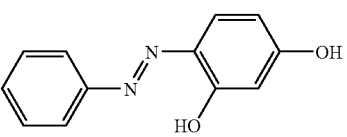 | 3.85 |

-continued
| Dye | Chemical structure | log P |
|---|---|---|
| Disperse Orange 24 | 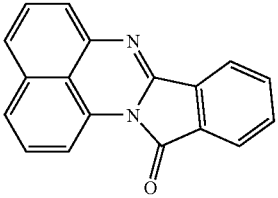 | 3.21 |
| Solvent Orange 63 | 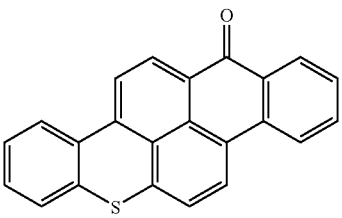 | 7.02 |
| Solvent Red 49 | 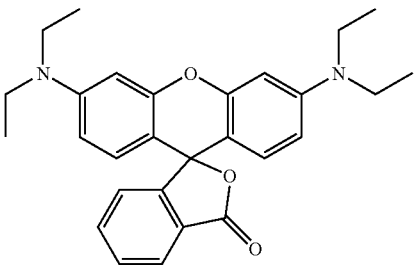 | 6.63 |
| Solvent Red 1 | 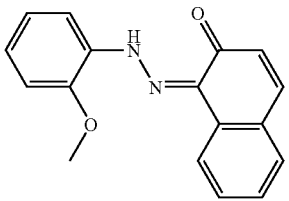 | 3.39 |
| Solvent Red 26 | 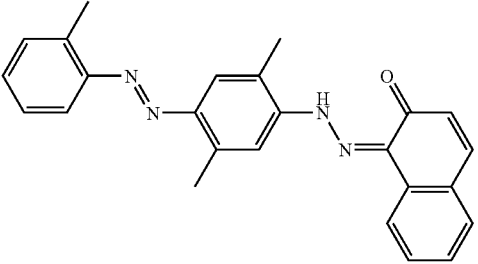 | 7.07 |
| Solvent Red 27 | 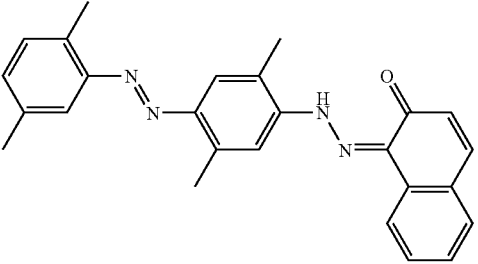 | 7.62 |

-continued

| Dye | Chemical structure | log P |
|---|---|---|
| Solvent Red 18 | 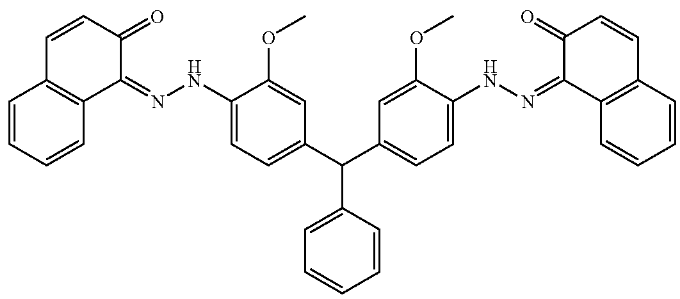 | 8.16 |
| Solvent Red 23 | 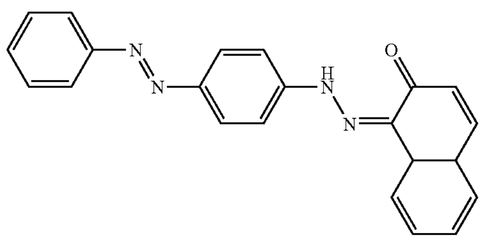 | 5.58 |
| Solvent Red 4 | 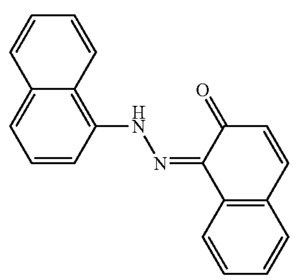 | 4.48 |
| Solvent Orange 7 | 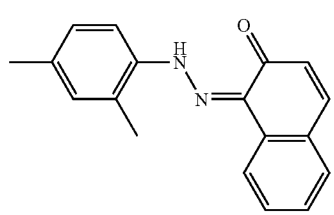 | 4.40 |
| Disperse Blue 72 | 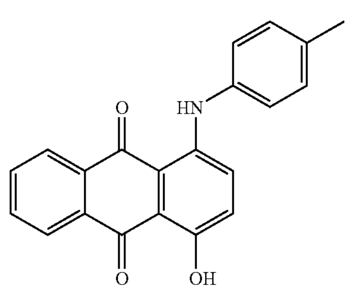 | 6.24 |

-continued

| Dye | Chemical structure | log P |
|---|---|---|
| Disperse Violet 26 | 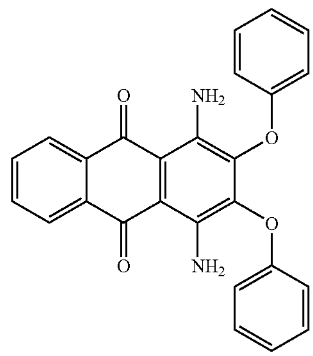 | 5.19 |
| Disperse Yellow 16 | 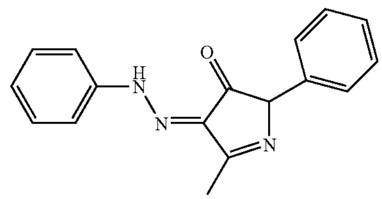 | 3.89 |
| Disperse Yellow 82 | 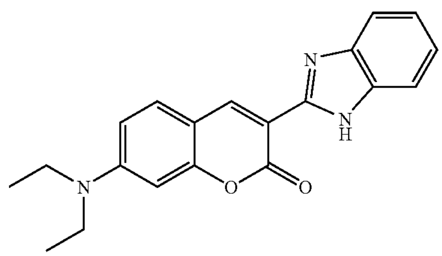 | 3.68 |
| Disperse Yellow 54 | 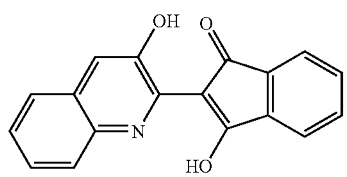 | 4.76 |
| Solvent Yellow 29 | 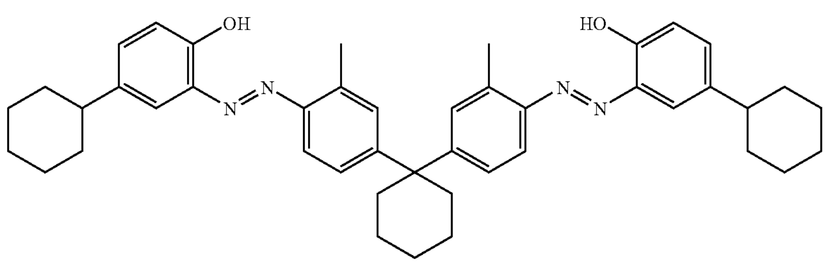 | 17.37 |
| Solvent Yellow 163 | 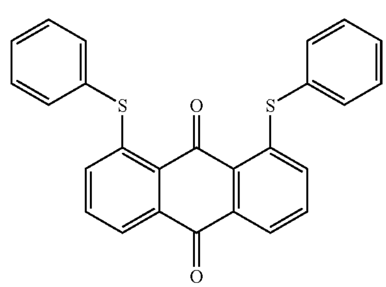 | 7.94 |

-continued

| Dye | Chemical structure | log P |
|---|---|---|
| Solvent Yellow 3 | 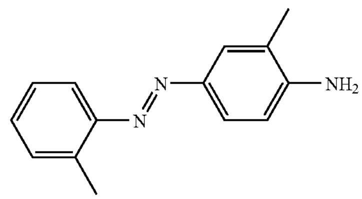 | 4.29 |
| Solvent Yellow 56 | 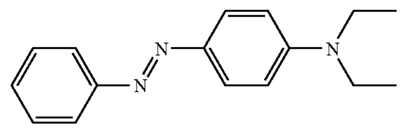 | 5.27 |
| Solvent Yellow 18 | 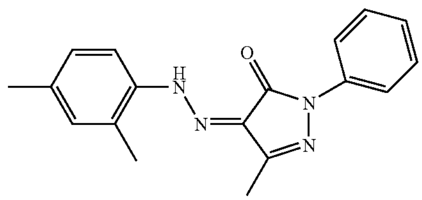 | 4.98 |
| Solvent Yellow 98 | 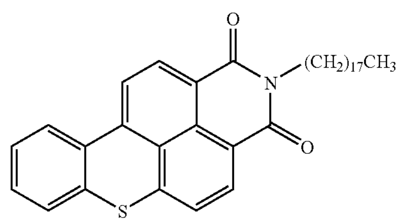 | 4.5 |
| Solvent Yellow 12 | 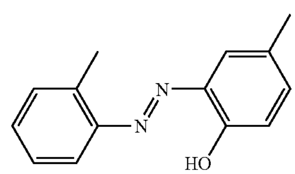 | 5.43 |
| Solvent Yellow 14 | 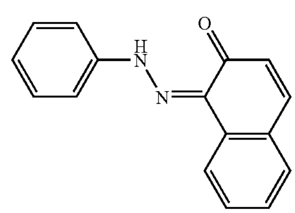 | 3.31 |
| Disperse Red 13 | 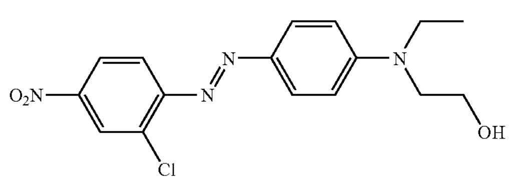 | 5.22 |
| Disperse Green 9 | 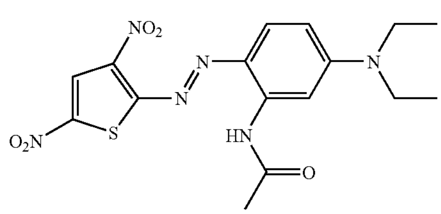 | 4.23 |

-continued

| Dye | Chemical structure | log P |
|---|---|---|
| Disperse Blue 148 | 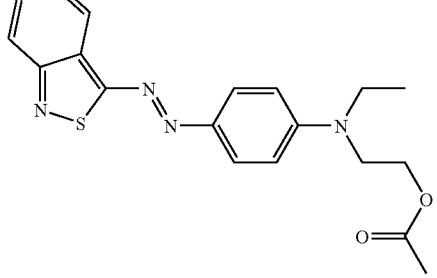 | 4.81 |
| Disperse Violet 63 | 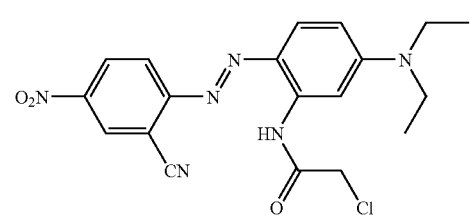 | 5.30 |
| Disperse Blue 60 | 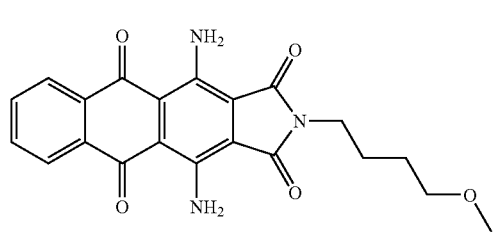 | 3.38 |
| Solvent Orange 15 | 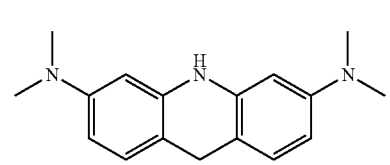 | 3.90 |

According to at least one embodiment, the hydrophobic dyes have a logP of greater than 4, for example, greater than 6.

The use of fluorescent dyes may make it possible to obtain, on dark hair, colorings which are more visible than with conventional hydrophilic or hydrophobic direct dyes. Furthermore, these fluorescent dyes, when applied to dark hair, may also make it possible to lighten the hair without damaging it. This technique, described, for example, in French Patent No. 2 830 189, may make it possible to preserve the quality of the keratinous fiber during the treatment, but the fluorescent dyes employed do not exhibit good resistance to shampooing operations. The presence of the PDMS/polyurea copolymer may make it possible to improve this resistance to shampooing operations.

As used herein, the term "fluorescent compound" is understood to mean fluorescent dyes and optical brighteners. In at least one embodiment, these fluorescent compounds are soluble in the medium of the composition.

Fluorescent dyes are fluorescent compounds which absorb visible radiation, for example, wavelengths ranging from 400 to 800 nm, and which are capable of re-emitting light in the visible region at a higher wavelength. By definition, these dyes are colored entities since they absorb visible light.

According to one embodiment, the fluorescent dyes useful in the context of the present disclosure re-emit orange-colored fluorescent light. They exhibit, for instance, a maximum re-emission wavelength ranging from 500 to 700 nm.

Non-limiting examples of fluorescent dyes include compounds known in the art, for example, those described in Ullmann's Encyclopedia of Industrial Chemistry, Release 2004, 7th edition, "Fluorescent Dyes" chapter.

The optical brighteners of the present disclosure, also known under the name of "brighteners", or "fluorescent brighteners", or "fluorescent brightening agents" or "FWA", or "fluorescent whitening agents", or "whiteners", or "fluorescent whiteners", are colorless transparent compounds as they do not absorb in visible light but only in ultraviolet light (wavelengths ranging from 200 to 400 nanometers) and convert the energy absorbed into fluorescent light of higher wavelength emitted in the visible part of the spectrum, generally in the blue and/or green, that is to say in wavelengths ranging from 400 to 550 nanometers.

Optical brighteners are known in the art, for example, they are described in Ullmann's Encyclopedia of Industrial Chemistry (2002), "Optical Brighteners" and Kirk-Othmer Encyclopedia of Chemical Technology (1995): "Fluorescent Whitening Agents".

The fluorescent dyes which can be used in the composition of the present disclosure include compounds known from the art, for example, those described in French Patent No. 2 830 189. Non-limiting examples of suitable fluorescent dyes include:

Photosensitizing Dye NK-557, sold by Ubichem, of the following structure:

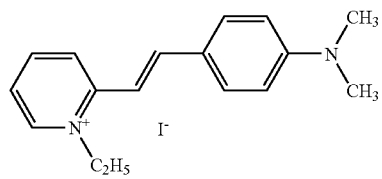

2-[2-(4-(dimethylamino)phenyl)ethenyl]-1-ethylpyridinium iodide

Brilliant Yellow B6GL, sold by Sandoz, of the following structure:

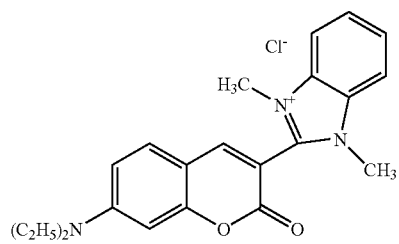

Basic Yellow 2 or Auramine O, sold by Prolabo, Aldrich, and Carlo Erba, of the following structure:

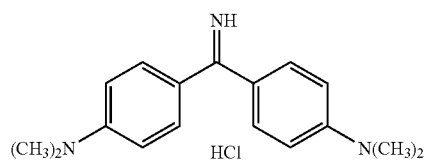

4,4'-(imidocarbonyl)bis(N,N-dimethylaniline) monohydrochloride

Further examples of optical brighteners and fluorescent dyes useful in the present disclosure include, but are not limited to:

Naphthalimides, for example, the following compound:

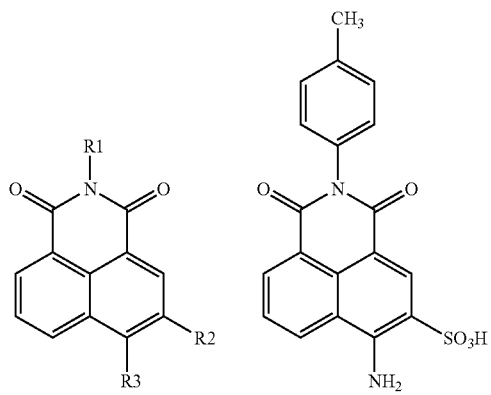

Brilliant Sulphoflavin FF, C.I. 56205 wherein R1, R2, and R3, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$) alkylamino groups; ($C_1$-$C_6$)alkoxy groups; ($C_1$-$C_6$) alkoxycarbonyl groups; carboxy($C_1$-$C_6$)alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups, and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched and cyclic $C_1$-$C_6$ alkoxy, optionally substituted aryl, carboxyl, and sulpho groups and halogen atoms, it being possible for this alkyl radical to be interrupted by at least one heteroatom, such as N, S, and O; wherein the R1, R2, and R3 substituents can form, together with the carbon atoms to which they are attached, a ring chosen from $C_6$-$C_{30}$ aromatic and non-aromatic rings and heterocyclic ring comprising, in total, from 5 to 30 ring members and from 1 to 5 heteroatoms; these rings being fused or nonfused, optionally comprising a carbonyl group, and being optionally substituted by at least one group chosen from $C_1$-$C_4$ alkyl, ($C_1$-$C_4$)alkoxy($C_1$-$C_4$)alkyl, amino, di($C_1$-$C_4$) alkylamino, halogen, phenyl, carboxyl, and tri($C_1$-$C_4$) alkylammonio($C_1$-$C_4$)alkyl groups.

Coumarin derivatives, such as compounds chosen from the following formulas:

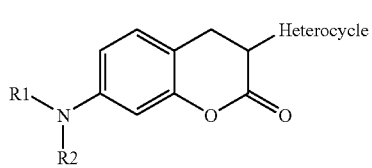

-continued

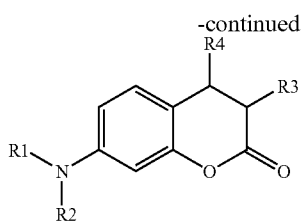

wherein the heterocycle is chosen from furan, thiophene, 2H-pyrrole, 2-pyrroline, pyrrolidine, 1,3-dioxolane, oxazole, thiazole, imidazole, 2-imidazoline, imidazoline, pyrazole, 2-pyrazoline, pyrazolidine, isoxazole, isothiazole, 1,2,3-oxadiazole, 1,2,3-triazole, 1,3,4-thiadiazole, 2H-pyran, 4H-pyran, pyridine, piperidine, 1,4-dioxane, morpholine, 1,4-dithiane, thiomorpholine, pyridazine, pyrimidine, pyrazine, piperazine, 1,3,5-triazine, 1,3,5-trithiane, indolizine, indole, isoindole, 3H-indole, indoline, benzo[b]furan, benzo[b]thiophene, 1H-indazole, benzimidazole, benzothiazole, purine, 4H-quinolizine, quinoline, isoquinoline, cinnoline, phthalazine, quinazoline, quinoxaline, 1,8-naphthyridine, pteridine, quinuclidine, carbazole, acridine, phenazine, phenothiazine, phenoxazine, indene, naphthalene, azulene, fluorene, anthracene, norbornane, and adamantane, and wherein R1, R2, R3, and R4, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy-($C_1$-$C_6$)alkylamino groups; ($C_1$-$C_6$) alkylhydroxy($C_1$-$C_6$)alkylamino groups; ($C_1$-$C_6$) alkoxy groups; ($C_1$-$C_6$)alkoxycarbonyl groups; carboxy ($C_1$-$C_6$)alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, such as from 1 to 6 carbon atoms, optionally substituted by at least one group chosen from hydroxyl, amino, linear, branched and cyclic $C_1$-$C_6$ alkoxy, optionally substituted aryl, carboxyl, and sulpho groups and halogen atoms, it being possible for these alkyl radicals to be interrupted by at least one heteroatom, such as nitrogen, sulphur, and oxygen; wherein the R1, R2, R3, and R4 substituents can form, together with the carbon atoms to which they are attached, a ring chosen from $C_6$-$C_{30}$ aromatic and nonaromatic rings and heterocyclic rings comprising, in total, from 5 to 30 ring members and from 1 to 5 heteroatoms; these rings being fused or nonfused, optionally comprising a carbonyl group, and being optionally substituted by at least one group chosen from $C_1$-$C_4$ alkyl, ($C_1$-$C_4$)alkoxy($C_1$-$C_4$) alkyl, amino, di($C_1$-$C_4$)alkylamino, halogen, phenyl, carboxyl, and tri($C_1$-$C_4$)alkylammonio($C_1$-$C_4$)alkyl groups; or alternatively, two of the R3 and R4 substituents can form, together with the carbon atoms to which they are attached, a ring chosen from $C_6$-$C_{30}$ aromatic rings and heterocyclic rings comprising, in total, from 5 to 30 ring members and from 1 to 5 heteroatoms; this ring being fused or nonfused, this ring and the possible fused ring being optionally substituted by at least one group chosen from $C_1$-$C_4$ alkyl, ($C_1$-$C_4$)alkoxy($C_1$-$C_4$)alkyl, amino, di($C_1$-$C_4$)alkylamino, halogen, phenyl, carboxyl, and tri($C_1$-$C_4$)alkylammonio($C_1$-$C_4$)alkyl groups.

Non-limiting examples of coumarin derivatives include:

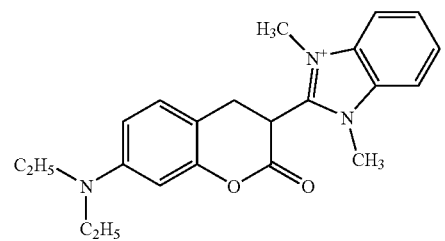

C.I. Basic Yellow 40

Xanthene derivatives, such as:

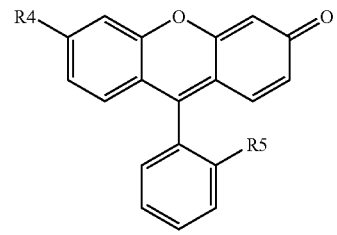

wherein R4 and R5, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups;

dihydroxy($C_1$-$C_6$)alkylamino groups; ($C_1$-$C_6$)alkylhydroxy ($C_1$-$C_6$)alkylamino groups; ($C_1$-$C_6$)alkoxy groups; ($C_1$-$C_6$) alkoxycarbonyl groups; carboxy($C_1$-$C_6$)alkoxy groups; piperidinosulphonyl groups; pyrrolidino groups; ($C_1$-$C_6$) alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched, and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen.

Rhodamines, such as:

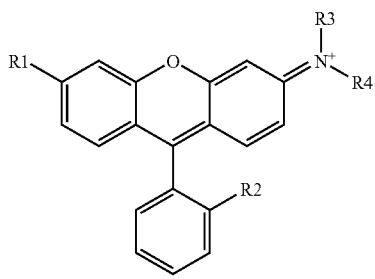

wherein R1, R2, R3, and R4 are defined above. Another non-limiting example of a rhodamine derivative useful herein is:

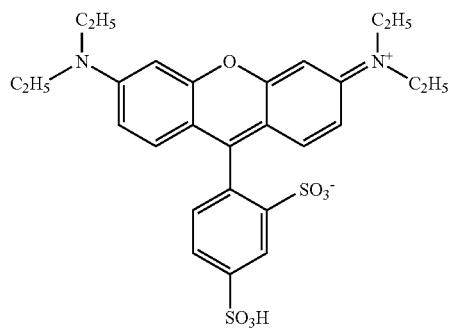

Sulphorhodamine B C.I. 45100 Acid Red 52

Thioxanthene derivatives, such as:

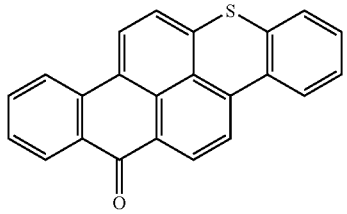

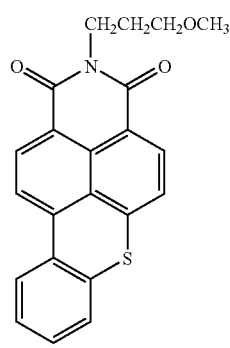

Samaron, Brilliant Yellow H6GL, C.I. 56235 Disperse Yellow 105

Naphtholactam derivatives, such as:

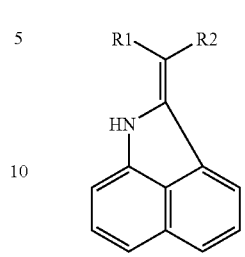

wherein R1 and R2 are defined above.

A non-limiting example of a naphtholactam derivative is:

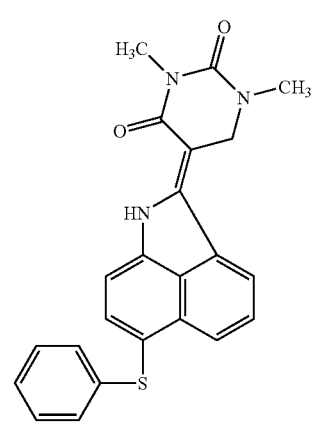

Disperse Dye 28

Azalactone derivatives:

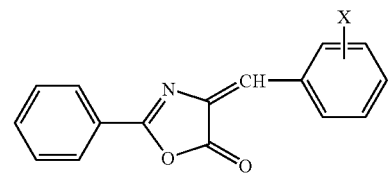

wherein X has the same definition as given for R1 described above.

A non-limiting example of an azalactone derivative is:

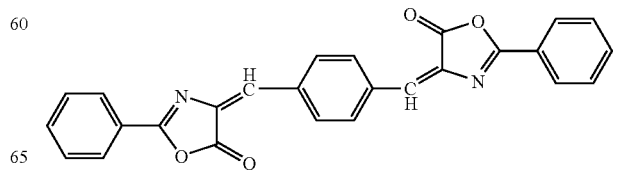

Methine derivatives, such as:

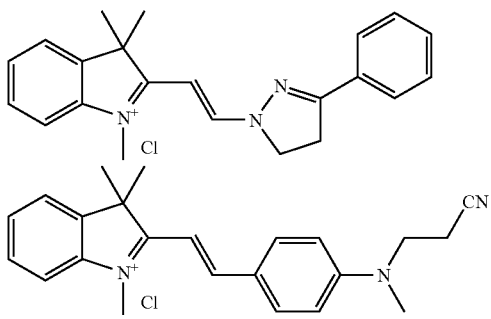

Oxazine and thiazine derivatives, such as:

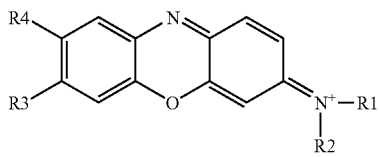

wherein R1, R2, R3, and R4 are defined above. A non-limiting example of such derivatives is:

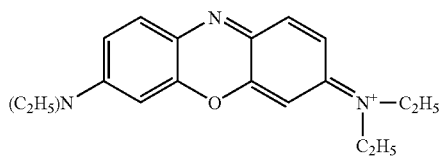

Basic Blue 3, C.I. 51004

1,4-Distyrylbenzene derivatives of formula:

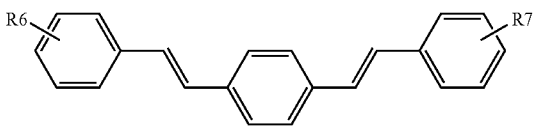

wherein R6 and R7, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$)alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched, and cyclic $C_1$-$C_6$ alkoxy, optionally substituted aryl, carboxyl, and sulpho groups, and halogen atoms, it being possible for these alkyl radicals to be interrupted by at least one heteroatom, such as N, S, and O.

4,4'-Distyrylbiphenyl derivatives of formula:

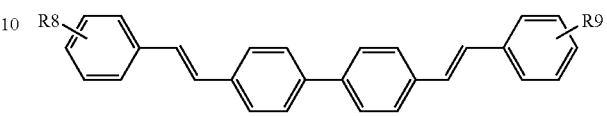

wherein R8 and R9, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$)alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen.

Triazinylaminostilbene derivatives of formula:

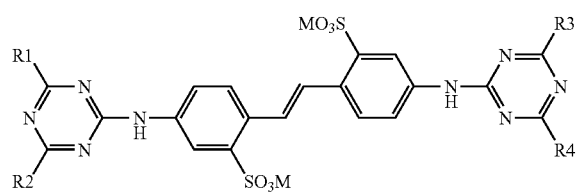

wherein R1, R2, R3, and R4, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$)alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen; and M is chosen from monovalent and divalent cations resulting from the family of alkali metals and alkaline earth metals, for example, sodium, potassium, and calcium ions.

Stilbazolium derivatives of formula:

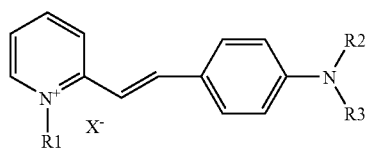

wherein R1, R2, and R3, which may be identical or different, are chosen from hydrogen; a halogen atoma; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$) alkylamino groups; ($C_1$-$C_6$)alkoxy groups; ($C_1$-$C_6$) alkoxycarbonyl groups; carboxy($C_1$-$C_6$)alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen;

or alternatively, two of the R2 and R3 substituents can form, together with the carbon atoms to which they are attached, a ring chosen from $C_6$-$C_{30}$ aromatic rings and heterocyclic rings comprising, in total, from 5 to 30 ring members and from 1 to 5 heteroatoms; this ring being fused or nonfused, these rings and possible fused rings being optionally substituted by at least one group chosen from $C_1$-$C_4$ alkyl, ($C_1$-$C_4$) alkoxy($C_1$-$C_4$)alkyl, amino, di($C_1$-$C_4$)alkylamino, halogen, phenyl, carboxyl, and tri($C_1$-$C_4$)alkylammonio($C_1$-$C_4$)alkyl groups, and X$^-$ is chosen from organic and inorganic anions, such as chloride, bromide, iodide, methosulphate, ethosulphate, mesylate, tosylate, and acetate ions and simple organic acid salts, such as lactates, oleates, benzoates, perchlorates, and triflates.

Stilbazolium dimers, such as compounds of formulas:

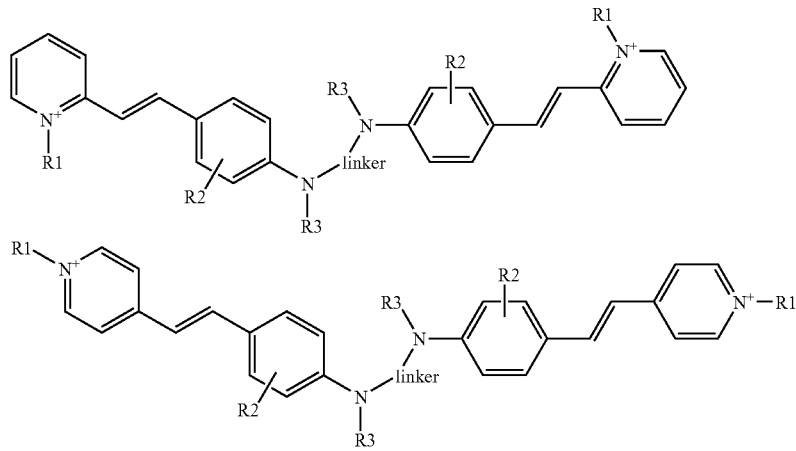

wherein R1, R2, and R3, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$) alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl group comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen.

Stilbazolium trimers and tetramers, such as the following compounds:

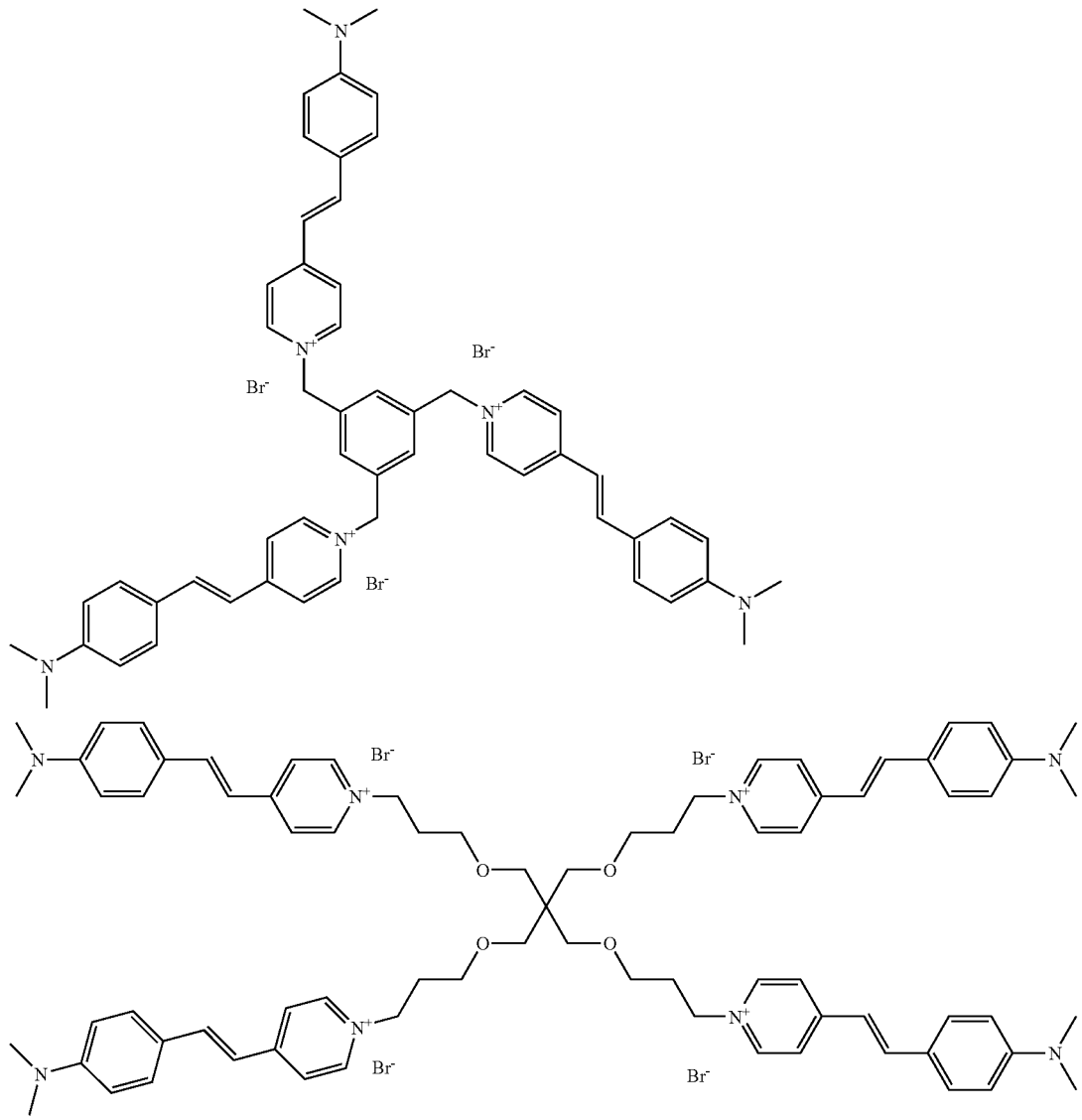

Bis(benzoxazole) derivatives of formula:

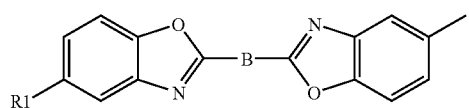

wherein R1 and R2, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$)alkoxy groups; piperidinosulphonyl groups; pyrrolidino groups; ($C_1$-$C_6$)alkylhalo ($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched, and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen; and B is chosen from:

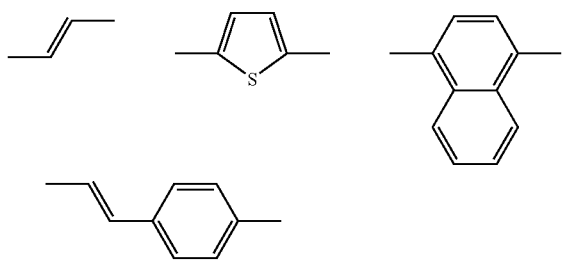

Cationic or noncationic bis(benzimidazoles);
Anionic and nonanionic 1,3-diphenyl-2-pyrazolines, for example:

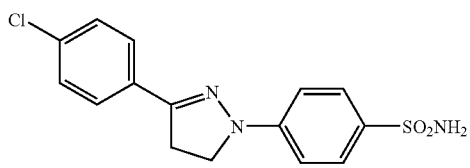

Diketopyrrolopyrroles of formula:

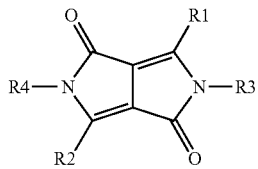

wherein R1, R2, R3, and R4, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$) alkylamino groups; ($C_1$-$C_6$)alkoxy groups; ($C_1$-$C_6$) alkoxycarbonyl groups; carboxy($C_1$-$C_6$)alkoxy groups; piperidinosulphonyl groups; pyrrolidino groups; ($C_1$-$C_6$)alkylhalo($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched, and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen.

A non-limiting example of such compounds is:

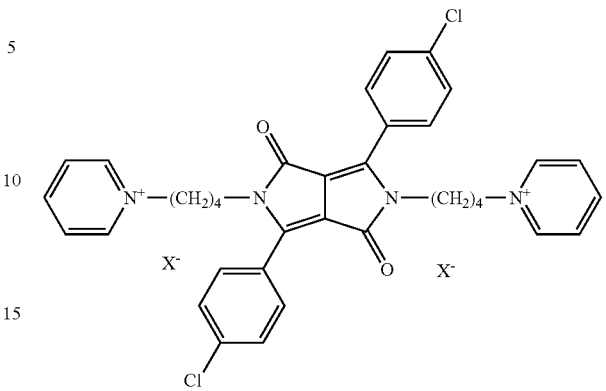

wherein $X^-$ is an anion as defined above.

Dicyanopyrazine derivatives, such as compounds of formulas:

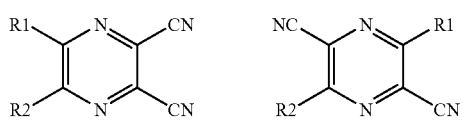

wherein R1 and R2, which may be identical or different, are chosen from hydrogen; halogen atoms; $C_6$-$C_{30}$ aryl groups; hydroxyl groups; cyano groups; nitro groups; sulpho groups; amino groups; acylamino groups; di($C_1$-$C_6$)alkylamino groups; dihydroxy($C_1$-$C_6$)alkylamino groups; ($C_1$-$C_6$)alkylhydroxy($C_1$-$C_6$)alkylamino groups; ($C_1$-$C_6$)alkoxy groups; ($C_1$-$C_6$)alkoxycarbonyl groups; carboxy($C_1$-$C_6$)alkoxy groups; piperidinosulphonyl groups; pyrrolidino groups; ($C_1$-$C_6$)alkylhalo ($C_1$-$C_6$)alkylamino groups; benzoyl($C_1$-$C_6$)alkyl groups; vinyl groups; formyl groups; $C_6$-$C_{30}$ aryl radicals optionally substituted by at least one group chosen from hydroxyl groups, linear, branched, and cyclic $C_1$-$C_6$ alkoxy groups and linear, branched, and cyclic alkyl groups comprising from 1 to 22 carbon atoms, which may be optionally substituted by at least one group chosen from hydroxyl, amino, and $C_1$-$C_6$ alkoxy groups; linear, branched, and cyclic alkyl radicals comprising from 1 to 22 carbon atoms, for example, from 1 to 6 carbon atoms, optionally substituted by at least one group chosen from hydroxyl, amino, linear, branched, and cyclic $C_1$-$C_6$ alkoxy, optionally substituted aryl, carboxyl, and sulpho groups, and halogen atoms, it being possible for these alkyl radicals to be interrupted by at least one heteroatom, such as nitrogen, sulphur, and oxygen;

or alternatively, two of the R1 and R2 substituents can form, together with the carbon atoms to which they are attached, a ring chosen from $C_6$-$C_{30}$ aromatic and nonaromatic rings and heterocyclic ring comprising, in total, from 5 to 30 ring members and from 1 to 5 heteroatoms; these rings being fused or nonfused, optionally comprising a carbonyl group, and being optionally substituted by at least one group chosen from $C_1$-$C_4$ alkyl, ($C_1$-$C_4$)alkoxy($C_1$-$C_4$)alkyl, amino, di($C_1$-$C_4$) alkylamino, halogen, phenyl, carboxyl, and tri($C_1$-$C_4$)alkylammonio($C_1$-$C_4$)alkyl groups;

wherein two of the R2 and R3 substituents can form, together with the carbon atoms to which they are attached, a ring chosen from $C_6$-$C_{30}$ aromatic rings and heterocyclic rings comprising, in total, from 5 to 30 ring members and from 1 to 5 heteroatoms; this ring being fused or nonfused, this ring and the possible fused ring being optionally substituted by at least one group chosen from $C_1$-$C_4$ alkyl, ($C_1$-$C_4$)alkoxy($C_1$-$C_4$) alkyl, amino, di($C_1$-$C_4$)alkyl-amino, halogen, phenyl, carboxyl, and tri($C_1$-$C_4$)alkylammonio($C_1$-$C_4$)alkyl groups.

Mention may be made, for example, of the compounds described in the publication "Selective topochemical photoreaction of crystallized 2,3-(phenylethenyl)-4,5-dicyanopyrazine" by Kim, Jae Hong; Matsuoka Masaru, Chem. Lett. (1999), (2), 143-144.

Further non-limiting examples include:

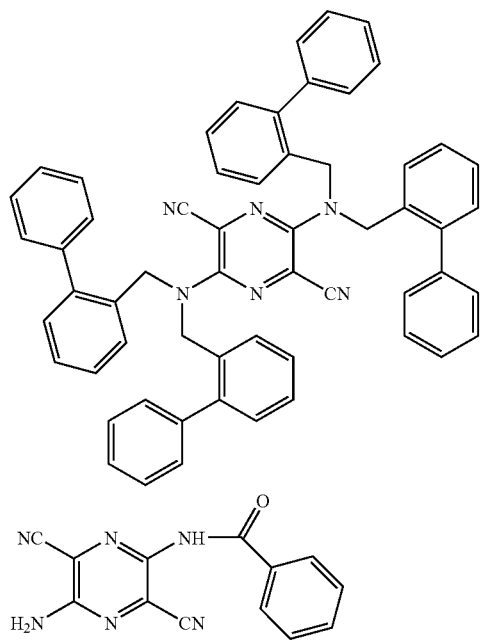

The colored entity present in the composition of the present disclosure may also be chosen from pigments.

As used herein, the term "pigment" is understood to mean any organic and/or inorganic entity having a solubility in water of less than 0.01% at 20° C., for example, less than 0.0001%, and exhibiting an absorption at wavelengths ranging from 350 to 700 nm, and in at least one embodiment, an absorption with a maximum.

The pigments may be chosen from organic and/or inorganic pigments known the art, by way of non-limiting example, from those which are described in Kirk-Othmer's Encyclopedia of Chemical Technology and in Ullmann's Encyclopedia of Industrial Chemistry.

These pigments can be provided in the form of powders and pigment pastes. They can be coated or uncoated.

The pigments may, for example, be chosen from inorganic pigments, organic pigments, lakes, special effect pigments, such as pearlescent agents and glitter, and mixtures thereof.

According to one embodiment, the at least one pigment may be chosen from inorganic pigments. As used herein, the term "inorganic pigment" is understood to mean any pigment which corresponds to the definition of the Ullmann's Encyclopaedia in the "Inorganic Pigment" chapter. Non-limiting examples of such inorganic pigments include optionally surface treated titanium dioxide, zirconium and cerium oxides, iron and chromium oxides, manganese violet, ultramarine blue, chromium hydrate, and ferric blue. Further examples of suitable inorganic pigments include, but are not limited to: $Ta_2O_5$, $Ti_3O_5$, $Ti_2O_3$, TiO, mixtures of $ZrO_2$ and $TiO_2$, $ZrO_2$, $Nb_2O_5$, $CeO_2$, and ZnS.

Pigments which are not surface treated, subsequently referred to herein as "pigments", may be chosen from organic pigments. As used herein, the term "organic pigment" is understood to mean any pigment which corresponds to the definition of Ullmann's Encyclopaedia in the "Organic Pigment" chapter. The organic pigment may be chosen, for example, from nitroso, nitro, azo, xanthene, quinoline, anthraquinone, and phthalocyanine compounds, compounds of metal complex type, isoindolinone compounds, isoindoline compounds, quinacridone compounds, perinone compounds, perylene compounds, diketopyrrolopyrrole compounds, thioindigo compounds, dioxazine compounds, triphenylmethane compounds, and quinophthalone compounds.

In at least one embodiment, white and colored organic pigments can be chosen from carmine; carbon black; aniline black; azo yellow; quinacridone; phthalocyanine blue; sorghum red; the blue pigments codified in the Color Index under the references CI 42090, 69800, 69825, 73000, 74100, and 74160; the yellow pigments codified in the Color Index under the references CI 11680, 11710, 15985, 19140, 20040, 21100, 21108, 47000, and 47005; the green pigments codified in the Color Index under the references CI 61565, 61570, and 74260; the orange pigments codified in the Color Index under the references CI 11725, 15510, 45370, and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915, and 75470; and the pigments obtained by oxidative polymerization of indole or phenol derivatives, such as those described in French Patent No. 2 679 771.

Non-limiting examples of commercially available pigment pastes formed of organic pigment, include the products sold by Hoechst under the names:
Cosmenyl Yellow 1OG: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Cosmenyl Carmine FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260); and
Cosmenyl Black R: Pigment Black 7 (CI 77266).

The pigments in accordance with the present disclosure may also be in the form of composite pigments, such as those described in European Patent No. 1 184 426. These composite pigments may comprise, for example, particles comprising an inorganic core, at least one binder, which provides for the attachment of the organic pigments to the core, and at least one organic pigment which at least partially covers the core.

The organic pigments may also be chosen from lakes. As used herein, the term "lake" is understood to mean dyes adsorbed onto insoluble particles, the combination thus obtained remaining insoluble during use.

The inorganic substrates onto which the dyes are adsorbed include, for example, alumina, calcium sodium borosilicate, calcium aluminium borosilicate, and aluminium.

Examples of suitable dyes include, but are not limited to, cochineal carmine and the dyes known under the following names: D & C Red 21 (CI 45 380), D & C Orange 5 (CI 45

370), D & C Red 27 (CI 45 410), D & C Orange 10 (CI 45 425), D & C Red 3 (CI 45 430), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 0 (CI 77 002), D & C Green 3 (CI 42 053), and D & C Blue 1 (CI 42 090).

A further non-limiting example of a suitable lake is the product known under the name D & C Red 7 (CI 15 850:1).

The at least one pigment may also be chosen from special effect pigments. As used herein, the term "special effect pigments" is understood to mean pigments which generally create a colored appearance (characterized by a certain hue, a certain vividness, and a certain lightness) which is not uniform and which changes as a function of the conditions of observation (e.g., light, temperature, angles of observation, and the like). They thereby contrast with white or colored pigments, which provide a conventional opaque, semitransparent or transparent uniform color.

Several types of special effect pigments are suitable for use in accordance with the present disclosure, for instance, those with a low refractive index, such as fluorescent, photochromic, and thermochromic pigments, and those with a greater refractive index, such as pearlescent agents and glitter.

Non-limiting examples of special effect pigments include white pearlescent pigments, such as mica covered with titanium dioxide and mica covered with bismuth oxychloride, colored pearlescent pigments, such as mica covered with titanium dioxide and with iron oxides, mica covered with titanium dioxide and with ferric blue, mica covered with titanium dioxide and with chromium oxide, and mica covered with titanium dioxide and with an organic pigment as defined above, and pearlescent pigments based on bismuth oxychloride. Examples of suitable pearlescent pigments include, but are not limited to, Cellini sold by Engelhard (mica-$TiO_2$-lake), Prestige sold by Eckart (mica-$TiO_2$), Prestige Bronze sold by Eckart (mica-$Fe_2O_3$), and Colorona sold by Merck (mica-$TiO_2$—$Fe_2O_3$).

In addition to pearlescent agents on a mica support, use may also be made of multilayer pigments based on synthetic substrates, such as alumina, silica, calcium sodium borosilicate, calcium aluminum borosilicate, and aluminum.

The special effect pigments may also be chosen from those with an interference effect which are not attached to a substrate, such as liquid crystals (e.g., Helicones HC from Wacker), interference holographic glitter (e.g., Geometric Pigment or Spectra f/x from Spectratek). Special effect pigments also include fluorescent pigments, whether substances which are fluorescent in daylight or which produce ultraviolet fluorescence, phosphorescent pigments, photochromic pigments, thermochromic pigments, and quantum dots, for example, those sold by Quantum Dots Corporation.

Quantum dots are luminescent semiconductor nanoparticles capable of emitting, under light excitation, radiation exhibiting a wavelength ranging 400 nm to 700 nm. These nanoparticles are known in the art, for example, they can be synthesized according to the processes described, for example, in U.S. Pat. Nos. 6,225,198 and 5,990,479, in the publications which are cited therein, and in the following publications: Dabboussi B. O. et al., "(CdSe)ZnS core-shell quantum dots: synthesis and characterisation of a size series of highly luminescent nanocristallites", Journal of Physical Chemistry B, vol. 101, 1997, pp. 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pp. 7019-7029.

The variety of the pigments which can be used in the present disclosure makes it possible to obtain a rich palette of colors as well as specific optical effects, such as interference, metallic effects.

According to one embodiment, the pigments are colored pigments. As used herein, the term "colored pigment" is understood to mean pigments other than white pigments.

The size of the pigment used in the cosmetic composition according to the present disclosure may range from 10 nm to 200 µm, for example, from 20 nm to 80 µm, or from 30 nm to 50 µm.

In another embodiment, the pigments can be dispersed in the product by virtue of at least one dispersing agent.

The dispersing agent serves to protect the dispersed particles from the agglomeration or flocculation thereof. The at least one dispersing agent may be chosen, for example, from surfactants, oligomers, polymers, and mixtures thereof, carrying at least one functionality having a strong affinity for the surface of the particles to be dispersed. In one embodiment, the at least one dispersing agent can become attached physically or chemically to the surface of the pigments. The at least one dispersant additionally exhibits at least one functional group compatible with or soluble in the continuous medium. Non-limiting examples of suitable dispersing agents include esters of 12-hydroxystearic acid, esters of $C_8$ to $C_{20}$ fatty acid, and esters of polyol, such as glycerol and diglycerol, such as the stearate of poly(12-hydroxy-stearic acid) with a molecular weight of approximately 750 g/mol, for instance, the product sold under the name of Solsperse 21 000 by Avecia, polyglyceryl-2 dipolyhydroxystearate (CTFA name), sold under the reference Dehymyls PGPH by Henkel, and polyhydroxystearic acid, such as the product sold under the reference Arlacel P100 by Uniqema, and mixtures thereof.

Other dispersants which can be used in the compositions of the present disclosure include, but are not limited to, quaternary ammonium derivatives of polycondensed fatty acids, such as Solsperse 17 000, sold by Avecia, and polydimethylsiloxane/oxypropylene mixtures, such as those sold by Dow Corning under the references DC2-5185 and DC2-5255 C.

The polydihydroxystearic acid and the esters of 12-hydroxystearic acid may be used, for example, with a medium chosen from hydrocarbon mediums and fluorinated mediums, while the oxyethylene/oxypropylene polydimethylsiloxane mixtures may be used with a silicone medium.

The pigments used in the cosmetic composition according to the present disclosure may be chosen from those surface-treated with at least one organic agent.

Thus, the pigments surface-treated before use in the context of the present disclosure are pigments or fillers which have been completely or partially subjected to a surface treatment chosen from chemical, electronic, electrochemical, mechanochemical, and mechanical surface treatments with at least one organic agent, such as those which are described in Cosmetics and Toiletries, February 1990, Vol. 105, pp. 53-64, before being dispersed in the composition of the present disclosure. The at least one organic agent may, for example, be chosen from amino acids; waxes, for example, carnauba wax and beeswax; fatty acids, fatty alcohols and their derivatives, such as stearic acid, hydroxystearic acid, stearyl alcohol, hydroxystearyl alcohol, lauric acid and their derivatives; anionic surfactants; lecithins; sodium, potassium, magnesium, iron, titanium, zinc, and aluminum salts of fatty acids, for example, aluminum stearate and aluminum laurate; metal alkoxides; polysaccharides, for example chitosan, cellulose and its derivatives; polyethylene; (meth)acrylic polymers, for example polymethyl methacrylates; polymers and copolymers comprising acrylate units; proteins; alkanolamines; silicone compounds, for example, silicones, polydimethylsiloxanes, alkoxysilanes, alkylsilanes, and siloxysilicates; fluorinated organic compounds, for example, perfluoroalkyl ethers; and fluorosilicone compounds.

The surface-treated pigments used in the cosmetic composition according to the present disclosure may also be treated with a mixture of these compounds and/or undergo several surface treatments.

The surface-treated pigments useful in accordance with the present disclosure may be prepared according to surface treatment techniques known to a person skilled in the art or may be chosen from those available commercially.

According to one embodiment, the surface-treated pigments are covered with an organic layer.

The organic agent with which the pigments are treated can be deposited on the pigments by a method chosen from evaporation of solvent, chemical reaction between the molecules of the surface agent, and creation of a covalent bond between the surface agent and the pigments.

The surface treatment can thus be carried out, for example, by chemical reaction of a surface agent with the surface of the pigments and creation of a covalent bond between the surface agent and the pigments or fillers. This method is described, for example, in U.S. Pat. No. 4,578,266.

In at least one embodiment, the surface-treated pigments are chosen from pigments to which an organic agent is covalently bonded.

The at least one agent for the surface treatment may be present in an amount ranging from 0.1 to 50% by weight, for example, from 0.5 to 30% by weight, or from 1 to 10% by weight, relative to the total weight of the surface-treated pigments.

According to at least one embodiment, the surface treatments of the pigments are chosen from the following treatments:

PEG-silicone treatments, such as the AQ surface treatment marketed by LCW;
chitosan treatments, such as the CTS surface treatment marketed by LCW;
triethoxycaprylylsilane treatments, such as the AS surface treatment sold by LCW;
methicone treatments, such as the Si surface treatment marketed by LCW;
dimethicone treatments, such as the Covasil 3.05 surface treatment marketed by LCW;
dimethicone/trimethylsiloxysilicate treatments, such as the Covasil 4.05 surface treatment marketed by LCW;
lauroyl lysine treatments, such as the LL surface treatment marketed by LCW;
lauroyl lysine dimethicone treatments, such as LL/SI surface treatment marketed by LCW;
magnesium myristate treatments, such as the MM surface treatment marketed by LCW;
aluminium dimyristate treatments, such as the Ml surface treatment marketed by Miyoshi;
perfluoropolymethylisopropyl ether treatments, such as the FHC surface treatment marketed by LCW;
isostearyl sebacate treatments, such as the HS surface treatment marketed by Miyoshi;
disodium stearoyl glutamate treatments, such as the NAI surface treatment marketed by Miyoshi;
dimethicone/disodium stearoyl glutamate treatments, such as the SA/NAI surface treatment marketed by Miyoshi;
perfluoroalkyl phosphate treatments, such as the PF surface treatment marketed by Daito;
acrylate/dimethicone copolymer and perfluoroalkyl phosphate treatments, such as the FSA surface treatment marketed by Daito;
polymethylhydrosiloxane/perfluoroalkyl phosphate treatments, such as the FS01 surface treatment marketed by Daito;
lauroyl lysine/aluminium tristearate treatments, such as the LL-StAl surface treatment marketed by Daito;
octyltriethylsilane treatments, such as the OTS surface treatment marketed by Daito;
octyltriethylsilane/perfluoroalkyl phosphate treatments, such as the FOTS surface treatment marketed by Daito;
acrylate/dimethicone copolymer treatments, such as the ASC surface treatment marketed by Daito;
isopropyl titanium triisostearate treatments, such as the ITT surface treatment marketed by Daito;
microcrystalline cellulose and carboxymethyl cellulose treatments, such as the AC treatment marketed by Daito;
cellulose treatments, such as the C2 surface treatment marketed by Daito;
acrylate copolymer treatments, such as the APD surface treatment marketed by Daito; and
perfluoroalkyl phosphate/isopropyl titanium triisostearate treatments, such as the PF+ITT surface treatment marketed by Daito.

The composition in accordance with the present disclosure may further comprise at least one pigment which are not surface treated.

Coloring Entities

Non-limiting examples of suitable coloring entities include dye precursors, such as oxidation bases and couplers. The oxidations bases may be chosen from those conventionally used in oxidation dyeing, for example, paraphenylenediamines, bisphenylalkylenediamines, para-aminophenols, ortho-aminophenols, and heterocyclic bases. Non-limiting examples of suitable couplers include meta-phenylenediamines, meta-aminophenols, meta-diphenols, naphthols, and heterocyclic couplers, for example, indole derivatives, indoline derivatives, pyridine derivatives, indazole derivatives, pyrazolo[1,5-b]-1,2,4-triazole derivatives, pyrazolo[3,2-c]-1,2,4-triazole derivatives, benzimidazole derivatives, benzothiazole derivatives, benzoxazole derivatives, 1,3-benzodioxole derivatives, and pyrazolones, and their acid addition salts.

The at least one colored or coloring entity may be present in the composition in an amount ranging from 0.01 to 50%, for example, from 0.5 to 20%.

According to one embodiment, the colored entity is a pigment.

Silicone Compounds

The composition of the present disclosure comprises at least one silicone compound exhibiting a viscosity of less than or equal to 100 centistokes (cSt), measured at 25° C. Such a silicone compound of low viscosity may be chosen, for example, from linear and cyclic silicones comprising from 2 to 7 silicon atoms, these silicones optionally comprising at least one group chosen from alkyl and alkoxy groups comprising from 1 to 10 carbon atoms, for example octamethylcyclotetrasiloxane, decamethylcyclopentasiloxane, dodecamethylcyclohexasiloxane, heptamethylhexyltrisiloxane, heptamethylethyltrisiloxane, heptamethyloctyltrisiloxane, octamethyltrisiloxane, decamethyltetrasiloxane, and mixtures thereof. According to one embodiment, the at least one silicone compound is chosen from cyclopentadimethylsiloxane and dodecamethylcyclohexasiloxane.

According to another embodiment, the at least one silicone compound has a viscosity of less than 50 centistokes.

The at least one silicone compound with a viscosity of less than 100 cSt may be present in the composition according to the present disclosure in an amount ranging from 0.1% to 90% by weight, relative to the total weight of the composition, for example, from 1% to 80% by weight, or from 5% to 70% by weight.

The composition of the present disclosure may further comprise other nonvolatile organic solvents, such as:
- nonvolatile aromatic alcohols, such as benzyl alcohol and phenoxyethanol;
- esters of liquid $C_1$-$C_{20}$ acids and of nonvolatile $C_1$-$C_8$ alcohols, such as isopropyl myristate;
- ethylene carbonate, propylene carbonate, and butylene carbonate;
- nonvolatile polyols, such as glycerol, ethylene glycol, dipropylene glycol, and butylene glycol;
- nonvolatile glycol ethers, such as diethylene glycol monoethyl ether and dipropylene glycol mono(n-butyl)ether;
- nonvolatile hydrocarbon oils, such as isohexadecane;
- nonvolatile liquid $C_{10}$-$C_{30}$ fatty alcohols, such as oleyl alcohol, liquid $C_{10}$-$C_{30}$ fatty alcohol esters, such as $C_{10}$-$C_{30}$ fatty alcohol benzoates, and mixtures thereof; polybutene oil, isononyl isononanoate, isostearyl malate, pentaerythrityl tetra-isostearate, and tridecyl trimelate; and
- nonvolatile perfluorinated solvents, such as perfluoroperhydrophenanthrene, sold under the name of "Flutec PC11®" by F2 Chemicals.

The composition may further comprise fillers which are generally compounds which are substantially colorless, which are solid at ambient temperature and atmospheric pressure, and which are insoluble in the various ingredients of the composition, even when these ingredients are brought to a temperature greater than ambient temperature.

The fillers may be chosen from inorganic and organic fillers. The fillers may be particles of any shape, for example, platelet, spherical, and oblong particles, whatever their crystallographic form (for example, sheet, cubic, hexagonal, and orthorhombic). Moreover, these particles may be chosen from solid, hollow, and porous and coated and uncoated particles.

Examples of fillers which can be used in the compositions according to the present disclosure include, but are not limited to, inorganic fillers, such as talc; natural and synthetic mica; silica; kaolin; boron nitride; precipitated calcium carbonate; magnesium carbonate; basic magnesium carbonate; and hydroxyapatite.

These inorganic fillers may be provided in the form of spherical particles with, for example, hollow silica microspheres, such as the "Silica Beads SB 700/HA®" and "Silica Beads SB 700®" from Maprecos and the "Sunspheres H-33®" and "Sunspheres H-51®" from Asahi Glass.

According to at least one embodiment, the at least one inorganic particle exhibits a number-average primary size ranging from 0.1 to 30 μm, for example, from 0.2 to 20 μm, or from 0.5 to 15 μm. As used herein, the term "primary particle size" is understood to mean the maximum dimension which it is possible to measure between two diametrically opposite points of an individual particle. The size of the organic particles can be determined, for example, by a method chosen from transmission electron microscopy, measurement of the specific surface by the BET method, and laser particle size determination.

According to one embodiment, the inorganic fillers used according to the present disclosure are chosen from silica, talc, and boron nitride.

The fillers which can be used in the compositions according to the present disclosure may also be chosen from organic fillers. As used herein, the term "organic filler" is understood to mean a polymeric particle which can result from the polymerization of at least one monomer. The polymers constituting these organic particles may or may not be crosslinked. The monomers may be chosen, by way of non-limiting example, from methacrylic and acrylic acid esters, such as methyl acrylates and methyl methacrylate, vinylidene chloride, acrylonitrile, and styrene and its derivatives.

According to one embodiment, the at least one organic particle may have a number-average primary size ranging from 1 to 30 μm, for example, from 1 to 20 μm, or from 1 to 15 μm.

The at least one organic particle used in the cosmetic composition according to the present disclosure may, for example, be chosen from polyamide powders, acrylic polymer powders, such as polymethyl methacrylate powders, acrylic copolymer powders, such as polymethyl methacrylate/ethylene glycol dimethylacrylate powders, polyallyl methacrylate/ethylene glycol dimethacrylate powders, ethylene glycol dimethacrylate/lauryl methacrylate copolymer powders, and polyacrylate/alkyl acrylate powders, polystyrene powders, polyethylene powders, such as polyethylene/acrylic acid powders, and silicone resin microbeads.

Non-limiting examples of suitable organic particles include:
- polyamide (Nylon®) powders, for example, those sold under the names "Orgasol® 4000" and "Orgasol® 2002 UD NAT COS 24" by Atochem,
- acrylic polymer powders, for example, polymethyl methacrylate powders, such as those sold under the name "Covabead® LH85" and "Covabead® PMMA" by Wacker and those sold under the name "Micropearl® MHB" by Matsumoto,
- acrylic copolymer powders, for example, polymethyl methacrylate/ethylene glycol dimethacrylate powders, such as those sold under the name of "Dow Corning 5640 Microsponge® Skin Oil Adsorber" by Dow Corning and those sold under the name "Ganzpearl® GMP-0820" by Ganz Chemical, polyallyl methacrylate/ethylene glycol dimethacrylate powders, such as those sold under the names "Polypore® L200" and "Polypore® E200" by Amcol, ethylene glycol dimethacrylate/lauryl methacrylate copolymer powders, such as those sold under the name "Polytrap® 6603" by Dow Corning, and polyacrylate/ethylhexyl acrylate powders, such as those sold under the name "Techpolymer® ACX 806C" by Sekisui,
- polystyrene/divinylbenzene powders, such as those sold under the name "Techpolymer® SBX8" by Sekisui,
- polyethylene powders, for example, polyethylene/acrylic acid powders, sold under the name "Flobeads®" by Sumitomo,
- silicone resin microbeads, such as those sold under the names "Tospearl®" by Toshiba Silicone, such as "Tospearl® 240A" and "Tospearl® 120A",
- acrylic polymer microspheres, such as those made of crosslinked acrylate copolymer, for example, "Polytrap 6603 Adsorber®" from RP Scherrer,
- polyurethane powders, such as the hexamethylene diisocyanate and trimethylol hexyllactone copolymer powder sold under the name "Plastic Powder D-400®" by Toshiki, methyl acrylate and methacrylate polymer and copolymer microcapsules and vinylidene chloride and acrylonitrile copolymer microcapsules, such as "Expancel®" from Expancel, crosslinked organopolysiloxane elastomer powders, such as those sold under the name "Trefil Powder E-506C" by Dow Corning, and polyfluorinated powders, such as polytetrafluoroethylene powders, for example that sold under the name "MP 1400" by DuPont de Nemours.

According to one embodiment, the organic particles used in the composition in accordance with the present disclosure are chosen from polyamide powders and polymethyl methacrylate powders.

The colored or coloring entities and fillers may be present in the composition in an amount ranging from 0.001 to 20% by weight, relative to the total weight of the composition, for example, from 0.1 to 10%.

In order to obtain better spreading of the composition of the present disclosure and improved sheathing, the composition may further comprise at least one polysiloxane exhibiting a viscosity of greater than 100 cSt, for example, greater than 300 cSt. The viscosity of these polysiloxanes can be measured according to Standard ASTM D-445. Such polysiloxanes may be chosen, for example, from silicone oils, gums, and resins, grafted silicones, and crosslinked silicones.

Examples of polysiloxanes with a viscosity of greater than 100 cSt include, but are not limited to, polydimethylsiloxanes; alkyl dimethicones; polyphenylmethylsiloxanes, such as phenyl dimethicones, phenyl trimethicones, and vinyl methyl methicones; silicones modified by aliphatic and/or aromatic groups which are optionally fluorinated; and silicones modified by functional groups, such as hydroxyl, thiol, and/or amine groups.

Such polysiloxanes may be chosen, by way of non-limiting example, from the silicones of formula (I):

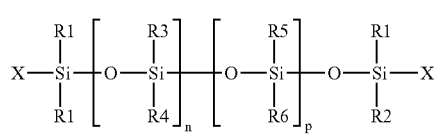

(I)

wherein R1, R2, R5, and R6, which may be identical or different, are chosen from alkyl radicals comprising from 1 to 6 carbon atoms; R3 and R4, which may be identical or different, are chosen from alkyl radicals comprising from 1 to 6 carbon atoms, vinyl radicals, aryl radicals, amine radicals, and hydroxyl radicals; X is chosen from alkyl radicals comprising from 1 to 6 carbon atoms, hydroxyl radicals, vinyl radicals, and amine radicals; and n and p are integers chosen so as to obtain a viscosity of greater than 300 cSt.

Non-limiting examples of such compounds include the following polydimethylsiloxanes in which:

the substituents R1 to R6 and X are methyl groups, such as the product sold under the name Baysilicone TP 3898 by General Electric and the product sold under the name AK 500000 by Wacker, the substituents R1 to R6 and X are methyl groups and p and n are such that the molecular weight is 120 000 g/mol, such as the product sold under the name Dow Corning 200 Fluid 60000 CS by Dow Corning, the substituents R1 to R6 and X are methyl groups and p and n are such that the molecular weight is 250 000 g/mol, such as the product sold under the name Mirasil DM 500,000 by the company Rhodia and the product sold under the name Dow Corning 200 Fluid 500,000 cSt by Down Corning, the substituents R1 to R6 are methyl groups, the X group is a hydroxyl group and n and p are such that the molecular weight of the polymer is 600 000 g/mol, such as the product sold under the name SGM 36 by Dow Corning, and dimethicones of the (polydimethylsiloxane)(methylvinylsiloxane) type, such as SE63, sold by GE Bayer Silicones, poly(dimethylsiloxane)(diphenyl)(methylvinylsiloxane) copolymers, and mixtures thereof.

When the polysiloxane comprises a fluorinated group, the polysiloxane may be chosen, for example, from copolymers of the following formula:

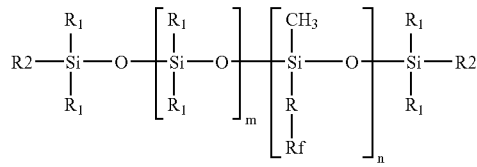

wherein R is chosen from linear and branched divalent alkyl groups comprising from 1 to 6 carbon atoms, for example, divalent methyl, ethyl, propyl, and butyl groups; Rf is chosen from fluoroalkyl radicals, such as perfluoroalkyl radicals, comprising from 1 to 12 carbon atoms, for example, from 1 to 9 carbon atoms; $R_1$, which may be identical or different, is chosen from $C_1$-$C_{20}$ alkyl radicals, hydroxyl radicals, and phenyl radicals, R2 is chosen from $R_1$ or Rf; m is a number ranging from 0 to 500, for instance, from 0 to 200; and n is chosen from 1 to 1000, for instance, from 1 to 500.

According to one embodiment, the $R_1$ groups are identical and are methyl radicals.

Such polysiloxanes are sold, by way of non-limiting example, by Shin-Etsu under the names 'FL-5', 'FL-10', 'X22-821', 'X22-822', and 'FL-100', by Dow Corning under the name FS-1265 Fluid, and by Phoenix Chemical under the Pecosil FS range under the names Pecosil FSL-150, Pecosil FSL-300, Pecosil FSH-150, Pecosil FSH-300, Pecosil FSU-150, and Pecosil FSU-300.

The weight-average molecular weight of the at least one polysiloxane may range, for example, from 1000 to 1 500 000 g/mol, such as from 20 000 to 1 000 000 g/mol.

According to one embodiment, the at least one polysiloxane can be in the resin form. As used herein, the term "resin" is understood to mean a crosslinked or non-crosslinked three-dimensional structure. Examples of polysiloxane resins include, but are not limited to, silsesquioxanes and siloxysilicates.

The nomenclature of silicone resins is known under the name of "MDTQ", the resin being described as a function of the various monomeric siloxane units which it comprises, each of the letters "MDTQ" characterizing a type of unit.

The letter M represents the monofunctional unit of formula $(CH_3)_3SiO_{1/2}$, the silicon atom being connected to a single oxygen atom in the polymer comprising this unit.

The letter D signifies a difunctional unit $(CH_3)_2SiO_{2/2}$ in which the silicon atom is connected to two oxygen atoms.

The letter T represents a trifunctional unit of formula $(CH_3)SiO_{3/2}$.

In the M, D and T units defined above, at least one of the methyl groups can be substituted by an R group different from the methyl group, for example, a group chosen from hydrocarbon radicals (e.g., alkyl radicals) comprising from 2 to 10 carbon atoms, phenyl groups, and hydroxyl groups.

Finally, the letter Q means a tetrafunctional unit $SiO_{4/2}$ in which the silicon atom is bonded to four oxygen atoms themselves bonded to the remainder of the polymer.

Various resins with different properties can be obtained from these different units, the properties of these polymers varying according to the type of monomers (or units), the type and the number of substituted radicals, the length of the polymer chain, the degree of branching, and the size of the pendant chains.

Non-limiting example of such silicone resins include:
siloxysilicates, such as trimethylsiloxysilicates of formula (XXI):

$$[(CH_3)_3-Si-O]_x-(SiO_{4/2})_y \qquad (XXI)$$

which are (MQ units) in which x and y are integers ranging from 50 to 80, polysilsesquioxanes of formula $(CH_3SiO_{3/2})_x$ (T units) in which x is greater than 100 and at least one of the methyl radicals of which can be substituted by an R group as defined above, polymethylsilsesquioxanes, which are polysilsesquioxanes in which none of the methyl radicals is substituted by another group. Such polymethylsilsesquioxanes are described, for example, in U.S. Pat. No. 5,246,694, which is incorporated herein by reference.

Non-limiting examples of commercially available polymethylsilsesquioxane resins, include those which are sold:

by Wacker under the reference Resin MK, such as Belsil PMS MK: polymer comprising $CH_3SiO_{3/2}$ repeat units (T units) which can also comprise up to 1% by weight of $(CH_3)SiO_{2/2}$ units (D units) and which exhibits an average molecular weight of approximately 10 000, and by Shin-Etsu under the references KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups, and under the reference KR-251, which combines 88% of T units and 12% of dimethyl D units and have Si—OH end groups.

Examples of siloxysilicate resins include, but are not limited to, trimethylsiloxysilicate (TMS) resins, optionally in the form of powders. Such resins are sold, for instance, under the reference SR1000 by General Electric and under the reference TMS 803 by Wacker. Trimethylsiloxysilicate resins sold in a solvent include, for example, cyclomethicone, sold under the name "KR-7312J" by Shin-Etsu and "DC 749" and "DC 593" by Dow Corning.

In one embodiment of the present disclosure, the polysiloxanes used in the composition are soluble or dispersible in the composition of the present disclosure. In another embodiment, the silicone resin is solid at 25° C.

The composition of the present disclosure may further comprise at least one grafted silicone polymer. As used herein, the term "grafted silicone polymer" is understood to mean a polymer comprising a polysiloxane portion and a portion comprising a nonsilicone organic chain, one of the two portions constituting the main chain of the polymer and the other being grafted to the main chain.

The grafted silicone polymers used in the cosmetic composition according to the present disclosure may be chosen, for example, from polymers comprising a nonsilicone organic backbone grafted by monomers comprising a polysiloxane, polymers comprising a polysiloxane backbone grafted by nonsilicone organic monomers, and mixtures thereof.

The nonsilicone organic monomers constituting the main chain of the grafted silicone polymer may be chosen, by way of non-limiting example, from monomers comprising ethylenic unsaturation which can be polymerized by the radical route, monomers which can be polymerized by polycondensation, such as those forming polyamides, polyesters, and polyurethanes, and ring-opening monomers, such as those of the oxazoline and caprolactone type.

The polymers comprising a nonsilicone organic backbone grafted by monomers comprising a polysiloxane in accordance with the present disclosure may be chosen, for example, from those described in U.S. Pat. Nos. 4,693,935, 4,728,571, and 4,972,037, European Patent Application Nos. 0 412 704, 0 412 707, and 0 640 105, and International Patent Application Publication No. WO 95/00578. Such polymers may include, by way of non-limiting example, copolymers obtained by radical polymerization from monomers comprising ethylenic unsaturation and from silicone macromers having an end vinyl group and copolymers obtained by reaction of a polyolefin comprising functionalized groups and of a polysiloxane macromer having an end functional group which reacts with the said functionalized groups.

Further non-limiting examples of grafted silicone polymers suitable for use in accordance with the present disclosure include the grafted silicone copolymers comprising:

a) from 0.01 to 50% by weight of at least one polysiloxane macromer (C) of general formula:

$$X(Y)_nSi(R)_{3-m}Z_m \qquad (VI)$$

and b) from 0 to 98% by weight of at least one lipophilic monomer (A) of low lipophilic polarity comprising ethylenic unsaturation which can be polymerized by the radical route; and/or c) from 0 to 98% by weight of at least one polar hydrophilic monomer (B) comprising ethylenic unsaturation which can copolymerized with the monomer or monomers of the type (A);

wherein:

X is chosen from vinyl groups which can copolymerize with the monomers (A) and (B);

Y is chosen from divalent bonding groups;

R is chosen from hydrogen, $C_1$-$C_6$ alkyl radicals, $C_1$-$C_6$ alkoxy radicals, and $C_6$-$C_{12}$ aryl radicals;

Z is chosen from monovalent polysiloxane units having a number-average molecular weight of at least 500;

n is equal to 0 or 1; and m is an integer ranging from 1 to 3;

the percentages being calculated with respect to the total weight of the monomers (A), (B), and (C).

These polymers have a number-average molecular weight ranging, for example, from 10 000 to 2 000 000 and, in at least one embodiment, a glass transition temperature Tg or a crystalline melting point Am of at least −20° C.

Examples of lipophilic monomers (A) include, but are not limited to, acrylic and methacrylic acid esters of $C_1$-$C_{24}$ alcohols; styrene; polystyrene macromers; vinyl acetate; vinyl propionate; α-methylstyrene; tert-butylstyrene; butadiene; cyclohexadiene; ethylene; propylene; vinyltoluene; esters of acrylic and methacrylic acid and of 1,1-dihydroperfluoroalkanols and of their homologues; esters of acrylic and methacrylic acid and of ω-hydridofluoroalkanols; esters of acrylic and methacrylic acid and of fluoroalkylsulphonamido alcohols; esters of acrylic and methacrylic acid and of fluoroalkyl alcohols; esters of acrylic and methacrylic acid and of alcohol fluoroethers; and mixtures thereof. Further non-limiting examples of monomers (A) include n-butyl methacrylate, isobutyl methacrylate, stearyl methacrylate, tert-butyl acrylate, tert-butyl methacrylate, 2-ethylhexyl methacrylate, methyl methacrylate, 2-(N-methyl-perfluorooctanesulphonamido)ethyl acrylate; 2-(N-butylperfluorooctanesulfonamido)ethyl acrylate, heptadecafluorooctylmethylaminoethyl methacrylate, and mixtures thereof.

Examples of polar monomers (B) include, but are not limited to, acrylic acid, methacrylic acid, N,N-dimethylacrylamide, dimethylaminoethyl methacrylate, quaternized dimethylaminoethyl methacrylate, (meth)acrylamide, N-(t-butyl)acrylamide, maleic acid, maleic anhydride and their hemiesters, hydroxyalkyl (meth)acrylates, diallyldimethylammonium chloride, vinylpyrrolidone, vinyl ethers, maleimides, vinylpyridine, vinylimidazole, polar vinyl heterocyclic compounds, styrene sulphonate, allyl alcohol, vinyl alcohol, vinylcaprolactam, and mixtures thereof. Further non-limiting examples of monomers (B) include acrylic acid, N,N-dimethylacrylamide, dimethylaminoethyl methacrylate, quaternized dimethylaminoethyl methacrylate, vinylpyrrolidone, and mixtures thereof.

Examples of polysiloxane macromers (C) of formula (I) include, but are not limited to, those of formula (VII):

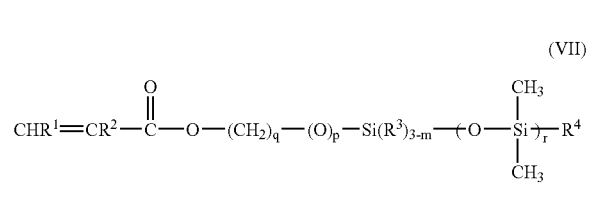

(VII)

wherein:
R$^1$ is chosen from hydrogen and —COOH, and, in at least one embodiment, hydrogen;
R$^2$ is chosen from hydrogen, methyl, and —CH$_2$COOH, and, in at least one embodiment, methyl;
R$^3$ is chosen from C$_1$-C$_6$ alkyl, alkoxy, and alkylamino radicals, C$_6$-C$_{12}$ aryl radicals, and hydroxyl radicals, and, in at least one embodiment, methyl;
R$^4$ is chosen from C$_1$-C$_6$ alkyl, alkoxy, and alkylamino radicals, C$_6$-C$_{12}$ aryl radicals, and hydroxyl radicals, and, in at least one embodiment, methyl;
q is an integer ranging from 2 to 6, and, in at least one embodiment, equal to 3;
p is equal to 0 or 1, and, in at least one embodiment, equal to 0;
r is an integer ranging from 5 to 700; and
m is an integer ranging from 1 to 3, and, in at least one embodiment, equal to 1;

Further non-limiting examples of polysiloxane macromers (C) include those of formula:

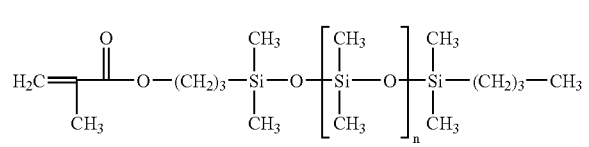

wherein n is a number ranging from 5 to 700.

The copolymer comprising a nonsilicone organic backbone grafted by monomers comprising a polysiloxane may, for example, have the following structure:

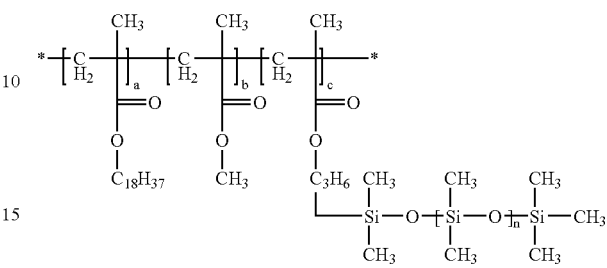

Such a polymer is sold under the name KP 561 by Shin-Etsu.

The copolymer comprising a nonsilicone organic backbone grafted by monomers comprising a polysiloxane may also have the following structure:

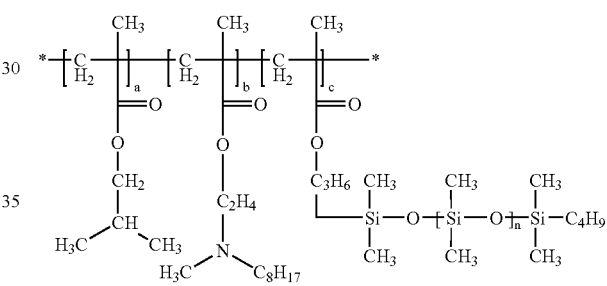

Such a polymer, Polysilicone 7, is sold under the name SA70 by 3M.

Other copolymers comprising a nonsilicone organic backbone grafted by monomers comprising a polysiloxane include, but are not limited to, KP545, KP574, and KP575, sold by Shin-Etsu.

In another embodiment of the present disclosure, the copolymer is capable of being obtained by radical polymerization from the following mixture of monomers:
a) 60% by weight of tert-butyl acrylate;
b) 20% by weight of acrylic acid; and
c) 20% by weight of silicone macromer of formula:

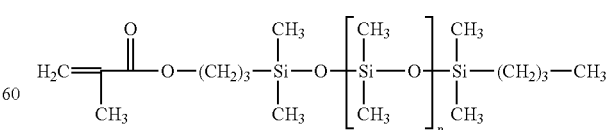

wherein n is a number ranging from 5 to 700; the percentages by weight being calculated with respect to the total weight of the monomers.

In yet another embodiment of the present disclosure, the copolymer is capable of being obtained by radical polymerization from the following mixture of monomers:

a) 80% by weight of tert-butyl acrylate;
b) 20% by weight of silicone macromer of formula:

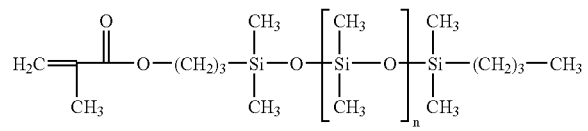

wherein n is a number ranging from 5 to 700; the percentages by weight being calculated with respect to the total weight of the monomers.

Further non-limiting examples of grafted silicone polymers comprising a nonsilicone organic backbone suitable for use in accordance with the present disclosure include grafted silicone copolymers capable of being obtained by reactive extrusion of a polysiloxane macromer having an end functional group which reacts with a polymer of the polyolefin type comprising reactive groups capable of reacting with the end functional group of the polysiloxane macromer in order to form a covalent bond which enables the silicone to be grafted to the main chain of the polyolefin. These polymers and the process for their preparation are described, for example, in International Patent Application Publication No. WO 95/00578.

The reactive polyolefins may be chosen, for example, from polyethylenes and polymers of monomers derived from ethylene, such as propylene, styrene, alkylstyrene, butylene, butadiene, (meth)acrylates, vinyl esters, and equivalents, comprising reactive functional groups capable of reacting with the end functional group of the polysiloxane macromer. In at least one embodiment, the reactive polyolefins are chosen from copolymers of ethylene and ethylene derivatives and of monomers chosen from those comprising a carboxyl functional group, such as (meth)acrylic acid; those comprising an acid anhydride functional group, such as maleic anhydride; those comprising an acid chloride functional group, such as (meth)acryloyl chloride; those comprising an ester functional group, such as (meth)acrylates; and those comprising an isocyanate functional group.

The silicone macromers may be chosen, by way of non-limiting example, from polysiloxanes comprising a functionalized group, at the end of the polysiloxane chain or close to the end of the chain, chosen from alcohols, thiols, epoxy compounds, and primary and secondary amines, such as those of formula (VIII):

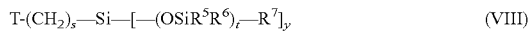

$$T\text{-}(CH_2)_s\text{---}Si\text{---}[\text{---}(OSiR^5R^6)_t\text{---}R^7]_y \quad (VIII)$$

wherein T is chosen from $NH_2$, NHR', epoxy functional groups, OH, and SH; $R^5$, $R^6$, $R^7$, and R', which may be identical or different, are chosen from $C_1$-$C_6$ alkyl, phenyl, benzyl, $C_6$-$C_{12}$ alkylphenyl, and hydrogen; s is a number ranging from 2 to 100; t is a number ranging from 0 to 1000 and y is a number ranging from 1 to 3. These macromers may have a number-average molecular weight ranging, for example, from 5000 to 300 000, such as from 8000 to 200 000, or from 9000 to 40 000.

According to one embodiment, the at least one grafted silicone polymer comprising a polysiloxane backbone grafted by nonsilicone organic monomers comprises a main silicone (or polysiloxane ≡(Si—O—)$_n$) chain onto which is grafted, within the chain and optionally at least one of its ends, at least one organic group not comprising silicone.

According to another embodiment, the silicone polymer comprising a polysiloxane backbone grafted by nonsilicone organic monomers comprises the result of the radical copolymerization between, at least one anionic nonsilicone organic monomer exhibiting an ethylenic unsaturation and/or one hydrophobic nonsilicone organic monomer exhibiting an ethylenic unsaturation and a silicone exhibiting, in its chain, at least one functional group, and in at least one embodiment, several functional groups, capable of reacting with the ethylenic unsaturations of the nonsilicone monomers with the formation of a covalent bond, for example, thio-functional groups.

According to a further embodiment, the anionic monomers possessing ethylenic unsaturation are chosen from unsaturated, linear and branched, carboxylic acids optionally partially or completely neutralized in the form of a salt and mixtures thereof, such as acrylic acid, methacrylic acid, maleic acid, maleic anhydride, itaconic acid, fumaric acid, and crotonic acid. Suitable salts include, for example, alkali metal, alkaline earth metal, and ammonium salts. It should be noted that in the final grafted silicone polymer, the organic group possessing an anionic nature which comprises the result of the radical (homo)polymerization of at least one anionic monomer of unsaturated carboxylic acid type can, after reaction, be postneutralized with a base (e.g., sodium hydroxide, ammonia, and the like) in order to convert it to the form of a salt.

According to a still further embodiment, the hydrophobic monomers comprising ethylenic unsaturation are chosen from alkanol acrylic acid esters and/or alkanol methacrylic acid esters and mixtures thereof. The alkanols may be chosen, for example, from $C_1$-$C_{18}$, such as $C_1$-$C_{12}$, alkanols. Non-limiting examples of such monomers include isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate, stearyl (meth)acrylate, and mixtures thereof.

Examples of silicone polymers comprising a polysiloxane backbone grafted by nonsilicone organic monomers include, but are not limited to, silicone polymers comprising, in their structure, at least one unit chosen from units of structure (IXb) and of structure (IX) and/or (IXa):

wherein the $G_1$ radicals, which may be identical or different, are chosen from hydrogen, $C_1$-$C_{10}$ alkyl radicals, and phenyl radicals; the $G_2$ radicals, which may be identical or different, are chosen from $C_1$-$C_{10}$ alkylene groups; $G_3$ is chosen from polymer residues resulting from the (homo)polymerization of at least one anionic monomer comprising ethylenic unsaturation; $G_4$ is chosen from polymer residues resulting from the (homo)polymerization of at least one monomer of at least one hydrophobic monomer comprising ethylenic unsaturation; m and n, which may be identical or different, are equal to 0 or 1; a is an integer ranging from 0 to 50; b is an integer ranging from 10 to 350 and c is an integer ranging from 0 to 50; with the proviso that one of the parameters a and c is other than 0.

In at least one embodiment, the unit of formula (IX) above exhibits at least one, or all, of the following characteristics:
- the $G_1$ radicals are chosen from alkyl radicals, and in at least one embodiment, methyl radicals;
- n is not equal to zero and the $G_2$ radicals are chosen from divalent $C_1$-$C_3$ radicals, and in at least one embodiment, propylene radicals;
- $G_3$ is chosen from polymer radicals resulting from the (homo)polymerization of at least one monomer of the carboxylic acid comprising ethylenic unsaturation type, and in at least one embodiment, acrylic acid and/or methacrylic acid; and/or
- $G_4$ is chosen from polymer radicals resulting from the (homo)polymerization of at least one monomer of the $C_1$-$C_{10}$ alkyl (meth)acrylate type, and in at least one embodiment, at least one monomer chosen from isobutyl (meth)acrylate and methyl (meth)acrylate.

Examples of silicone polymers corresponding to the formula (VI) include, but are not limited to, polydimethylsiloxanes (PDMSs) onto which are grafted, via a connecting sequence of thiopropylene type, mixed polymer units of the poly(meth)acrylic acid type and of the poly(alkyl (meth)acrylate) type. A non-limiting example of a compound corresponding to this definition is polydimethyl/methylsiloxane comprising propyl thio-3 methyl acrylate/methyl methacrylate/methacrylic acid groups or Polysilicone-8 sold under the name VS80 by 3M.

Other examples of silicone polymers corresponding to the formula (VI) include, but are not limited to, polydimethylsiloxanes (PDMSs) onto which are grafted, via a connecting sequence of thiopropylene type, polymer units of the poly(isobutyl (meth)acrylate) type.

According to one embodiment, the number-average molecular weight of the silicone polymers comprising a polysiloxane backbone grafted by nonsilicone organic monomers of the present disclosure ranges from 10 000 to 1 000 000, for example, from 10 000 to 100 000.

In another embodiment, the grafted silicone polymers are chosen from alkyl methacrylate copolymer grafted by polydimethylsiloxane, copolymers of isobutyl methacrylate, of acrylic acid, and of silicone macromer and polydimethyl/methylsiloxane comprising propyl thio-3 methyl acrylate/methyl methacrylate/methacrylic acid groups.

The composition of the present disclosure may further comprise a crosslinked silicone, such as crosslinked organopolysiloxane elastomers, silicone compounds of high molecular weight exhibiting a three-dimensional structure, with the viscoelastic properties of a flexible solid material. This material is capable of returning to its original shape after it has been stretched. This elastomer is formed of polymer chains of high molecular weight, the mobility of which is limited by a uniform network of crosslinking points. These compounds have the property of absorbing certain solvents, for instance, silicone solvents, and thus of thickening them, while conferring, on the composition, very good cosmetic qualities, such as spreading qualities.

These organopolysiloxanes can thus be provided in the dry powder form or in the form swollen in a solvent, the resultant product generally being a gel. These products can also be provided in the form dispersed in an aqueous solution. The synthesis of these organopolysiloxanes is described, for example, in U.S. Pat. Nos. 5,266,321, 4,742,142, and 5,654,362, and French Patent Application No. 2 864 784.

The organopolysiloxane elastomers used in the composition may be partially or completely crosslinked. They may be provided in the form of particles. In at least one embodiment, the particles of organopolysiloxane elastomer may have a number-average size ranging from 0.1 to 500 μm, for example, from 3 to 200 μm, or from 3 to 50 μm. These particles can have any shape, for example, spherical, flat, and amorphous.

The crosslinked organopolysiloxane elastomer can be obtained, for example, by a reaction chosen from a crosslinking addition reaction of a diorganopolysiloxane comprising at least one hydrogen atom bonded to a silicon atom and a diorganopolysiloxane having at least two groups comprising ethylenic unsaturation bonded to separate silicon atoms, for instance, in the presence of a platinum catalyst; a crosslinking condensation/dehydrogenation reaction between a diorganopolysiloxane comprising hydroxyl endings and a diorganopolysiloxane comprising at least one hydrogen atom bonded to a silicon atom, for instance, in the presence of an organotin compound; a crosslinking condensation reaction of a diorganopolysiloxane comprising hydroxyl endings and of a hydrolysable organopolysilane; thermal crosslinking of an organopolysiloxane, for instance, in the presence of an organoperoxide catalyst; and crosslinking of an organopolysiloxane by high energy radiation, such as gamma rays, ultraviolet rays, and an electron beam.

In at least one embodiment, the crosslinked organopolysiloxane elastomer is obtained by a crosslinking addition reaction of a diorganopolysiloxane (X) comprising at least one hydrogen atom bonded to a silicon atom and of a diorganopolysiloxane (XI) having at least two groups comprising ethylenic unsaturation each bonded to a separate silicon atom, for instance, in the presence of a platinum catalyst (XII), as described, for example, in European Patent Application No. 0 295 886.

The compound (X) may be chosen, by way of non-limiting example, from organopolysiloxanes having at least two hydrogen atoms bonded to separate silicon atoms in each molecule. The compound (X) can exhibit any molecular structure, for example, a structure chosen from linear chain, branched chain, and cyclic structures. According to one embodiment, the compound (X) may have a viscosity of 25° C. ranging from 1 to 50 000 centistokes, which may advantageously make it highly miscible with the compound (XI).

The organic groups bonded to the silicon atoms of the compound (X) may be chosen, for example, from alkyl groups, such as methyl, ethyl, propyl, butyl, and octyl; substituted alkyl groups, such as 2-phenylethyl, 2-phenylpropyl, and 3,3,3-trifluoropropyl; aryl groups, such as phenyl, tolyl, and xylyl; substituted aryl groups, such as phenylethyl; and substituted monovalent hydrocarbon groups, such as epoxy groups, carboxylate ester groups, and mercapto groups. Thus, in at least one embodiment, the compound (X) may be chosen from methylhydropolysiloxanes comprising trimethylsiloxy endings, dimethylsiloxane/methylhydrosiloxane copolymers comprising trimethylsiloxy endings, and dimethylsiloxane/methylhydrosiloxane cyclic copolymers.

The compound (XI) may be chosen, by way of non-limiting example, from diorganopolysiloxanes having at least two lower (for example $C_2$-$C_4$) alkenyl groups; wherein the lower alkenyl group may be chosen from vinyl, allyl, and propenyl groups. These lower alkenyl groups may be situated in any position on the organopolysiloxane molecule, for example, they may be situated at the ends of the organopolysiloxane molecule.

The organopolysiloxane (XI) may have a structure chosen from branched-chain, linear-chain, cyclic, and network structures. In at least one embodiment, it has a linear-chain structure. In at least one embodiment, the compound (XI) may have a viscosity ranging from the liquid state to the gum state. In another embodiment, the compound (XI) has a viscosity of at least 100 centistokes at 25° C. In addition to the abovementioned alkenyl groups, the other organic groups bonded to the silicon atoms in the compound (XI) may be chosen from alkyl groups, such as methyl, ethyl, propyl, butyl, and octyl; substituted alkyl groups, such as 2-phenylethyl, 2-phenylpropyl, and 3,3,3-trifluoropropyl; aryl groups, such as phenyl, tolyl, and xylyl; substituted aryl groups, such as phenylethyl; and substituted monovalent hydrocarbon groups, such as epoxy groups, carboxylate ester groups, and mercapto groups.

In at least one embodiment, the organopolysiloxanes (XI) can be chosen from methylvinylpolysiloxanes, methylvinylsiloxane/dimethylsiloxane copolymers, dimethylpolysiloxanes comprising dimethylvinylsiloxy endings, dimethylsiloxane/methylphenylsiloxane copolymers comprising dimethylvinylsiloxy endings, dimethylsiloxane/diphenylsiloxane/methylvinylsiloxane copolymers comprising dimethylvinylsiloxy endings, dimethylsiloxane/methylvinylsiloxane copolymers comprising trimethylsiloxy endings, dimethylsiloxane/methylphenylsiloxane/methylvinylsiloxane copolymers comprising trimethylsiloxy endings, methyl(3,3,3-trifluoropropyl)polysiloxanes comprising dimethylvinylsiloxy endings, and dimethylsiloxane/methyl(3,3,3-trifluoropropyl)siloxane copolymers comprising dimethylvinylsiloxy endings. In another embodiment, the organopolysiloxane elastomer can be obtained by reaction of a dimethylpolysiloxane comprising dimethylvinylsiloxy endings and of a methylhydropolysiloxane comprising trimethylsiloxy endings in the presence of a platinum catalyst.

According to one embodiment, the sum of the number of ethylenic groups per molecule of the compound (XI) and the number of hydrogen atoms bonded to silicon atoms per molecule of the compound (X) is at least 5.

In another embodiment, the compound (X) is added in an amount such that the molecular ratio of the total amount of hydrogen atoms bonded to silicon atoms in the compound (X) to the total amount of all the groups comprising ethylenic unsaturation in the compound (XI) ranges from 1.5/1 to 20/1.

The compound (XII) is the catalyst of the crosslinking reaction and, in at least one embodiment, may be chosen from chloroplatinic acid, chloroplatinic acid/olefin complexes, chloroplatinic acid/alkenylsiloxane complexes, chloroplatinic acid/diketone complexes, platinum black, and platinum-on-support. The catalyst (XII) may be present in an amount ranging from 0.1 to 1000 parts by weight, better for example, from 1 to 100 parts by weight, as platinum metal proper per 1000 parts by weight of the total amount of the compounds (X) and (XI).

The crosslinked organopolysiloxane compound obtained may be chosen from nonemulsifying and emulsifying crosslinked organopolysiloxane compounds. As used herein, the term "nonemulsifying" defines crosslinked organopolysiloxanes not comprising polyoxyalkylene units. As used herein, the term "emulsifying" means crosslinked organopolysiloxane compounds having at least one polyoxyalkylene unit, for example, polyoxyethylene and polyoxypropylene units.

The crosslinked organopolysiloxane particles may be conveyed, for example, in the form of a gel comprising at least one crosslinked organopolysiloxane included in at least one hydrocarbon oil and/or one silicone oil. In these gels, the organopolysiloxane particles are often nonspherical particles. The crosslinked organopolysiloxane particles may also be provided in the form of a powder, for example, in the form of a spherical powder.

Nonemulsifying crosslinked organopolysiloxanes are described, for instance, in U.S. Pat. Nos. 4,970,252, 4,987,169, 5,412,004, 5,654,362, and 5,760,116 and Japanese Patent Application No. 61-194009.

Non-limiting examples of nonemulsifying crosslinked organopolysiloxanes include those sold under the names "KSG-6", "KSG-1 5", "KSG-16", "KSG-18", "KSG-31", "KSG-32", "KSG-33", "KSG-41", "KSG-42", "KSG-43", "KSG-44", and "USG-103" by Shin-Etsu, "DC 9040", "DC 9041", "DC 9509", "DC 9505", "DC 9506", and "DC 9045" by Dow Corning, "Gransil" by Grant Industries, and "SFE 839" by General Electric.

According to one embodiment, the emulsifying crosslinked organopolysiloxanes comprise the polyoxyalkylene-modified organopolysiloxanes formed from divinyl compounds, such as polysiloxanes having at least two vinyl groups, reacting with Si—H bonds of a polysiloxane. Emulsifying crosslinked organopolysiloxanes are described, for example, in U.S. Pat. Nos. 5,236,986, 5,412,004, 5,837,793, and 5,811,487.

Examples of emulsifying crosslinked organopolysiloxanes include, but are not limited to, those sold under their names "KSG-21", "KSG-20", "KSG-30", and X-226146" by Shin-Etsu and "DC9010" and "DC9011" by Dow Corning.

The crosslinked organopolysiloxane elastomer particles can also be provided in the form of a crosslinked organopolysiloxane elastomer powder coated with silicone resin, such as silsesquioxane resin, as described, for example, in U.S. Pat. No. 5,538,793.

Such elastomers are sold, for instance, under the names "KSP-100", "KSP-101", "KSP-102", "KSP-103", "KSP-104", and "KSP-1 05" by Shin-Etsu.

Other crosslinked organopolysiloxane elastomers in the form of powders include, but are not limited to, powders formed of hybrid silicone functionalized by fluoroalkyl groups, sold, for example, under the name "KSP-200" by Shin-Etsu; and powders formed of hybrid silicones functionalized by phenyl groups, sold, for instance, under the name "KSP-300" by Shin-Etsu.

Other examples of crosslinked organopolysiloxanes include, but are not limited to, dispersions of powders in water in the presence or absence of an emulsifying agent, such as the compounds BY29-119, DC2-1997, EPSX001B, EPSX002B, and EPSX004A from Dow Corning.

When it is present in the composition of the present disclosure, the at least one polysiloxane having a viscosity of greater than 100 cSt may be present in an amount ranging from 0.1% to 30% by weight, for example, from 0.1% to 20% by weight, or from 0.1% to 10% by weight.

The composition of the present disclosure may further comprise at least one nonsilicone polymer which may make it possible to improve either the intrinsic properties of the composition and/or the sheathing obtained during application to the individual hair.

Such a polymer may be chosen, for example, from:
polymers soluble in a liquid organic medium, such as fat-soluble polymers;
polymers dispersible in an organic solvent medium, such as polymers in the form of nonaqueous dispersions of polymer particles with a primary size of less than 1 μm, for instance, dispersions in silicone and dispersions in hydrocarbon oils;

polymers in the form of aqueous dispersions of polymer particles with a primary size of less than 1 μm, often known as "latexes"; in this case, the composition comprises an aqueous phase; and water-soluble polymers; in this case, the composition comprises an aqueous phase or else the polymer is applied in pre- or posttreatment with regard to the PDMS/polyurea copolymer.

The polymer which can be used in the composition may be chosen from anionic, cationic, nonionic, and amphoteric polymers.

Anionic Polymers

Examples of suitable anionic polymers include, but are not limited to, polymers including at least one group chosen from groups derived from carboxylic, sulphonic, and phosphoric acid and which have a number-average molecular weight ranging from 500 to 5 000 000.

The carboxyl groups may be contributed by unsaturated mono- and dicarboxylic acid monomers, such as those of the following formula:

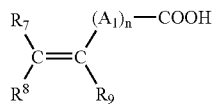

wherein n is an integer ranging from 0 to 10; $A_1$ is a methylene group, optionally connected to the carbon atom of the unsaturated group or to the neighboring methylene group when n is greater than 1 via a heteroatom, such as oxygen and sulphur; $R_7$ is chosen from hydrogen, phenyl, and benzyl groups, $R_8$ is chosen from hydrogen, lower alkyl and carboxyl groups; and $R_9$ is chosen from hydrogen, lower alkyl, —$CH_2$—COOH, phenyl, and benzyl groups.

In the abovementioned formula, a lower alkyl group may be chosen, for example, from groups comprising from 1 to 4 carbon atoms, such as methyl and ethyl groups.

Non-limiting examples of anionic polymers comprising carboxyl groups suitable for use in accordance with the present disclosure include:

A) Homo- and copolymers of acrylic and methacrylic acid and their salts, for example, the products sold under the names Versicol® E and K by Allied Colloid and Ultrahold® by BASF, the copolymers of acrylic acid and of acrylamide sold in the form of their sodium salts under the names Reten 421, 423, or 425 by Hercules, and the sodium salts of polyhydroxycarboxylic acids.

B) Copolymers of acrylic and methacrylic acid with a monoethylenic monomer, such as ethylene, styrene, vinyl esters and, esters of acrylic or methacrylic acid, optionally grafted onto a polyalkylene glycol, such as polyethylene glycol, and optionally crosslinked. Such polymers are described for example, in French Patent No. 1 222 944 and German Patent Application No. 2 330 956, the copolymers of this type comprising, in their chain, an optionally N-alkylated and/or -hydroxyalkylated acrylamide unit, such as those described in Luxembourgian Patent Applications Nos. 75370 and 75371 and those sold under the name Quadramer by American Cyanamid. Further non-limiting examples include copolymers of acrylic acid and of $C_1$-$C_4$ alkyl methacrylate and terpolymers of vinylpyrrolidone, of acrylic acid, and of $C_1$-$C_{20}$ alkyl methacrylate, for example, lauryl methacrylate, such as that sold by ISP under the name Acrylidone® LM, and methacrylic acid/ethyl acrylate/tert-butyl acrylate terpolymers, such as the product sold under the name Luvimer® 100 P by BASF.

Additional suitable anionic polymers include, but are not limited to, the methacrylic acid/acrylic acid/ethyl acrylate/methyl methacrylate copolymers in aqueous dispersion sold under the name Amerhold® DR 25 by Amerchol.

C) Copolymers of crotonic acid, such as those comprising, in their chain, at least one unit chosen from vinyl acetate and propionate units and optionally other monomers, such as allyl and methallyl esters, vinyl ethers and vinyl esters of linear or branched saturated carboxylic acids comprising a long hydrocarbon chain, such as those comprising at least 5 carbon atoms, it optionally being possible for these polymers to be grafted or crosslinked, and optionally other monomers, such as vinyl, allyl, and methallyl esters of α- and β-cyclic carboxylic acids. Such polymers are described, for example, in French Patent Nos. 1 222 944, 1 580 545, 2 265 782, 2 265 781, 1 564 110, and 2 439 798. Commercial products coming within this class include, but are not limited to, Resins 28-29-30, 26-13-14, and 28-13-10 sold by National Starch.

D) Copolymers of $C_4$-$C_8$ monounsaturated carboxylic acids and anhydrides chosen from:

copolymers comprising (i) at least one unit chosen from more maleic, fumaric, and itaconic acids and anhydrides and (ii) at least one monomer chosen from vinyl esters, vinyl ethers, vinyl halides, phenylvinyl derivatives, and acrylic acid and its esters, the anhydride functional groups of these copolymers optionally being monoesterified or monoamidated. Such polymers are described, for example, in U.S. Pat. Nos. 2,047,398, 2,723,248, and 2,102,113 and British Patent No. 839 805. Examples of suitable commercial products include, but are not limited to, those sold under the names Gantrez® AN and ES by ISP; and copolymers comprising (i) at least one unit chosen from maleic, citraconic, and itaconic anhydride units and (ii) at least one monomer chosen from allyl and methallyl esters, optionally comprising at least one group chosen from acrylamide, methacrylamide, x-olefin, acrylic and methacrylic ester, acrylic and methacrylic acid, and vinylpyrrolidone groups in their chain, the anhydride functional groups of these copolymers optionally being monoesterified or monoamidated.

These polymers are described, for example, in French Patent Nos. 2 350 384 and 2 357 241.

E) Polyacrylamides comprising carboxylate groups.

The homopolymers and copolymers comprising sulpho groups may be chosen, for instance, from polymers comprising vinylsulphonic, styrenesulphonic, naphthalenesulphonic, and acrylamidoalkylsulphonic units.

These polymers may include, for example:

salts of polyvinylsulphonic acid having a molecular weight ranging from 1000 to 100 000, and copolymers with an unsaturated comonomer, such as acrylic and methacrylic acids and their esters, acrylamide and its derivatives, vinyl ethers, and vinylpyrrolidone;

salts of polystyrenesulphonic acid, such as the sodium salts sold, for example, under the names Flexan® 500 and Flexan® 130 by National Starch. These compounds are described, for example, in French Patent No. 2 198 719;

salts of polyacrylamidosulphonic acids, such as those described in U.S. Pat. No. 4,128,631, for example, the polyacrylamidoethylpropanesulphonic acid sold under the name Cosmedia Polymer HSP 1180 by Henkel; and sulphonic polyesters. As used herein, the term "sulphonic polyesters" is understood to mean copolyesters obtained by polycondensation of at least one dicarboxylic acid or of one of its esters, of at least one diol, and of at least one sulphoaryldicarboxyl difunctional compound substituted on the aromatic nucleus by an —$SO_3M$ group in which M is chosen from hydrogen and metal ions, such as $Na^+$, $Li^+$, and $K^+$.

Water-dispersible sulphonic polyesters generally have a weight-average molecular weight ranging from 1000 to 60 000, for example, from 4000 to 20 000, as determined by gel permeation chromatography (or GPC).

The glass transition temperature of these sulphonic polyesters generally ranges from 10° C. to 100° C., for instance, from 25° C. to 60° C.

These sulphonic polyesters are described, for example, in U.S. Pat. Nos. 3,734,874, 3,779,993, 4,119,680, 4,300,580, 4,973,656, 5,660,816, 5,662,893, and 5,674,479.

The sulphonic polyesters useful in accordance with one embodiment of the present disclosure comprise at least units derived from isophthalic acid, from salts of sulphoaryldicarboxylic acid, and from diethylene glycol. In another embodiment, the sulphonic polyesters are obtained from isophthalic acid, from sodium salt of sulphoisophthalic acid, from diethylene glycol, and from 1,4-cyclohexanedimethanol.

Examples of sulphonic polyesters include, but are not limited to, those known under the INCI name Diglycol/CHDM/Isophthalates/SIP and sold under the trade name Eastman AQ® by Eastman Chemical, such as Eastman AQ 48®.

Other non-limiting anionic polymers which can be used in accordance with the present disclosure include anionic branched block polymers sold under the name Fixate G-100 by Noveon.

Further examples of anionic polymers include, but are not limited to, optionally functionalized anionic polyurethanes which may or may not comprise silicone.

Such polyurethanes may be chosen, for example, from those described in European Patent Application Nos. 0 751 162, 0 637 600, 0 648 485, 0 656 021, and 0 619 111, French Patent Application Nos. 2 743 297, and International Patent Application Publication No. WO 94/03510.

According to one embodiment, the polyurethanes may be chosen from the products sold under the names Luviset PUR® and Luviset® Si PUR by BASF.

The anionic polymers may also include branched block copolymers comprising, as main monomers, at least one $C_{1-20}$ alkyl acrylate and/or at least one N-mono- or N,N-di ($C_{2-12}$ alkyl)(meth)acrylamide, and acrylic acid and/or methacrylic acid.

These branched sequential (or block) copolymers exhibit a structure composed of hydrophobic blocks to which are attached, for example, via bifunctional units, a certain number of more hydrophilic blocks. These copolymers exhibit at least two glass transition temperatures.

According to one embodiment, these copolymers may comprise:
from 26 to 36 mol % of acrylic acid;
from 27.5 to 30.5 mol % of n-butyl acrylate;
from 33.3 to 45.3 mol % of methacrylic acid; and
from 0.48 to 0.92 mol % of allyl methacrylate The hydrophobic blocks may have a molecular weight ranging from 10 000 to 100 000 and the hydrophilic blocks may have a molecular weight ranging from 1000 to 100 000 daltons.

The above polymers are in the anionic form, that is to say that they are converted to salts by partial or complete neutralization of the (meth)acrylic acid groups. Examples of suitable neutralizing agents include, but are not limited to, 2-amino-2-methyl-1-propanol and sodium hydroxide.

Such polymers are described, for instance, in International Patent Application Publication No. WO 00/40628 and are sold, for example, under the names EX-SDR-26® and EX-SDR-45® by Goodrich.

According to one embodiment, the anionic polymers are chosen from acrylic acid copolymers, such as the acrylic acid/ethyl acrylate/N-tert-butylacrylamide terpolymers sold under the name Ultrahold® Strong by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by National Starch, polymers derived from maleic, fumaric, and itaconic acids and anhydrides with vinyl esters, vinyl ethers, vinyl halides, phenylvinyl derivatives, and acrylic acid and its esters, such as the monoesterified methyl vinyl ether/maleic anhydride copolymers sold, for example, under the name Gantrez® by ISP, the copolymers of methacrylic acid and of methyl methacrylate sold under the name Eudragit® L by Rohm Pharma, the copolymers of methacrylic acid and of ethyl acrylate sold under the name Luvimer® MAEX and MAE by BASF, the vinyl acetate/crotonic acid copolymers sold under the name Luviset CA 66 by BASF and the vinyl acetate/crotonic acid copolymers grafted by polyethylene glycol sold under the name Aristoflex® A by BASF, and the polymer sold under the name Fixate G-100 by Noveon.

According to another embodiment, the anionic polymers are chosen from the monoesterified methyl vinyl ether/maleic anhydride copolymers sold under the name Gantrez® ES 425 by ISP, the acrylic acid/ethyl acrylate/N-tert-butylacrylamide terpolymers sold under the name Ultrahold® Strong by BASF, the copolymers of methacrylic acid and of methyl methacrylate sold under the name Eudragit® L by Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by National Starch, the copolymers of methacrylic acid and of ethyl acrylate sold under the name Luvimer® MAEX and MAE by BASF, the vinylpyrrolidone/acrylic acid/lauryl methacrylate terpolymers sold under the name Acrylidone® LM by ISP, and the polymer sold under the name Fixate G-100 by Noveon.

Cationic Polymers

Suitable cationic polymers may include, for example, polymers comprising cationic groups and groups which can be ionized to give cationic groups.

Non-limiting examples of such cationic polymers include those which comprise units comprising primary, secondary, tertiary, and/or quaternary amine groups which can either form part of the polymer chain or be carried by a side substituent.

The cationic polymers used may have a molecular weight ranging, for example, from 1000 to $15 \times 10^6$.

According to one embodiment, the cationic polymers may comprise at least 10% by weight of units comprising amine groups and/or quaternary ammonium groups, the degree of quaternization of which, expressed as cationic equivalent per gram of polymer, is, for example, at least 0.05 cationic meq./g (meq.: milliequivalent).

When the cationic polymer carries amine or quaternary ammonium groups carried by a side substituent, the polymer chain may be chosen, for example, from acrylic, vinyl, and peptide chains.

Suitable cationic polymers may include, for example, quaternized proteins and polymers of the polyamine, polyaminoamide, and poly(quaternary ammonium) type.

The polymers can be linear or branched, they may have a structure chosen from block structures, comb structures, and dendritic structures, and/or they may be in the form of a latex in water or in a concentrated saline solution.

Non-limiting examples of quaternized proteins include chemically modified polypeptides carrying quaternary ammonium groups at the chain end or grafted to the chain, for example:

a) collagen hydrolysates carrying triethylammonium groups, such as the products sold under the name "Quat-Pro E" by Maybrook and called, in the CTFA dictionary, "Triethonium Hydrolysed Collagen Ethosulphate";

b) collagen hydrolysates carrying at least one group chosen from trimethylammonium and trimethylstearylammonium chloride groups, sold under the name Quat-Pro S by Maybrook and called, in the CTFA dictionary, "Steartrimonium Hydrolysed Collagen"; and c) protein hydrolysates carrying, on the polypeptide chain, quaternary ammonium groups comprising at least one alkyl radical comprising from 1 to 18 carbon atoms, for example, those sold by Croda: Croquat L, Croquat M, Croquat S, and Crotein Q; and the products sold by Inolex under the name "Lexein QX 3000", called, in the CTFA dictionary, "Cocotrimonium Collagen Hydrolysate".

Further examples of quaternized proteins include quaternized plant proteins, such as wheat, maize, and soya proteins; for example, quaternized wheat proteins, such as those sold by Croda under the names "Hydrotriticum WQ and QM", called, in the CTFA dictionary, "Cocodimonium Hydrolysed Wheat Protein", "Hydrotriticum QL", called, in the CTFA dictionary, "Laurdimonium Hydrolysed Wheat Protein", and "Hydrotriticum QS", called, in the CTFA dictionary, "Steardimonium Hydrolysed Wheat Protein".

Cationic polysaccharides may also be used in the composition of the present disclosure, for example, polysaccharides comprising quaternary ammonium, such as those described in U.S. Pat. Nos. 3,589,578 and 4,031,307, such as guar gums comprising trialkylammonium cationic groups. Such products are sold, for instance, under the trade names of Jaguar C13 S, Jaguar C 15, and Jaguar C 17 by Meyhall.

Other non-limiting examples of cationic polymers include quaternary copolymers of vinylpyrrolidone and of vinylimidazole; cationic cellulose derivatives, such as copolymers of cellulose or of cellulose derivatives grafted with a water-soluble monomer comprising a quaternary ammonium and described, for example, in U.S. Pat. No. 4,131,576, such as hydroxyalkylcelluloses, for instance, hydroxymethyl-, hydroxyethyl-, and hydroxypropylcelluloses, grafted, for example, with a salt chosen from methacryloyloxyethyltrimethylammonium, methacrylamidopropyltrimethylammonium, and dimethyldiallylammonium salts.

Commercial products corresponding to this definition include, but are not limited to, the products sold under the name "Celquat L 200" and "Celquat H 100" by National Starch.

Other non-limiting examples of cationic polymers include polymers of the polyamine, polyaminoamide, and poly(quaternary ammonium) type.

According to one embodiment, these polymers can be chosen, for example, from:

(1) Homopolymers and copolymers derived from acrylic and methacrylic esters and amides comprising at least one unit chosen from those of the following formulas:

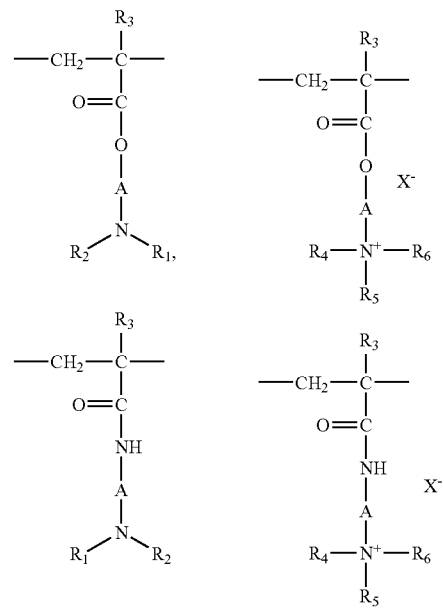

wherein:

$R_3$, which may be identical or different, are chosen from hydrogen and $CH_3$ radicals;

A, which may be identical or different, are chosen from linear and branched alkyl groups comprising from 1 to 6 carbon atoms, for example, 2 or 3 carbon atoms, and hydroxyalkyl groups comprising from 1 to 4 carbon atoms;

$R_4$, $R_5$, and $R_6$, which may be identical or different, are chosen from alkyl groups comprising from 1 to 18 carbon atoms and benzyl radicals, and in at least one embodiment, alkyl groups comprising from 1 to 6 carbon atoms;

$R_1$ and $R_2$, which may be identical or different, are chosen from hydrogen and alkyl groups comprising from 1 to 6 carbon atoms, such as methyl and ethyl; and X is chosen from anions derived from inorganic and organic acids, such as methosulphate anions and halides, for example, chloride and bromide.

The copolymers of family (1) may further comprise at least one unit derived from monomers chosen from acrylamides, methacrylamides, diacetone acrylamides, acrylamides and methacrylamides substituted on the nitrogen by lower ($C_1$-$C_4$) alkyls, acrylic and methacrylic acids and their esters, vinyllactams, such as vinylpyrrolidone and vinylcaprolactam, and vinyl esters.

Thus, suitable examples of copolymers of family (1) include, but are not limited to:

copolymers of acrylamide and of dimethylaminoethyl methacrylate which is quaternized with dimethyl sulphate or with a methyl halide, such as the product sold under the name Hercofloc by Hercules, copolymers of acrylamide and of methacryloyloxyethyltrimethylammonium chloride, described, for example, in European Patent Application No. 0 080 976 and sold under the name Bina Quat P 100 by Ciba-Geigy, the copolymers of acrylamide and of methacryloyloxyethyltrimethylammonium methosulphate sold under the name Reten by Hercules, vinylpyrrolidone/dialkylaminoalkyl acrylate and methacrylate copolymers, which may or may not be quaternized described, for example, in French Patent Nos. 2 077 143 and 2 393 573 and sold, for instance, under the name "Gafquat" by GAF Corporation, such as "Gafquat 734 and 755", and the product known as "Copolymer 937", polymers comprising a fatty chain and comprising a vinylpyrrolidone unit, such as the products sold under the names Styleze W20 and Styleze W10 by ISP, dimethylaminoethyl methacrylate/vinylcaprolactam/vinylpyrrolidone terpolymers, such as the product sold under the name Gaffix VC 713 by ISP, and vinylpyrrolidone/quaternized dimethylaminopropylmethacrylamide copolymers, such as the products sold under the name "Gafquat® HS 100" by ISP.

(2) Polymers composed of piperazinyl units and of at least one radical chosen from divalent, straight-, and branched-chain alkylene and hydroxyalkylene radicals, optionally interrupted by at least one entity chosen from oxygen, sulphur, and nitrogen atoms and aromatic and heterocyclic rings, as well as the oxidation and/or quaternization products of these polymers. Such polymers are described, for example, in French Patent Nos. 2 162 025 and 2 280 361.

(3) Water-soluble polyaminoamides prepared, for example, by polycondensation of an acidic compound with a polyamine; these polyaminoamides can be crosslinked by at least one agent chosen from epihalohydrins, diepoxides, dianhydrides, unsaturated dianhydrides, bisunsaturated derivatives, bishalohydrins, bisazetidiniums, bishaloacyidiamines, alkyl bishalides, and oligomers resulting from the reaction of a bifunctional compound reactive with a bishalohydrin, a bisazetidinium, a bishaloacyidiamine, an alkyl bishalide, an epihalohydrin, a diepoxide, and/or a bisunsaturated derivative; the at least one crosslinking agent being present in an amount ranging from 0.025 to 0.35 mol per amine group of the polyaminoamide; these polyaminoamides can be alkylated or, if they comprise at least one tertiary amine functional groups, quaternized. Such polymers are described, for instance, in French Patent Nos. 2 252 840 and 2 368 508.

(4) Polyaminoamide derivatives resulting from the condensation of polyalkylenepolyamines with polycarboxylic acids, followed by an alkylation by bifunctional agents, for example, adipic acid/dialkylaminohydroxyalkyldialkylenetriamine polymers in which the alkyl radical comprises from 1 to 4 carbon atoms, such as methyl, ethyl, and propyl radicals. Such polymers are described, for example, in French Patent No. 1 583 363.

Non-limiting examples of commercial products corresponding to these derivatives include the adipic acid/dimethylaminohydroxypropyl/diethylenetriamine polymers sold under the names "Cartaretin F, F4, and F8" by Sandoz.

(5) Polymers obtained by reaction of a polyalkylenepolyamine comprising two primary amine groups and at least one secondary amine group with a dicarboxylic acid chosen from diglycolic acid and saturated aliphatic dicarboxylic acids comprising from 3 to 8 carbon atoms, the molar ratio of polyalkylenepolyamine to dicarboxylic acid ranging from 0.8:1 to 1.4:1; the polyaminoamide resulting therefrom being reacted with epichlorohydrin in a molar ratio of epichlorohydrin in relation to the secondary amine group of the polyaminoamide ranging from 0.5:1 to 1.8:1. Such polymers are described, for example, in U.S. Pat. Nos. 3,227,615 and 2,961,347.

Polymers of this type are sold, for example, under the name "Hercosett 57" by Hercules Inc. in the case of the adipic acid/epoxypropyl/diethylenetriamine copolymer.

(6) Cyclopolymers of alkyldiallylamine and of dialkyldiallylammonium, such as the homopolymers and copolymers comprising, as main constituent of the chain, units chosen from those of formulas (I) and (I'):

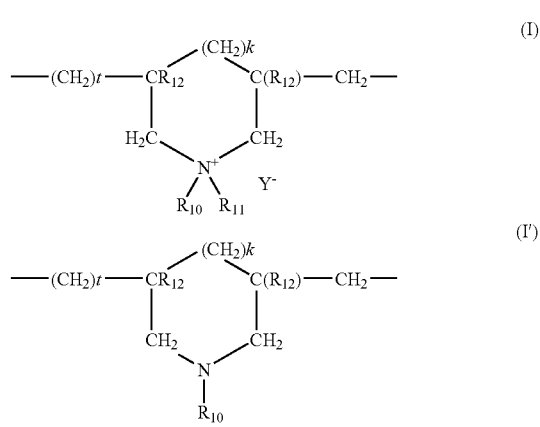

wherein k and t are equal to 0 or 1, the sum k+t being equal to 1; $R_{12}$ is chosen from hydrogen and methyl radicals; $R_{10}$ and $R_{11}$, which may be identical or different, are chosen from alkyl groups comprising from 1 to 6 carbon atoms, hydroxyalkyl groups in which the alkyl group comprises from 1 to 5 carbon atoms, and lower ($C_1$-$C_4$) amidoalkyl groups; or alternatively, $R_{10}$ and $R_{11}$ may form, together with the nitrogen atom to which they are attached, heterocyclic groups, such as piperidinyl and morpholinyl; $Y^-$ is an anion, such as bromide, chloride, acetate, borate, citrate, tartrate, bisulphate, bisulphite, sulphate, and phosphate. These polymers are described, for example, in French Patent No. 2 080 759 and its certificate of addition 2 190 406.

In at least one embodiment, $R_{10}$ and $R_{11}$, which may be identical or different, are chosen from alkyl groups comprising from 1 to 4 carbon atoms.

Non-limiting examples of the polymers defined above include the homopolymer of dimethyldiallylammonium chloride sold under the name "Merquat 100" by Nalco (and its homologues of low weight-average molar masses) and of the copolymers of diallyldimethylammonium chloride and of acrylamide.

(7) The quaternary diammonium polymers comprising repeat units corresponding to the formula (II):

wherein:

R$_{13}$, R$_{14}$, R$_{15}$, and R$_{16}$, which may be identical or different, are chosen from aliphatic, alicyclic, and arylaliphatic radicals comprising from 1 to 20 carbon atoms and lower aliphatic hydroxyalkyl radicals, or alternatively, R$_{13}$, R$_{14}$, R$_{15}$, and R$_{16}$, together or separately, may form, with the nitrogen atoms to which they are attached, heterocycles optionally comprising a second heteroatom other than nitrogen, or alternatively, R$_{13}$, R$_{14}$, R$_{15}$, and R$_{16}$ are chosen from linear or branched C$_1$-C$_6$ alkyl radicals substituted by at least one group chosen from nitrile, ester, acyl, amide, —CO—O—R$_{17}$-D, and —CO—NH—R$_{17}$-D groups, wherein R$_{17}$ is an alkylene and D is a quaternary ammonium group;

A$_1$ and B$_1$, which may be identical or different, are chosen from polymethylene groups comprising from 2 to 20 carbon atoms which can be linear or branched and saturated or unsaturated, and which can comprise, bonded to or inserted into the main chain, at least one entity chosen from aromatic rings, oxygen and sulphur atoms, sulphoxide groups, sulphone groups, disulphide groups, amino groups, alkylamino groups, hydroxyl groups, quaternary ammonium groups, ureido groups, amide groups, and ester groups, X$^-$ is chosen from anions derived from inorganic and organic acids;

A$_1$, R$_{13}$, and R$_{15}$ can form, together with the two nitrogen atoms to which they are attached, a piperazine ring; and if A$_1$ is chosen from linear or branched and saturated or unsaturated alkylene and hydroxyalkylene radicals, B$_1$ may be a —(CH$_2$)$_n$—CO-D-OC—(CH$_2$)$_n$— group in which D is chosen from:

a) glycol residues of formula: —O—Z—O—, wherein Z is chosen from linear and branched hydrocarbon radicals and groups of the following formulas:

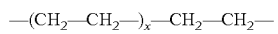

—(CH$_2$—CH$_2$—)$_x$—CH$_2$—CH$_2$—

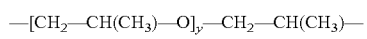

—[CH$_2$—CH(CH$_3$)—O]$_y$—CH$_2$—CH(CH$_3$)— wherein x and y, which may be identical or different, are chosen from integers ranging from 1 to 4, representing a defined and unique degree of polymerization, and numbers ranging from 1 to 4, representing a mean degree of polymerization;

b) bissecondary diamine residues, such as piperazine derivatives;

c) bisprimary diamine residues of formula: —NH—Y—NH—, wherein Y is chosen from linear and branched hydrocarbon radicals and divalent radicals of the following formula:

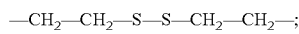

—CH$_2$—CH$_2$—S—S—CH$_2$—CH$_2$—;

d) ureylene groups of formula: —NH—CO—NH—.

According to one embodiment, X is an anion, such as chloride and bromide.

These polymers may have a number-average molar mass generally ranging from 1000 to 100 000.

Polymers of this type are described, for example, in French Patent Nos. 2 320 330, 2 270 846, 2 316 271, 2 336 434, and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

Further non-limiting examples of such polymers include those which comprise at least one repeat unit of formula (a):

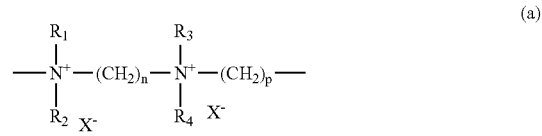

(a)

wherein R$_1$, R$_2$, R$_3$, and R$_4$, which may be identical or different, are chosen from alkyl and hydroxyalkyl radicals comprising from 1 to 4 carbon atoms, n and p are integers ranging from 2 to 20, and X$^-$ is chosen from anions derived from inorganic and organic acids.

In one embodiment, in the compound of formula (a), R$_1$, R$_2$, R$_3$, and R$_4$ are methyl radicals, n=3, p=6, and X=Cl, which corresponds to the compound known as Hexadimethrine chloride according to the INCI (CTFA) nomenclature.

(8) Poly(quaternary ammonium) polymers comprising units of formula (III):

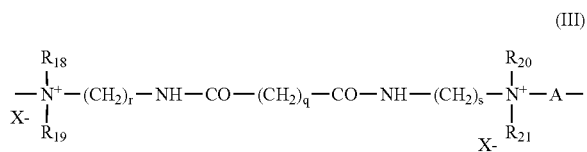

(III)

wherein:

R$_{18}$, R$_{19}$, R$_{20}$, and R$_{21}$, which may be identical or different, are chosen from hydrogen and methyl, ethyl, propyl, β-hydroxyethyl, β-hydroxypropyl, and —CH$_2$CH$_2$(OCH$_2$CH$_2$)$_p$OH radicals, p is an integer ranging from 0 to 6, with the proviso that R$_{18}$, R$_{19}$, R$_{20}$, and R$_{21}$ are not simultaneously hydrogen, r and s, which may be identical or different, are integers ranging from 1 to 6, q is an integer ranging from 0 to 34, X$^-$ is an anion, such as a halide, and A is chosen from radicals of dihalides and —CH$_2$—CH$_2$—O—CH$_2$—CH$_2$—.

Such compounds are described, for instance, in European Patent Application No. 0 122 324.

Examples of commercial products corresponding to these compounds include, but are not limited to, "Mirapol® A 15", "Mirapol AD1", "Mirapol® AZ1", and "Mirapol® 175", sold by Miranol.

(9) Quaternary polymers of vinylpyrrolidone and of vinylimidazole, for example, the products sold under the names Luviquat® FC 905, FC 550, and FC 370 by BASF.

(10) Crosslinked polymers of methacryloyloxy(C$_1$-C$_4$) alkyltri(C$_1$-C$_4$)alkylammonium salts, such as the polymers obtained by homopolymerization of dimethylaminoethyl methacrylate quaternized by methyl chloride or by copolymerization of acrylamide with dimethylaminoethyl methacrylate quaternized by methyl chloride, the homo- or copolymerization being followed by a crosslinking by a compound possessing olefinic unsaturation, for example, methylenebisacrylamide.

(11) Polyalkyleneimines, such as polyethyleneimines and their derivatives. These polymers are described, for example, in European Patent Application No. 1 426 035 and International Patent Application Publication No. WO 2005/092274.

Polyethyleneimines are described, for example, in: "Kirk-Othmer Encyclopedia of Chemical Technology", 3rd edition, vol. 20, 1982, pp. 214-216, and "Polyethyleneimine Prospective Application", H. N. Feigenbaum, Cosmetics & Toiletries, 108, 1993, p. 73.

According to at least one embodiment, the polyethyleneimines (PEI) which can be used in accordance with the present disclosure generally exhibit the following formula:

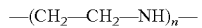

—$(CH_2—CH_2—NH)_n$— wherein n is the mean number of ethyleneimine units, n ranging from 5 to 10 000.

In another embodiment, the ethyleneimine homopolymers can be branched.

Non-limiting examples of such polymers include PEI-7 (n=7), PEI-15 (n=15), PEI-30 (n=30), PEI-45 (n=45), PEI-275 (n=275), PEI-700 (n=700), PEI-1000 (n=1000), PEI-1400 (n=1400), PEI-1500 (n=1500), PEI-1750 (n=1750), and PEI-2500 (n=2500).

Further examples include, but are not limited to, polyethyleneimines of the Lupasol range, such as the products sold under the names Lupasol G35, FG, PS, HF, and P, and Polymin SK from BASF.

The polyethyleneimines (PEI) can be modified by grafts, such as hydrophilic grafts (for example, polyethylene glycol (PEG), polyvinyl acetate (PVA), and polyacrylate) and hydrophobic grafts (for example, silicone and/or $C_8$-$C_{30}$ carbonaceous fatty chains), as described in International Patent Application Publication Nos. WO 97/20879, WO 97/23456, WO 02/095122, and WO 02/15854, U.S. Pat. No. 5,756,080, European Patent No. 0 524 612, and in the publication H. Petersen et al., Macromolecules, 2002, 35, p. 6867.

PEI-PEG compounds are sold, for example, under the names Lupasol SC61B, SC62J, LU158, and HEO1 by BASF.

PEI compounds comprising fatty chains are, for instance, under the names Lupasol ESA 51685 and LU157 by BASF.

12) Polymers Derived from Amino Acids

According to one embodiment, the polymers which can be used in the composition accordance with the present disclosure may be chosen from polymers comprising at least 2 units of at least one basic amino acids.

The at least one basic amino acid may be chosen, for example, from ornithine, aspargine, glutamine, lysine, and arginine. In at least one embodiment, the polymers comprising at least 2 units of the at least one basic amino acid generally comprise from 2 to 10 000 basic amino acid units.

In another embodiment, these polymers can be modified by grafts chosen from hydrophilic grafts (e.g., polyethylene glycol, PVA (polyvinyl acetate), and polyacrylate) and hydrophobic grafts (e.g., PDMS (polydimethylsiloxane comprising $C_8$-$C_{30}$ carbonaceous fatty chains)).

The synthesis of polylysine-PEG is discussed, for example, in GL Kenausis et al., Journal of Physical Chemistry B, 2000, 104, p. 3298.

The synthesis of alkoxylated poly(basic amino acid)s, such as polylysine-polyethylene glycol, is described, for example, in International Patent Application Publication No. WO 00/071601.

Polylysines are also described, for instance, in Japanese Patent Application No. 2003040724.

Further non-limiting examples of polymers include poly-ε-lysine and its silicone derivatives produced by Chisso under the "polylysine" names.

13) Aminated Dendrimers

As used herein, the term "dendrimers comprising primary amines in the terminal position" is understood to mean polymeric compounds comprising a core and base units, monomers or spindles, onto which an end group T carrying a primary amine functional group has been grafted.

Non-limiting examples of polyamidoamine dentrimers include those sold under the commercial reference Starburst PAMAM by Dendritech (block copolymers of ethylenediamine and of methyl acrylate) and those sold under the commercial reference Astromols (DAB) by DSM.

14) Polyallylamines

Examples of polyallylamines include, but are not limited to, those produced by Nitto Boseki Co., and their derivatives, such as those described in International Patent Application Publication No. WO 2005/092274.

Amphoteric Polymers

The polymers which can be used in the composition of the present disclosure may be chosen from amphoteric polymers, such as polymers comprising B and C units distributed randomly in the polymer chain, wherein B is a unit deriving from a monomer comprising at least one basic nitrogen atom and C is a unit deriving from an acidic monomer comprising at least one group chosen from carboxyl and sulpho groups, or alternatively, B and C may be chosen from groups deriving from zwitterionic carboxybetaine and sulphobetaine monomers;

B and C may also be chosen from cationic polymer chains comprising primary, secondary, tertiary, and/or quaternary amine groups, wherein at least one of the amine groups carries at least one group chosen from carboxyl and sulpho groups connected via a hydrocarbon group, or alternatively, B and C may form part of a chain of a polymer comprising an α,β-dicarboxyethylene unit, one of the carboxyl groups of which has been reacted with a polyamine comprising at least one group chosen from primary and secondary amine groups.

Non-limiting examples of amphoteric polymers corresponding to the definition given above include:

1) Copolymers comprising acidic vinyl units and basic vinyl units, such as those resulting from the copolymerization of a monomer derived from a vinyl compound carrying a carboxyl group, such as acrylic acid, methacrylic acid, maleic acid, and α-chloroacrylic acid, and of a basic monomer derived from a substituted vinyl compound comprising at least one basic atom, such as dialkylaminoalkyl methacrylate and acrylate and dialkylaminoalkylmethacrylamide and -acrylamide. Such compounds are described, for example, in U.S. Pat. No. 3,836,537.

2) Polymers comprising units deriving:
   a) from at least one monomer chosen from acrylamides and methacrylamides substituted on the nitrogen atom by an alkyl group,
   b) from at least one acidic comonomer comprising at least one reactive carboxyl group, and
   c) from at least one basic comonomer, such as esters comprising primary, secondary, tertiary, and quaternary amine substituents of acrylic and methacrylic acids and the quaternization product of dimethylaminoethyl methacrylate with dimethyl and diethyl sulphate.

Examples of N-substituted acrylamides and methacrylamides include, but are not limited to, compounds in which the alkyl groups comprise from 2 to 12 carbon atoms, such as N-ethylacrylamide, N-tert-butylacrylamide, N-tert-octylacrylamide, N-octylacrylamide, N-decylacrylamide, and N-dodecylacrylamide, and the corresponding methacrylamides.

The acidic comonomers may be chosen, for example, from acrylic, methacrylic, crotonic, itaconic, maleic, and fumaric acids and alkyl monoesters comprising from 1 to 4 carbon atoms of maleic and fumaric acids and anhydrides.

The basic comonomers may be chosen, for example, from aminoethyl, butylaminoethyl, N,N-dimethylaminoethyl, and N-tert-butylaminoethyl methacrylates.

Examples of suitable copolymers include, but are not limited to, copolymers for which the CTFA name (4th Ed., 1991) is Octylacrylamide/acrylates/butylaminoethyl methacrylate copolymer, such as the products sold under the name Amphomer® and Lovocryl® 47 by National Starch.

(3) Partially or completely acylated and crosslinked polyaminoamides deriving from polyaminoamides of following general formula (II):

(II)

wherein $R_{10}$ is chosen from divalent groups derived from saturated dicarboxylic acids, aliphatic mono- and dicarboxylic acids comprising an ethylenic double bond, esters of lower alkanols comprising from 1 to 6 carbon atoms of these acids, and groups deriving from the addition of any one of the acids with a bisprimary or bissecondary amine, and Z is chosen from groups deriving from bisprimary, mono-, and bissecondary polyalkylenepolyamines and in at least one embodiment, the polyaminoamide comprises:

a) in an amount ranging from 60 to 100 mol %, a group chosen from formula (IV):

(IV)

wherein x=2 and p=2 or 3, or else x=3 and p=2;

this group deriving from an amine chosen from diethylenetriamine, triethylenetetraamine, and dipropylenetriamine;

b) in an amount ranging from 0 to 40 mol %, a group chosen from those of formula (IV), in which x=2 and p=1 and which derives from ethylenediamine and groups deriving from piperazine:

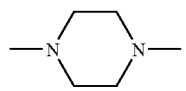

c) in an amount ranging from 0 to 20 mol %, the group —NH—$(CH_2)_6$—NH— deriving from hexamethylenediamine, these polyaminoamides being crosslinked by addition reaction of a bifunctional crosslinking agent chosen from epihalohydrins, diepoxides, dianhydrides, and bisunsaturated derivatives, by means of 0.025 to 0.35 mol of crosslinking agent per amine group of the polyaminoamide, and acylated by reaction with an agent chosen from acrylic acid, chloroacetic acid, alkanesultones and salts thereof.

The saturated carboxylic acids may be chosen, for example, from acids comprising from 6 to 10 carbon atoms, such as adipic, 2,2,4-trimethyladipic, 2,4,4-trimethyladipic, and terephthalic acids, and acids comprising an ethylenic double bond, such as acrylic, methacrylic, and itaconic acids.

Examples of alkanesultones which may be used in the acylation include, but are not limited to, propane- and butanesultone and the salts of the acylating agents may be chosen, for instance, from sodium and potassium salts.

(4) Polymers comprising zwitterionic units of formula (IV):

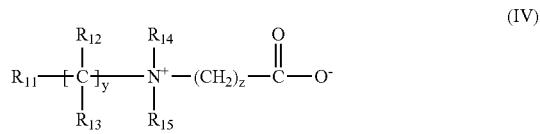

(IV)

wherein $R_{11}$ is a polymerizable unsaturated group, such as acrylate, methacrylate, acrylamide, and methacrylamide groups, y and z, which may be identical or different, are integers ranging from 1 to 3, $R_{12}$ and $R_{13}$, which may be identical or different, are chosen from hydrogen and methyl, ethyl, and propyl groups, and $R_{14}$ and $R_{15}$, which may be identical or different, are chosen from hydrogen and alkyl group such that the sum of the carbon atoms in $R_{14}$ and $R_{15}$ does not exceed 10.

The polymers comprising such units may also comprise units derived from non-zwitterionic monomers, such as dimethyl- and diethylaminoethyl acrylate and methacrylate and alkyl acrylates and methacrylates, acrylamides and methacrylamides, and vinyl acetate.

Non-limiting examples of such polymers include methyl methacrylate/dimethylcarboxymethylammonioethyl methacrylate copolymers, such as the product sold under the name Diaformer Z301 by Sandoz.

(5) Polymers derived from chitosan comprising monomer units corresponding to the following formulas:

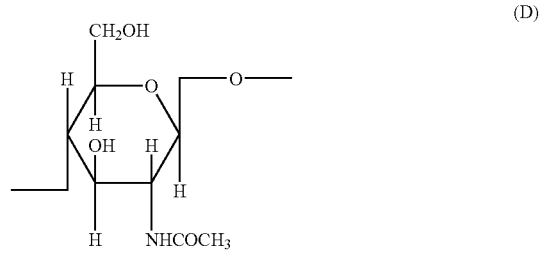

(D)

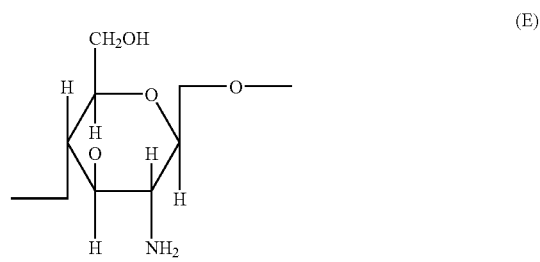

(E)

-continued

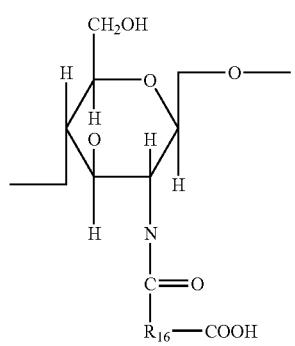
(F)

wherein the unit (D) is present in an amount ranging from 0 to 30%, the unit (E) is present in an amount ranging from 5 to 50%, and the unit (F) is present in an amount ranging from 30 to 90%, it being understood that, in this unit (F), $R_{16}$ is chosen from groups of formula:

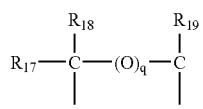

wherein, if q=0, then $R_{17}$, $R_{18}$, and $R_{19}$, which may be identical or different, are chosen from hydrogen, methyl, hydroxyl, acetoxy, and amino residues, monoalkylamino residues, and dialkylamino residues, optionally interrupted by at least one nitrogen atom and/or optionally substituted by at least one group chosen from amino, hydroxyl, carboxyl, alkylthio, and sulpho groups, and alkylthio residues in which the alkyl group carries an amino residue, at least one of the $R_{17}$, $R_{18}$, and $R_{19}$ groups being, in this case, a hydrogen atom, or, if q=1, then $R_{17}$, $R_{18}$, and $R_{19}$ are each hydrogen, and the acid and base addition salts thereof.

(6) Polymers of formula (V), such as those described in French Patent No. 1 400 366 and composed of units:

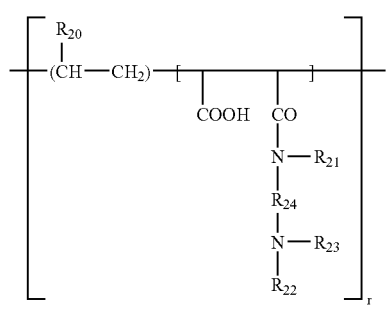
(V)

wherein r is an integer greater than or equal to 1, $R_{20}$ is chosen from hydrogen and $CH_3O$, $CH_3CH_2O$, and phenyl groups, $R_{21}$ is chosen from hydrogen and lower alkyl groups, such as methyl and ethyl, $R_{22}$ is chosen from hydrogen and lower $C_1$-$C_6$ alkyl groups, such as methyl and ethyl, and $R_{23}$ is chosen from lower $C_1$-$C_6$ alkyl groups, such as methyl and ethyl, and groups of the formula: —$R_{24}$—$N(R_{22})_2$, wherein $R_{24}$ is chosen from —$CH_2$—$CH_2$—, —$CH_2$—$CH_2$—$CH_2$—, and —$CH_2$—$CH(CH_3)$— groups and $R_{22}$ is defined as above.

(7) Polymers derived from the N-carboxyalkylation of chitosan, such as the N-(carboxymethyl)chitosan and the N-(carboxybutyl)chitosan sold under the name "Evalsan" by Jan Dekker.

(8) Amphoteric polymers of the -D-X-D-X— type chosen from:
a) polymers obtained by reaction of chloroacetic acid or sodium chloroacetate with compounds comprising at least one unit of formula (VI):

-D-X-D-X-D-     (VI)

wherein D is a group

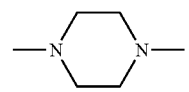

and X is chosen from the symbols E and E', wherein E and E', which may be identical or different, are chosen from bivalent groups which are straight- or branched-chain alkylene groups comprising up to 7 carbon atoms in the main chain which is optionally substituted by hydroxyl groups and which can additionally comprise at least one entity chosen from oxygen, nitrogen, and sulphur atoms and 1 to 3 aromatic and/or heterocyclic rings; the oxygen, nitrogen, and sulphur atoms being present in the form of ether, thioether, sulphoxide, sulphone, sulphonium, alkylamine, alkenylamine, hydroxyl, benzylamine, amine oxide, quaternary ammonium, amide, imide, alcohol, ester, and/or urethane groups.

b) polymers of formula (VI'):

-D-X-D-X—     (VI')

wherein D is a group

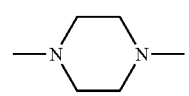

and X is chosen from the symbols E and E' and at least once E', wherein E is defined as above and E' is chosen from bivalent groups which are straight- or branched-chain alkylene groups comprising up to 7 carbon atoms in the main chain which is optionally substituted by at least one hydroxyl group and which comprises at least one nitrogen atom, the nitrogen atom being substituted by an alkyl chain optionally interrupted by an oxygen atom and comprising at least one group chosen from carboxyl functional groups and hydroxyl functional groups and betainized by reaction with an agent chosen from chloroacetic acid and sodium chloroacetate.

(9) ($C_1$-$C_5$)Alkyl vinyl ether/maleic anhydride copolymers partially modified by semiamidation with an N,N-dialkylaminoalkylamine, such as N,N-dimethylaminopropylamine, or by semiesterification with an N,N-dialkylaminoalkanol. These copolymers may also comprise other vinyl comonomers, such as vinylcaprolactam.

According to at least one embodiment, the amphoteric polymers may be chosen from those of family (3), such as the copolymers with the CTFA name of Octylacrylamide/acrylates/butylaminoethyl methacrylate copolymer, such as the products sold under the names Amphomer®, Amphomer® LV 71, and Lovocryl® 47 by National Starch, and those of family (4), such as methyl methacrylate/dimethylcarboxymethylammonioethyl methacrylate copolymers, sold, for example, under the name Diaformer Z301 by Sandoz.

Nonionic Polymers

The polymers which may be used in the compositions of the present disclosure may also be chosen from nonionic polymers, such as:

polyalkyloxazolines;

vinyl acetate homopolymers;

copolymers of vinyl ester (the vinyl group being directly connected to the oxygen atom of the ester group and the vinyl ester having a saturated, linear or branched, hydrocarbon radical comprising from 1 to 19 carbon atoms bonded to the carbonyl of the ester group) and of at least one other monomer chosen from vinyl esters (other than the vinyl ester already present), α-olefins (comprising from 8 to 28 carbon atoms), acrylic esters, maleic esters, ethylenes, alkyl vinyl ethers (wherein the alkyl group comprises from 2 to 18 carbon atoms) and allyl and methallyl esters (having a saturated, linear or branched, hydrocarbon radical comprising from 1 to 19 carbon atoms bonded to the carbonyl of the ester group).

These copolymers can be partially crosslinked using crosslinking agents chosen from vinyl, allyl, and methallyl agents, such as tetraallyloxyethane, divinylbenzene, divinyl octanedioate, divinyl dodecanedioate, and divinyl octadecanedioate.

Non-limiting examples of these copolymers include: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl acetate/dibutyl maleate propionate, vinyl acetate/vinyl stearate, crosslinked with 0.2% of divinylbenzene, vinyl dimethylpropionate/vinyl laurate, crosslinked with 0.2% of divinylbenzene, vinyl acetate/octadecyl vinyl ether, crosslinked with 0.2% of tetraallyl-oxyethane, vinyl acetate/allyl stearate, crosslinked with 0.2% of divinylbenzene, vinyl acetate/1-octadecene, crosslined with 0.2% of divinylbenzene, and allyl propionate/allyl stearate, crosslinked with 0.2% of divinylbenezene.

homopolymers and copolymers of acrylic esters. In at least one embodiment, the homopolymers and copolymers may be obtained from monomers chosen from isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate, stearyl (meth)acrylate, and mixtures thereof. Examples of such polymers include, but are not limited to, the alkyl acrylate/cycloalkyl acrylate copolymer sold by Phoenix Chem. under the name Giovarez AC-5099 mL and copolymers of alkyl acrylates and of alkyl methacrylates, such as the products provided by Röhm & Haas under the names Primal® AC-261 K and Eudragit® NE 30 D, by BASF under the name 8845, and by Hoechst under the name Appretan® N9212;

copolymers of acrylonitrile and of a nonionic monomer chosen, for example, from butadiene and alkyl(meth) acrylates, such as the products provided under the name CJ 0601 B by Röhm & Haas;

styrene homopolymers;

copolymers of styrene and styrene derivatives (for example, methylstyrene, chlorostyrene, and chloromethylstyrene). According to one embodiment, the copolymer comprising at least one styrene block may be chosen from diblock, triblock, and multiblock copolymers and may have a form chosen from star and radial forms. The copolymer comprising at least one styrene block may additionally comprise, for example, at least one block chosen from alkylstyrene (AS) blocks, ethylene/butylene (EB) blocks, ethylene/propylene (EP) blocks, butadiene (B) blocks, isoprene (I) blocks, acrylate (A) blocks, methacrylate (MA) blocks, and combinations thereof. The copolymer comprising at least one block comprising styrene units and/or units derived from styrene can be chosen from diblock and triblock copolymers, for example, polystyrene/polyisoprene and polystyrene/polybutadiene copolymers, such as those sold or manufactured under the name "Luvitol HSB" by BASF, and those of the polystyrene/copoly(ethylene/propylene) type and the polystyrene/copoly(ethyl/butylene) type, such as those sold or manufactured under the trade name "Kraton" by Shell Chemical Co. and Gelled Permethyl 99A by Penreco.

Non-limiting examples of such copolymers include Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58 (blend of star block polymer and of triblock polymer), Gelled Permethyl 99A-753-59 (blend of star block polymer and of triblock polymer), Versagel 5970 and Versagel 5960 from Penreco (blend of star polymer and of triblock polymer in isododecane).

Styrene/methacrylate copolymers may also be used, such as the polymers sold under the references OS 129880, OS 129881, and OS 84383 by Lubrizol (styrene/methacrylate copolymer). Further examples include, but are not limited to, copolymers of styrene and of alkyl (meth)acrylate, such as the products Mowilith® LDM 6911, Mowilith® DM 611, and Mowilith® LDM 6070 provided by Hoechst, and the products Rhodopas® SD 215 and Rhodopas® DS 910 provided by Rhône-Poulenc.

polyamides;

vinyllactam homopolymers other than vinylpyrrolidone homopolymers, such as the polyvinylcaprolactam sold under the name Luviskol® Plus by BASF;

vinyllactam copolymers, such as the poly(vinylpyrrolidone/vinyllactam) copolymer sold under the trade name Luvitec® VPC 55K65W by BASF, poly(vinylpyrrolidone/vinyl acetate) copolymers, such as those sold under the name PVPVA® S630L by ISP and Luviskol® VA 73, VA 64, VA 55, VA 37, and VA 28 by BASF, and poly(vinylpyrrolidone/vinyl acetate/vinyl propionate) terpolymers, for example the product sold under the name Luviskol® VAP 343 by BASF.

vinylpyrrolidone copolymers, such as copolymers of $C_2$ to $C_{30}$ alkenes, such as $C_3$ to $C_{22}$ alkenes, and combinations thereof, for example, VP/vinyl laurate copolymer, VP/vinyl stearate copolymer, butylated polyvinylpyrrolidine (PVP), VP/hexadecane copolymer, VP/eicosene copolymer, VP/tricontene copolymer, and VP/acrylic acid/lauryl methacrylate copolymer. Such copolymers are sold, for example, by ISP under the names Ganex V 220 and Ganex V 216.

polymers carrying fluorinated groups which pertain, such as polyperfluoroethers, for example, the Fomblin products described in U.S. Pat. No. 5,948,393, and the alkyl (meth)acrylate/perfluoroalkyl (meth)acrylate copolymers described in European Patent No. 0 815 836 and U.S. Pat. No. 5,849,318.

nonionic polyurethanes, which may be chosen from nonassociative and associative polyurethanes.

As used herein, the term "nonassociative polyurethane" is understood to mean polycondensates comprising at least one polyurethane block and not comprising, in their structure, a terminal or pendant alkyl or alkenyl chain, comprising more than 10 carbon atoms. Such compounds are described, for example, in European Patent Nos. 0 751 162, 0 637 600, 0 648 485, 0 656 021, and 0 619 111, French Patent No. 2 743 297, and International Patent Application Publication No. WO 94/03510.

The nonassociative polyurethanes used in accordance with the present disclosure may be soluble in the cosmetically acceptable aqueous medium or may form a dispersion in this medium. Such a dispersion may comprise at least 0.05% of surfactant making it possible to disperse and keep dispersed the nonassociative polyurethane.

According to one embodiment, any type of surfactant may be used in the dispersion, for example, nonionic surfactants. The mean size of the particles of the nonassociative polyurethane in the dispersion may range, for example, from 0.1 to 1 micrometer.

In at least one embodiment, the nonassociative polyurethane can be formed of an arrangement of blocks, this arrangement being obtained, for example, from:

(1) at least one compound comprising at least two active hydrogen atoms per molecule;

(2) at least one diol or a mixture of diols comprising acid functional groups and their salts; and (3) at least one isocyanate chosen from di- and polyisocyanates.

According to one embodiment, the compounds (1) may be chosen from diols, diamines, polyesterols, polyetherols, and mixtures thereof.

The compounds (1) may be chosen, for example, from linear polyethylene glycols and polypropylene glycols, such as those which are obtained by reaction of ethylene or propylene oxide with water or diethylene or dipropylene glycol in the presence of sodium hydroxide as catalyst. These polyalkylene glycols generally may have a molecular weight ranging from 600 to 20 000.

Other suitable organic compounds include, but are not limited to, those which comprise at least one group chosen from mercapto, amino, carboxyl, and hydroxyl groups. Mention is more particularly made, among these, of polyhydroxylated compounds, such as polyether diols, polyester diols, polyacetal diols, polyamide diols, polyester polyamide diols, poly(alkylene ether) diols, polythioether diols and polycarbonate diols.

Non-limiting examples of polyether diols include the condensation products of ethylene oxide, of propylene oxide, and of tetrahydrofuran, and their copolymerization and condensation products, which are chosen from grafted and block products, such as mixtures of condensates of ethylene oxide and of propylene oxide, and products of the polymerization of olefins under high pressure, with alkylene oxide condensates. Appropriate polyether diols include, for example, those prepared by condensation of alkylene oxides and of polyhydric alcohols, such as ethylene glycol, 1,2-propylene glycol, and 1,4-butanediol.

According to one embodiment, the polyester diols, polyesteramides, and polyamide diols are saturated and are obtained, for example, from the reaction of saturated or unsaturated polycarboxylic acids with polyhydric alcohols, diamines, or polyamines. Examples of acids which may be used to prepare these compounds include, but are not limited to, adipic acid, succinic acid, phthalic acid, terephthalic acid, and maleic acid. Appropriate polyhydric alcohols for preparing the polyesters include, for example, ethylene glycol, 1,2-propylene glycol, 1,4-butanediol, neopentyl glycol, and hexanediol. Use may also be made of aminoalcohols, for example ethanolamine. Appropriate diamines for preparing polyesteramides include, but are not limited to, ethylenediamine and hexamethylenediamine.

Appropriate polyacetals can be prepared, for example, from 1,4-butanediol or hexanediol and formaldehyde. Appropriate polythioethers can be prepared, for example, by a condensation reaction between thioglycols, alone or in combination with other glycols, such as ethylene glycol and 1,2-propylene glycol, or with other polyhydroxylated compounds. Polyhydroxylated compounds comprising urethane groups, natural polyols, which can be further modified, for example, castor oil and carbohydrates, may also be used.

According to another embodiment, the compound of group (1) is chosen from polyesterols, for example, polyester diols formed by the reaction of at least one (di)polyol (1a) and of at least one acid (1b). The (di)polyol (1a) may be chosen, for example, from neopentyl glycol, 1,4-butanediol, hexanediol, ethylene glycol, diethylene glycol, propylene glycol, butylene glycol, neopentyl glycol, and (di)polyethylene glycol. The acid (1b) may be chosen, for example, from phthalic acid, isophthalic acid, adipic acid, and (poly)lactic acid.

Examples of compounds (2) include, but are not limited to, hydroxycarboxylic acids, such as dimethylolpropanoic acid (DMPA) and 2,2-dihydroxymethylcarboxylic acid. In at least one embodiment, the compound (2) is used as a coupling block. According to another embodiment, compound (2) is chosen from compounds comprising at least one poly($\alpha,\alpha$-dihydroxylated carboxylic acid).

Non-limiting examples of compounds (2) include 2,2-di(hydroxymethyl)acetic acid, 2,2-dihydroxymethylpropionic acid, 2,2-dihydroxymethylbutyric acid, and 2,2-dihydroxymethylpentanoic acid.

The di- or polyisocyanate (3) may be chosen, for example, from hexamethylene diisocyanate, isophorone diisocyanate (IDPI), toluoylene diisocyanate, 4,4'-diphenylmethane diisocyanate (DPMD), 4,4'-dicyclohexylmethane diisocyanate (DCMD), methylenedi-p-phenyl diisocyanate, methylenebis (4-cyclohexylisocyanate), toluene diisocyanates, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and of 2,6-toluene diisocyanates, 2,2'-dichloro-4,4'-diisocyanatodiphenylmethane, 2,4-dibromo-1,5-diisocyanatonaphthalene, 1,4-butane diisocyanate, 1,6-hexane diisocyanate, and 1,4-cyclohexane diisocyanate.

According to one embodiment, the nonassociative polyurethane can be formed using at least one additional compound (4) which may serve to extend its chain. These compounds (4) may be chosen, for example, from saturated and unsaturated glycols, such as ethylene glycol, diethylene glycol, neopentyl glycol, and triethylene glycol; amino alcohols, such as ethanolamine, propanolamine, and butanolamine; heterocyclic, aromatic, cycloaliphatic, and aliphatic primary amines; diamines; carboxylic acids, such as aliphatic, aromatic, and heterocyclic carboxylic acids, for example, oxalic, succinic, glutaric, adipic, sebacic, and terephthalic acids; and aminocarboxylic acids. In another embodiment, the compounds (4) are aliphatic diols.

According to a further embodiment, the nonassociative polyurethanes can be formed from at least one additional compound (5) having a silicone backbone, such as polysiloxanes, polyalkylsiloxanes, and polyarylsiloxanes, for example, polyethylsiloxanes, polymethylsiloxanes, and polyphenylsiloxanes, optionally comprising hydrocarbon chains grafted to the silicon atoms.

In another embodiment, the nonassociative polyurethanes may comprise at least one base repeat unit of formula (VI):

—O—B—O—CO—NH—R—NH—CO— (VI)

wherein:
B is chosen from divalent $C_1$ to $C_{30}$ hydrocarbon groups, optionally substituted by a group comprising at least one group chosen from carboxylic acid functional groups and/or sulphonic acid functional groups, the carboxylic and/or sulphonic acid functional groups being in the free form or else partially or completely neutralized by an inorganic or organic base, and R is a divalent group chosen from aliphatic $C_1$ to $C_{20}$ hydrocarbon groups, cycloaliphatic $C_3$ to $C_{20}$ hydrocarbon groups, and aromatic $C_6$ to $C_{20}$ hydrocarbon groups, for example, $C_1$ to $C_{20}$ alkylene groups, $C_6$ to $C_{20}$ arylene groups, $C_3$ to $C_{20}$ cycloalkylene groups, and combinations thereof, these groups being optionally substituted.

In at least one embodiment, the R group may be chosen from groups of the following formulas:

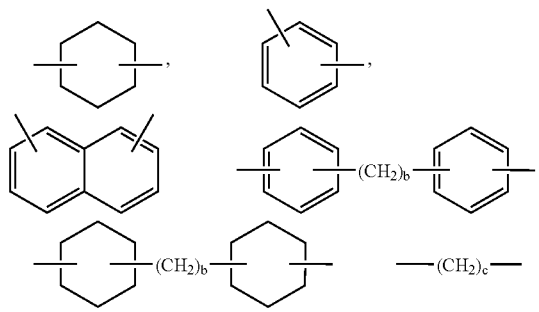

wherein b is an integer ranging from 0 to 3 and c is an integer ranging from 1 to 20, for example, from 2 to 12.

In one embodiment, the R group may be chosen from hexamethylene, 4,4'-biphenylenemethane, 2,4- and/or 2,6-tolylene, 1,5-naphthylene, p-phenylene, methylene-4,4-bis-cyclohexyl, and the divalent group derived from isophorone.

According to another embodiment, the nonassociative polyurethane may further comprise at least one polysiloxane sequence, the base repeat unit of which is chosen from units of formula (VII):

—O—P—O—CO—NH—R—NH—CO— (VII)

wherein:
P is a polysiloxane segment, and
R is a divalent group chosen from aliphatic $C_1$ to $C_{20}$ hydrocarbon groups, cycloaliphatic $C_3$ to $C_{20}$ hydrocarbon groups, and aromatic $C_6$ to $C_{20}$ hydrocarbon groups, for example, $C_1$ to $C_{20}$ alkylene groups, $C_6$ to $C_{20}$ arylene groups, $C_3$ to $C_{20}$ cycloalkylene groups, and combinations thereof, these groups being optionally substituted.

In a further embodiment, the polysiloxane segment P is chosen from those of formula (VIII):

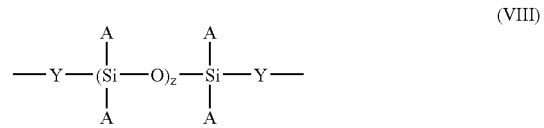

wherein:
the A groups, which may be identical or different, are chosen from aromatic groups and monovalent $C_1$ to $C_{20}$ hydrocarbon groups devoid or substantially devoid of ethylenic unsaturation,
Y is a divalent hydrocarbon group, and
z is an integer chosen such that the weight-average molecular weight of the polysiloxane segment ranges from 300 to 10 000.

In another embodiment, the divalent group Y may be chosen from alkylene groups of formula —$(CH_2)_a$— in which a is an integer ranging from 1 to 10.

The groups A can be chosen, for example, from $C_{1-8}$ alkyl groups, such as methyl, ethyl, propyl, isopropyl, butyl, pentyl, hexyl, and octyl groups; $C_{3-8}$ cycloalkyl groups, such as cyclohexyl groups; $C_{6-10}$ aryl groups, such as phenyl; $C_{7-10}$ arylalkyl groups, such as benzyl and phenylethyl, and tolyl and xylyl groups.

Non-limiting examples of nonassociative polyurethanes include the dimethylolpropionic acid/isophorone diisocyanate/neopentyl glycol/polyesterdiols copolymer (also known under the name of polyurethane-1, INCI name) sold under the trade name Luviset® PUR by BASF and the dimethylolpropionic acid/isophorone diisocyanate/neopentyl glycol/polyesterdiols/silicone diamine copolymer (also known under the name of polyurethane-6, INCI name) sold under the trade name Luviset® Si PUR A by BASF.

These polyurethanes present in the composition according to the present disclosure are employed in the non-neutralized and thus nonionic form.

As used herein, the term "associative polyurethane" is understood to mean a polyurethane having at least one end or pendent alkyl chain comprising at least 10 carbon atoms. This type of polymer is capable of interacting with itself or with other compounds, such as surfactants, which may result in the thickening of the medium.

Non-limiting examples of nonionic associative polyurethane include water-soluble or water-swellable acrylic copolymers comprising, for example:
a) from 40 to 99.5% by weight, such as from 30 to 65% by weight, of at least one nonsurfactant monomer comprising monoethylenic unsaturation; and
b) from 0.5 to 60% by weight, such as from 10 to 50% by weight, of at least one nonionic urethane monomer which is the reaction product of a monohydric nonionic surfactant with a monoisocyanate comprising monoethylenic unsaturation.

According to one embodiment, the copolymer comprises a significant amount, indicated above, of a monomer a) comprising monoethylenic unsaturation which does not have surfactant properties. Examples of monomers (a) include, but are not limited to, those which give water-insoluble polymers when they are homopolymerized, for instance, $C_1$-$C_4$ alkyl acrylates and methacrylates, such as methyl acrylate, ethyl acrylate, butyl acrylate, and the corresponding methacrylates. In at least one embodiment, the monomers (a) are chosen from methyl and ethyl (meth)acrylates. Other non-limiting examples of suitable monomers (a) include styrene, vinyltoluene, vinyl acetate, acrylonitrile and vinylidene chloride. According to another embodiment, unreacted monomers may be used, for example, those in which the sole ethylenic group is the only group which is reactive under the conditions of the polymerization. In a further embodiment, monomers which comprise groups which are reactive under the action of heat can be used in some situations, such as hydroxyethyl acrylate.

The monohydric nonionic surfactants used to obtain the nonionic urethane monomer b) may be chosen from those known in the art, for example, alkoxylated hydrophobic compounds comprising an alkylene oxide forming the hydrophilic part of the molecule. The hydrophobic compounds may generally comprise at least one group chosen from aliphatic alcohols and alkylphenols in which a carbon chain comprising at least six carbon atoms constitutes the hydrophobic part of the surfactant.

According to one embodiment, the monohydric nonionic surfactants are chosen from those of formula:

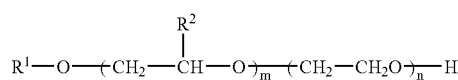

in which $R^1$ is chosen from $C_6$-$C_{30}$ alkyl and $C_8$-$C_{30}$ aralkyl groups, $R^2$ is chosen from $C_1$-$C_4$ alkyl groups, n is a mean number ranging from 5 to 150 and m is a mean number ranging from 0 to 50, with the proviso that n is at least as great as m and that the sum n+m ranges from 5 to 150.

Examples of suitable $C_6$-$C_{30}$ alkyl groups include, but are not limited to, dodecyl and $C_{18}$-$C_{26}$ alkyl radicals. Suitable aralkyl groups may be chosen, for example, from alkylphenyl groups wherein the alkyl is chosen from $C_8$-$C_{13}$ alkyl griyos. In at least one embodiment, the $R^2$ group is a methyl group.

The monoisocyanate comprising monoethylenic unsaturation used to form the nonionic urethane monomer b) may be chosen from highly varied compounds, for example, compounds comprising any copolymerizable unsaturation, such as acrylic and methacrylic unsaturations. Compounds comprising an allylic unsaturation conferred by allyl alcohol may also be used. According to one embodiment, the monoethylenic monoisocyanates are chosen from α,α-dimethyl-m-isopropenylbenzyl isocyanate and methylstyreneisopropyl isocyanate.

The acrylic copolymer defined above may be obtained by copolymerization in aqueous emulsion of the components a) and b), which is known in the art and described, for example, in European Patent Application No. 0 173 109.

Suitable nonionic associative polyurethanes useful in accordance with the present disclosure include, but are not limited to, polyether polyurethanes comprising, in their chain, both hydrophilic sequences of generally polyoxyethylene nature and hydrophobic sequences which can be aliphatic linkages alone and/or cycloaliphatic and/or aromatic linkages.

In at least one embodiment, the polyether polyurethanes comprise at least two lipophilic hydrocarbon chains comprising from 6 to 30 carbon atoms which are separated by a hydrophilic sequence, it being possible for the hydrocarbon chains to be pendent chains or chains at the end of the hydrophilic sequence. In one embodiment, the polyurethan comprises at least one pendent hydrocarbon chains. In another embodiment, the polymer can comprise a hydrocarbon chain at one end or at both ends of a hydrophilic sequence.

According to a further embodiment, the polyether polyurethanes can be polysequential, for instance, in the triblock form. The hydrophobic sequences can be at each end of the chain (for example: triblock copolymers comprising a central hydrophilic sequence) or distributed both at the ends and in the chain (e.g., polysequential copolymers). These polymers may also be chosen from graft polymers and star polymers.

In at least one embodiment, the nonionic polyether polyurethanes comprising a fatty chain can be triblock copolymers, the hydrophilic sequence of which is a polyoxyethoxyl chain comprising from 50 to 1000 ethoxyl groups. The nonionic polyether polyurethanes comprise a urethane bond between the hydrophilic sequences, hence the origin of the name.

By extension, the nonionic polyether polyurethanes comprising a fatty chain also include those comprising hydrophilic sequences which are bonded to the lipophilic sequences via other chemical bonds.

Non-limiting examples of nonionic polyether polyurethanes comprising a fatty chain include Rheolate 205 comprising a urea functional group sold by Rheox and Rholates 208, 204, and 212, Acrysol® 184, Elfacos T210 comprising a $C_{12-14}$ alkyl chain and Elfacos® T212 comprising a $C_{1-8}$ alkyl chain from Akzo, and DW 1206B from Röhm & Haas comprising a $C_{20}$ alkyl chain and comprising a urethane bond, provided at a dry matter content of 20% in water.

Solutions and dispersions of these polymers may also be used, for example, water and aqueous/alcoholic solutions and dispersions, such as Rheolate® 255, Rheolate® 278, and Rheolate® 244, sold by Rheox, and DW 1206F and DW 1206J provided by Röhm & Haas.

Polyether polyurethanes which are suitable for use in accordance with the present disclosure include, for example, those described in the paper by G. Fonnum, J. Bakke and Fk. Hansen, Colloid Polym. Sci., 271, 380-389 (1993).

Non-limiting examples of nonionic associative polyurethanes include polyether polyurethanes capable of being obtained by polycondensation of at least three compounds comprising (i) at least one polyethylene glycol comprising from 150 to 180 mol of ethylene oxide, (ii) at least one alcohol chosen from stearyl alcohol and decyl alcohol and (iii) at least one diisocyanate.

Such polyether polyurethanes are sold, for example, by Röhm & Haas under the names Aculyn® 46 and Aculyn® 44. Aculyn® 46 is a polycondensate of polyethylene glycol comprising 150 or 180 mol of ethylene oxide, of stearyl alcohol and of methylenebis(4-cyclohexyl isocyanate) (SMDI), at 15% by weight in a matrix of maltodextrin (4%) and of water (81%); Aculyn® 44 is a polycondensate of polyethylene glycol comprising 150 or 180 mol of ethylene oxide, of decyl alcohol and of methylenebis(4-cyclohexyl isocyanate) (SMDI), at 35% by weight in a mixture of propylene glycol (39%) and of water (26%).

According to one embodiment, the alkyl groups of the nonionic polymers mentioned above comprise from 1 to 6 carbon atoms.

According to another embodiment, the polymer is chosen from anionic, nonionic, and amphoteric polymers which are optionally film-forming and/or gelling.

As used herein, the term "film-forming" polymer is understood to mean a polymer capable of forming, by itself alone or in the presence of an additional agent which is able to form a film, a macroscopically continuous film on a support, for instance, on keratinous substances, such as a cohesive film and, in at least one embodiment, a film having a cohesion and mechanical properties such that the said film can be isolated from the support.

The compositions in accordance with the present disclosure may further comprise at least one agent commonly used in cosmetics chosen, for example, from reducing agents, fatty substances, plasticizing agents, softening agents, antifoaming agents, moisturizing agents, UV screening agents, inorganic colloids, peptizing agents, solubilizing agents, fragrances, anionic, cationic, nonionic, and amphoteric surfactants, proteins, vitamins, pearlescent agents, propellants, inorganic and organic thickening agents, such as benzylidenesorbitol and N-acylamino acids, waxes which may or may not be oxyethylenated, paraffins, $C_{10}$-$C_{30}$ fatty acids, such as stearic acid and lauric acid, and $C_{10}$-$C_{30}$ fatty amides, such as lauric acid diethanolamide.

The at least one optional additive may be present in the composition in an amount, for each of them, ranging from 0.01 to 20% by weight, with respect to the total weight of the composition.

It is to be understood that a person skilled in the art will take care to choose the at least one optional additive so that the advantageous properties intrinsically attached to the formation of the sheathing in accordance with the present disclosure are not, or not substantially, detrimentally affected.

The composition according to the present disclosure can be provided in a form chosen from creams, mousses, sticks, dispersions of vesicles, for example, of ionic and nonionic lipids, two-phase and multiphase lotions, sprays, aerosols, powders, and pastes.

In one embodiment, the composition can be an anhydrous composition, that is to say a composition comprising less than 2% by weight of water, for example, less than 0.5% of water, and in at least one embodiment, devoid of water, the water not being added during the preparation of the composition but, rather, corresponding to the residual water contributed by the ingredients.

The composition described above can be employed on dry or wet hair. After application of the composition of the present disclosure, with or without additives as described above, the hair may be dried under a hood dryer or using a hair dryer. The additives present can be applied to the hair simultaneously with the composition of the present disclosure or separately.

Following application of the composition and the optional additives, the hair may optionally be washed, although this washing operation is not essential.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below. Unless otherwise mentioned, the amounts are given as weight percentages relative to the total weight of the composition.

EXAMPLES

Example 1

The following composition was produced:

| | |
|---|---|
| Isopropanol | 50 g |
| Cyclopentadimethylsiloxane, sold by Dow Corning under the name of DC245 Fluid | 30 g |
| Mica coated with brown iron oxide pearlescent agent, sold by Eckart under the name Prestige Bronze | 10 g |
| Dimethylpolysiloxane/urea copolymer, sold under the reference Wacker-Belsil ® UD 60 by Wacker. | 10 g |

0.5 g of the composition was applied to a lock of clean and dry hair weighing 1 g. After a leave in time of 5 minutes, the lock was dried with a hairdryer for 2 minutes. A colored lock was obtained, the hairs of which were separate and the color of which was resistant to shampooing.

Example 2

The following composition was produced:

| | |
|---|---|
| Isopropanol | 45 g |
| Cyclopentadimethylsiloxane, sold by Dow Corning under the name of DC245 Fluid | 30 g |
| Polydimethylsiloxane, sold by Dow Corning under the reference Dow Corning 200 Fluid 60000 cs | 5 g |
| Mica coated with brown iron oxide pearlescent agent, sold by Eckart under the name Prestige Bronze | 10 g |
| Dimethylpolysiloxane/urea copolymer, sold under the reference Wacker-Belsil ® UD 60 by Wacker | 10 g |

0.5 g of the composition was applied to a lock of clean and dry hair weighing 1 g. After a leave-in time of 5 minutes, the lock was dried with a hairdryer for 2 minutes. A colored lock was obtained, the hairs of which were separate and the color of which was resistant to shampooing.

Example 3

The following composition was produced:

| | |
|---|---|
| Isopropanol | 50 g |
| Cyclopentadimethylsiloxane, sold by Dow Corning under the name of DC245 Fluid | 39 g |
| Disperse Red 13 | 1 g |
| Dimethylpolysiloxane/urea copolymer, sold under the reference Wacker-Belsil ® UD 60 by Wacker | 10 g |

0.3 g of the composition was applied to a lock of 1 g of clean and dry hair. After a leave-in time of 5 minutes, the lock was dried with a hairdryer for 2 minutes. A colored lock was obtained, the hairs of which were separate and the color of which was resistant to shampooing.

Example 4

The following composition was produced:

| | |
|---|---|
| Isopropanol | 45 g |
| Cyclopentadimethylsiloxane, sold by Dow Corning under the name of DC245 Fluid | 40 g |
| 3,6-Bis(bis[biphenyl]methyl)amino)-2,5-pyrazine dicarbonitrile* | 5 g |
| Dimethylpolysiloxane/urea copolymer, sold under the reference Wacker-Belsil ® UD 60 by Wacker | 10 g |

*cited in the following publications: Natu R. Patel, Journal of Heterocyclic Chemistry, Vol. 3, No. 4, 1966, pp. 512-517; Kazuko Shirai, Journal of the Society of Dyers and Colorists, Vol. 114, No. 12, December 1998, pp. 368-374.

0.3 g of the composition was applied to a lock of 1 g of clean and dry hair. After a leave-in time of 5 minutes, the lock was dried with a hairdryer for 2 minutes. A colored lock was obtained, the hairs of which were separate and the color of which was resistant to shampooing.

Example 5

The following composition was produced:

| | |
|---|---|
| Isopropanol | 50 g |
| Cyclopentadimethylsiloxane, sold by Dow Corning under the name of DC245 Fluid | 39 g |
| 5,6-Dihydroxyindole | 1 g |
| Dimethylpolysiloxane/urea copolymer, sold under the reference Wacker-Belsil ® UD 60 by Wacker | 10 g |

0.3 g of the composition was applied to a lock of 1 g of clean and dry hair. After a leave-in time of 5 minutes, the lock was dried with a hairdryer for 2 minutes. A colored lock was obtained, the hairs of which were separate and the color of which was resistant to shampooing.

Example 6

The following composition was produced:

| | |
|---|---|
| Isopropanol | 45 g |
| Cyclopentadimethylsiloxane, sold by Dow Corning under the name of DC245 Fluid | 30 g |
| Polydimethylsiloxane, sold by Dow Corning under the reference Dow Corning 200 Fluid 60000 cs | 5 g |
| Mica coated with brown iron oxide pearlescent agent, sold by Eckart under the name Prestige Bronze | 10 g |
| Dimethylpolysiloxane/urea copolymer, sold under the reference Wacker-Belsil ® UD 140 by Wacker | 10 g |

0.5 g of the composition was applied to a lock weighing 1 g of clean and dry hair. After a leave-in time of 5 minutes, the lock was dried with a hairdryer for 2 minutes. A colored lock was obtained, the hairs of which were separate and the color of which was resistant to shampooing.

What is claimed is:

1. A cosmetic composition comprising at least one nonionic polysiloxane/polyurea block copolymer, at least one colored or coloring entity, and at least one volatile nonsilicone organic solvent;

wherein the at least one polysiloxane/polyurea copolymer is chosen from compounds of formula (I):

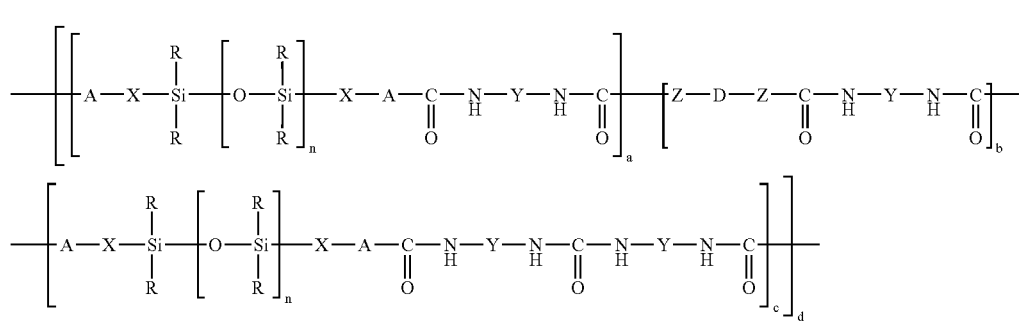

wherein:
R is chosen from monovalent hydrocarbon radicals comprising from 1 to 20 carbon atoms which can be substituted by at least one atom chosen from fluorine and chlorine atoms,
X is chosen from alkylene radicals comprising from 1 to 20 carbon atoms, in which nonneighboring methylene units can be replaced by —O— radicals,
A is chosen from oxygen and amino radicals —NR'—,
Z is chosen from oxygen and amino radicals —NR'—,
R' is chosen from hydrogen and alkyl radicals comprising from 1 to 10 carbon atoms,
Y is chosen from divalent hydrocarbon radicals, optionally substituted by at least one atom chosen from fluorine and chlorine, comprising from 1 to 20 carbon atoms,
D is chosen from alkylene radicals, optionally substituted by at least one radical chosen from fluorine, chlorine, $C_1$-$C_6$ alkyl, and $C_1$-$C_6$ alkyl ester radicals, comprising from 1 to 700 carbon atoms, in which nonneighboring methylene units can be replaced by at least one radical chosen from —O—, —COO—, —OCO—, and —OCOO— radicals,
n is a number ranging from 1 to 4000,
a is a number greater than or equal to 1,
b is a number ranging from 0 to 40,
c is a number ranging from 0 to 30, and
d is a number greater than 0, with the proviso that A, in at least one of the units (a), is an —NH— radical; and further comprising at least one silicone compound having a viscosity of less than 100 mm$^2$/s (100 cSt) at 25° C., wherein the at least one silicone compound is chosen from octamethylcyclotetrasiloxane, decamethylcyclopentasiloxane, dodecamethylcyclohexasiloxane, heptamethylhexyltrisiloxane, heptamethylethyltrisiloxane, heptamethyloctyltrisiloxane, octamethyltrisiloxane, decamethyltetrasiloxane, and mixtures thereof; and wherein the cosmetic composition is a hair dye.

2. The composition of claim 1, wherein the copolymer comprises at least one polyurethane block.

3. The composition of claim 1, wherein the copolymer comprises solely polysiloxane blocks and polyurea blocks.

4. The composition of claim 1, wherein the polysiloxane block of the copolymer is present in an amount by weight of polysiloxane of greater than 5%, relative to the total weight of the copolymer.

5. The composition of claim 4, wherein the polysiloxane block of the copolymer is present in an amount by weight of greater than 90% by weight, relative to the total weight of the copolymer.

6. The composition of claim 1, wherein, in the formula (I), R is methyl.

7. The composition of claim 1, wherein, in the formula (I), X is propylene.

8. The composition of claim 1, wherein, in the formula (I), Z is chosen from amino radicals and oxygen.

9. The composition of claim 1, wherein, in the formula (I), Y is chosen from linear and cyclic aralkylene radicals and alkylene radicals.

10. The composition of claim 1, wherein, in the formula (I), A is —NH— in all the units (a).

11. The composition of claim 10, wherein A is —NH— in all the units (a), (b), and (c).

12. The composition of claim 1, wherein the copolymer is capable of being obtained by a process comprising:

reacting a cyclic silazane chosen from silazanes of formulas (2) and (2'):

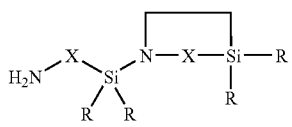

(2)

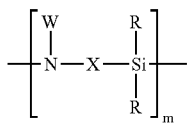

(2')

wherein W is chosen from hydrogen, substituted and unsubstituted hydrocarbon radicals comprising from 1 to 20 carbon atoms, and R$_2$Si—X—NH$_2$ radicals;

with an organic silicon compound of formula (3):

to give an aminoalkylpolydiorganosiloxane of formula (4):

and polymerizing the aminoalkylpolydiorganosiloxane of formula (4) with a diisocyanate of formula (5):

wherein:

m is a number ranging from 1 to 4000,

X is chosen from alkylene radicals comprising from 1 to 20 carbon atoms, in which nonneighboring methylene units can be replaced by —O—radicals, Y is chosen from divalent hydrocarbon radicals, optionally substituted by at least one atom chosen from fluorine and chlorine, comprising from 1 to 20 carbon atoms, R$_Z$ is chosen from monovalent hydrocarbon radicals comprising from 1 to 20 carbon atoms which can be substituted by at least one atom chosen from fluorine and chlorine atoms, and n is a number ranging from 1 to 4000.

13. The composition of claim 1, wherein the copolymer corresponds to the INCI name polyureadimethicone.

14. The composition of claim 1, wherein the volatile nonsilicone organic solvent is chosen from ethanol, isopropanol, acetone, and isododecane.

15. The composition of claim 1, wherein the colored or coloring entity is chosen from colored pigments, dye precursors, hydrophilic direct dyes, and hydrophobic direct dyes.

16. The composition of claim 1, wherein the colored entity is chosen from organic pigments, inorganic pigments, and pearlescent agents.

17. The composition of claim 1, further comprising at least one polysiloxane having a viscosity of greater than 100 cSt.

18. The composition of claim 1, further comprising at least one filler.

19. The composition of claim 1, further comprising at least one nonsilicone polymer.

20. The composition of claim 10, wherein the nonsilicone polymer is chosen from anionic, nonionic, and amphoteric polymers.

21. A method for coloring hair, comprising applying to the hair a cosmetic composition comprising at least one nonionic polysiloxane/polyurea block copolymer, at least one colored or coloring entity, and at least one volatile nonsilicone organic solvent;

wherein the at least one polysiloxane/polyurea copolymer is chosen from compounds of formula (I):

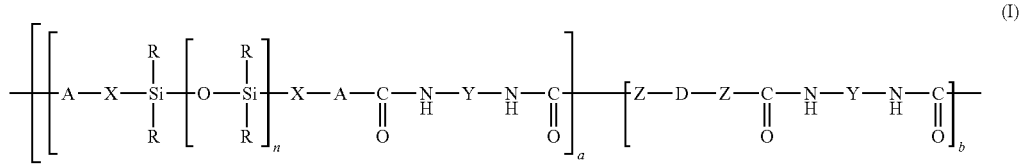

(I)

-continued

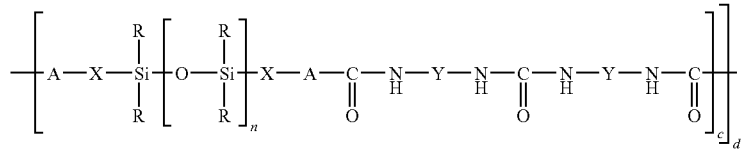

wherein:

R is chosen from monovalent hydrocarbon radicals comprising from 1 to 20 carbon atoms which can be substituted by at least one atom chosen from fluorine and chlorine atoms, X is chosen from alkylene radicals comprising from 1 to 20 carbon atoms, in which nonneighboring methylene units can be replaced by —O— radicals, A is chosen from oxygen and amino radicals —NR'—, Z is chosen from oxygen and amino radicals —NR'—, R' is chosen from hydrogen and alkyl radicals comprising from 1 to 10 carbon atoms, Y is chosen from divalent hydrocarbon radicals, optionally substituted by at least one atom chosen from fluorine and chlorine, comprising from 1 to 20 carbon atoms, D is chosen from alkylene radicals, optionally substituted by at least one radical chosen from fluorine, chlorine, $C_1$-$C_6$ alkyl, and $C_1$—$C_6$ alkyl ester radicals, comprising from 1 to 700 carbon atoms, in which nonneighboring methylene units can be replaced by at least one radical chosen from —O—, —COO—, —OCO—, and —OCOO— radicals, n is a number ranging from 1 to 4000, a is a number greater than or equal to 1, b is a number ranging from 0 to 40, c is a number ranging from 0 to 30, and d is a number greater than 0, with the proviso that A, in at least one of the units (a), is an —NH— radical; and further comprising at least one silicone compound having a viscosity of less than 100 mm$^2$/s (100 cSt) at 25° C., wherein the at least one silicone compound is chosen from octamethylcyclotetrasiloxane, decamethylcyclopentasiloxane, dodecamethylcyclohexasiloxane, heptamethylhexyltrisiloxane, heptamethylethyltrisiloxane, heptamethyloctyltrisiloxane, octamethyltrisiloxane, decamethyltetrasiloxane, and mixtures thereof; and wherein the cosmetic composition is a hair dye.

* * * * *